US008420327B2

(12) United States Patent
Ellis et al.

(10) Patent No.: US 8,420,327 B2
(45) Date of Patent: Apr. 16, 2013

(54) ANALYTE SENSORS, METHODS FOR PREPARING AND USING SUCH SENSORS, AND METHODS OF DETECTING ANALYTE ACTIVITY

(75) Inventors: April L. Ellis, Pinson, AL (US); Yiming Ye, Duluth, GA (US); Angela Holder, Mableton, GA (US); Yun Huang, Decatur, GA (US); Michael Kirberger, Hampton, GA (US); Jenny Jie Yang, Atlanta, GA (US); Jin Zou, Lilburn, GA (US); Wei Yang, Changchun (CN)

(73) Assignee: Georgia State University Research Foundation, Atlanta, GA (US)

( * ) Notice: Subject to any disclaimer, the term of this patent is extended or adjusted under 35 U.S.C. 154(b) by 481 days.

(21) Appl. No.: 12/448,101

(22) PCT Filed: Dec. 14, 2007

(86) PCT No.: PCT/US2007/025623
§ 371 (c)(1),
(2), (4) Date: Apr. 2, 2010

(87) PCT Pub. No.: WO2008/076365
PCT Pub. Date: Jun. 26, 2008

(65) Prior Publication Data
US 2010/0196918 A1    Aug. 5, 2010

Related U.S. Application Data

(60) Provisional application No. 60/869,968, filed on Dec. 14, 2006.

(51) Int. Cl.
*G01N 33/53* (2006.01)
(52) U.S. Cl.
USPC .......................................... 435/7.1; 436/518
(58) Field of Classification Search .................. None
See application file for complete search history.

(56) References Cited

U.S. PATENT DOCUMENTS

| | | | |
|---|---|---|---|
| 5,679,548 A | 10/1997 | Barbas et al. | |
| 5,690,903 A | 11/1997 | Hainfeld | |
| 5,922,302 A | 7/1999 | Goldenberg et al. | |
| 6,197,258 B1 | 3/2001 | Thompson et al. | |
| 6,916,623 B2 * | 7/2005 | Seki et al. | 435/7.1 |
| 6,924,119 B2 * | 8/2005 | Umezawa et al. | 435/15 |
| 7,049,400 B1 | 5/2006 | Chang | |
| 2001/0008766 A1 * | 7/2001 | Daunert et al. | 435/7.5 |
| 2002/0015038 A1 | 2/2002 | Patel et al. | |
| 2002/0136692 A1 | 9/2002 | Haroon et al. | |
| 2002/0160473 A1 * | 10/2002 | Lukyanov et al. | 435/183 |
| 2003/0149254 A1 | 8/2003 | Anderson et al. | |
| 2003/0180222 A1 | 9/2003 | Zhang et al. | |
| 2004/0208827 A1 | 10/2004 | McMurry et al. | |
| 2006/0029942 A1 * | 2/2006 | Yang | 435/6 |
| 2006/0030029 A1 | 2/2006 | Yang | |
| 2006/0031020 A1 | 2/2006 | Yang | |

FOREIGN PATENT DOCUMENTS

| | | |
|---|---|---|
| EP | 1238982 A | 9/2002 |
| WO | 0130398 A2 | 5/2001 |
| WO | 02063035 A | 8/2002 |
| WO | 03014157 A2 | 2/2003 |
| WO | 03025220 A2 | 3/2003 |
| WO | 03057829 A2 | 7/2003 |
| WO | 2006080022 A2 | 8/2006 |
| WO | 2006107794 A2 | 10/2006 |
| WO | 2007009058 A2 | 1/2007 |

OTHER PUBLICATIONS

Supplemental European Search Report dated Mar. 29, 2010.
Doi Nobuhide, et al, "Evolutionary Design of Generic Green Fluorescent Protein Biosensors" Methods in Molecular Biology, Humana Press Inc., NJ, vol. 1183, Jan. 1, 2002, pp. 49-55.
J. Zhou, et al., "Developing Sensors for Real-Time Measurement of High Ca Concentrations", Biochemistry, vol. 46, Sep. 10, 2007, pp. 12275-12288.
Supplemental European Search Report dated Sep. 23, 2009.
Chen Ning, et al., "Development of protease sensors based on enhanced fluorescent protein (EGFP)." Abstracts of Papers American Chemical Society, vol. 231, Mar. 2006, pp. 31-MEDI, National Meeting of the American Chemical Society, Atlanta, GA Mar. 26-30, 2006.
Mesecar, et al., "Orbital Steering in the Catalytic Power of Enzymes: Small Structural Changes with Large Catalytic Consequences," Science Jul. 11, 1997:277(5323):202-6.
Smith, et al., "Entry for Quaternary Structure," Oxford Dictionary of Biochemistry and Molecular Biology, Oxford University Press, New Yoir 1997, p. 551.
Todd, et al., "Engineered Metal Binding Sites on Green Fluorescence Protein," Biochemical and Biophysical Research Communications, vol. 268, No. 2, Feb. 16, 2000, pp. 462-465.
Romoser, et al., "Detection in Living Cells of Ca-2+-dependent Changes in the Fluroescence Emission of an Indicator Composed of Two Green Fluorescent Protein Variants Linked by a Calmodulin-binding Sequence: A New Class of Fluorescent Indicators," Journal of Biological Chemistry, col. 272, No. 20, 1997, pp. 13270-13274.
Nagal, et al., "Circularly Permuted Green Fluorescent Proteins Engineered to Sense Ca2+" Proceedings of the National Academy of Sciences of USA, National Academy of Science, Washington, DC, vol. 98, No. 6, Mar. 13, 2001, pp. 3197-3202.
Wilkins, et al., "Metal-Binding Studies for a De Novo Designed Calcium-Binding Protein," Protein Engineering, vol. 15, No. 7, Jul. 2002, pp. 571-574.

(Continued)

*Primary Examiner* — Jacob Cheu
(74) *Attorney, Agent, or Firm* — Thomas Horstemeyer, LLP

(57) ABSTRACT

Embodiments of the present disclosure provide for analyte sensors, methods for producing and using the analyte sensors, methods of detecting and/or measuring analyte activity, methods for characterizing analyte cellular activity, methods of detecting pH change in a system, method of controlling the concentration of an analyte in a system, fusion proteins, polynucleotides, and vectors corresponding to the analyte sensors, kits, and the like.

11 Claims, 23 Drawing Sheets
(9 of 23 Drawing Sheet(s) Filed in Color)

OTHER PUBLICATIONS

Hellinga, et al., "Protein Engineering and the Development of Generic Biosensors," Trends in Biotechnology, vol. 16, No. 4, 1998, p. 183.

Supplemental European Search Report dated Aug. 25, 2009.

Elbanowski, et al., "Fluorescence of Lanthanide (III) Complexes in Aqueous Solutions: The Influence of pH and Solution Composition," Monatshfte fur Chemie, 1985, vol. 116, pp. 901-911.

Johnson, et al., "Structural Changes Required for Activation of Protein C are Induced by CA2+ Binding to a High Affinity Site that Does Not Contain g-Carboxyglutamic Acid," The Journal of Biological Chemistry, 1983, vol. 268, pp. 5554-5560.

Lewis, et al., "Fluroescence Binding Assay for a Small Peptide Based on a GFP Fusion Protein," Analytica Chimica Acta., vol. 397, 1999, pp. 279-286.

Schlyer et al., "Time-Resolved Room Temperature Protein Phosphorescence: Nonexponential Decay from Single Emitting Tryptophans," Biophysical Journal, vol. 67, 1994, pp. 1192-1202.

Yang, et al., "The Molecular Structure of Green Fluorescent Protein," Nature Biotechnology, vol. 14, 1996, pp. 1246-151.

Shelling, et al., "Protein Nuclear Magnetic Resonance Studies of the Interaction of the Lanthanide Yetterbium and Lutetium with Apo- and Calcium Saturated Porcine Intestinal Calcium Binding Protein," Biochemistry, 1985, vol. 24, pp. 2332-2338.

Yang, et al., "Rational Design of a Calcium-Binding Protein," Journal of the American Chemical Society, Apr. 2003, vol. 125, pp. 6165-6171.

Ye, et al., "A Grafting Approach to Obtain Site-Specific Metal-Binding Properties of EF-Hand Proteins," Protein Engineering, vol. 16, No. 6; pp. 429-434, 2003.

Ye, et al., "Metal Binding Affinity and Structural Properties of an Isolated EF-Loop in a Scaffold Protein," Protein Engineering, vol. 14, No. 12, pp. 1001-1013; 2001.

MacKenzie, et al., "Bifunctional Fusion Proteins Consisting of a Single-Chain Antibody and an Engineered Lanthanide=Binding Protein," Immunotechnology 1 (1995), pp. 139-150.

Lee, et al., "Isolated EF-Loop III of Calmodulin in a Scaffold Protein Remains Unpaired in Solution Using Pulsed-Field-Gradient NMR Spectroscopy," Biochimica et Biophysica Acta; 1598 (2002), pp. 80-87.

Miyawaki, et al., Fluorescent Indicators for CA2+ Based on Green Fluorescent Proteins and Calmodulin; Nature, vol. 388, Aug. 28, 1997, pp. 882887.

Prasher, et al., "Primary Structure of the Aequorea Victoria Green-Fluorescent Protein," Gene, 1992, vol. 111, 99. 229-233.

Yang et al., "Obtaining Site-Specific Calcium-Binding Affinities of Calmodulin," Protein and Peptide Letters, vol. 10, No. 4, pp. 331-345, 2003.

Kawasaki, et al., "Classification and Evolution of EF-Hand Proteins," BioMetals; 1998, vol. 11, pp. 275-295.

International Search Report and Written Opinion, dated Jul. 14, 2008.

Anton, et al., "Biotinylation of a Bombesin" 1991, Peptides, 12, pp. 375-381.

International Search Report and Written Opinion dated Nov. 28, 2007.

Cohen, et al., "Ferritin as an Endogenous MRI Reporter for Noninvasive Imaging of Gene Expression in C6 Glioma Tumors," Neoplasia, Feb. 2005, vol. 7, No. 2, pp. 109-111.

Pessl, et al., "A Designed Metal-Binding Protein with a Novel Fold," Nature, Mar. 25, 1993, 362, 367, 369 (online).

* cited by examiner

A
| | |
|---|---|
| Ca-G1' | EGFP(1-172)-III-EGFP(173-238) |
| Ca-G1 | EGFP(1-172)-E-III-F-EGFP(173-238) |
| Ca-G1-37 | EGFP(1-172)-E-III-F-EGFP(173-238) M153T/V163A |
| Ca-G1-ER | kz-CRsig- EGFP(1-172)-E-III-F-EGFP(173-238)-KDEL |
| Ca-G2' | EGFP(1-157)-III-EGFP(158-238) |
| Ca-G2 | EGFP(1-157)-E-III-F-EGFP(158-238) |
| Ca-G3' | EGFP(1-144)-III-EGFP(145-238) |
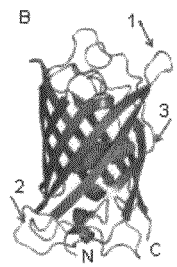
FIG. 1
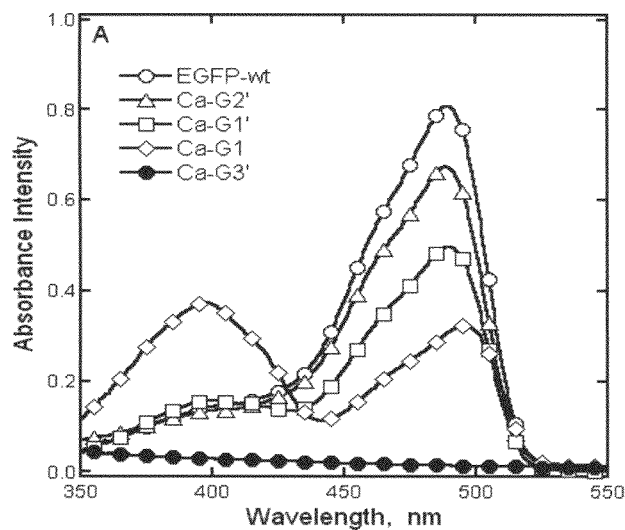
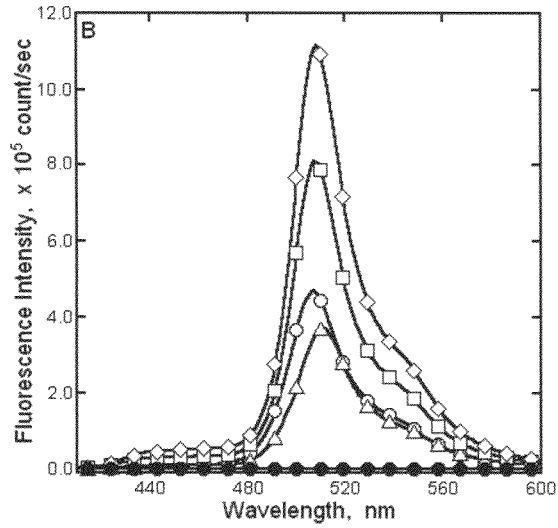
FIG. 2

Table 1 Spectroscopic property of EGFP, EGFP-D2, and EGFP-G1 and their C2 and C3 mutations

|  | Extinction Coefficient ($\varepsilon$), $M^{-1} cm^{-1}$ | | Quantum Yield 488 nm |
| --- | --- | --- | --- |
|  | 398 nm | 488 nm |  |
| EGFP | 5126.6 | 55900 | 0.60 |
| EGFP-C2 | 7184.3 | 55506 | 0.58 |
| EGFP-C3 | 6672.1 | 55840 | 0.63 |
| EGFP-G1 | 9228.1 | 28463 | 0.59 |
| EGFP-G1-C2 | 14063 | 26999 | 0.68 |
| EGFP-G1-C3 | 9906.1 | 28401 | 0.69 |
| EGFP-D2 | 1291.5 | 9323.8 | 0.56 |
| EGFP-D2-C2 | 5490.0 | 52989 | 0.53 |
| EGFP-D2-C3 | 5404.6 | 56416 | 0.51 |

FIG. 14

Table 1 Summary of Calcium-Binding Green Fluorescent Proteins

| Design Site | Calcium-binding Ligands | Average Distance to the Chromophore (Å) | Charge of a.a. in binding site | Average distance between binding site and Trp (Å) | Tb(III) $K_d$ (μM)[a] | Ca(II) $K_d$ (μM)[b] |
|---|---|---|---|---|---|---|
| GFP.D1 | Q177N, I171D, D173, S175D, N135 | 22 | -3 | 17 | 1.9 ± 0.4 | 60 ± 5 |
| GFP.D2 | E5, D82, S2D, D82, L194E | 15 | -5 | 29 | N/A | 107 ± 13 |
| GFP.D2' | E5, D82, K79D, L194N, K85D | 15 | -4 | 29 | 32 ± 13 | 96 ± 7 |
| GFP.D2'' | E5, D82, K79D, L194N, S86D | 15 | -4 | 30 | 2.9 ± 0.3 | 38 ± 5 |
| GFP.D3 | E115, V120N, R122D, K113D, E17 | 14 | -4 | 15 | 4.9 ± 0.2 | 57 ± 2 |

Table 1 A table of the design sites engineered into Green Fluorescent Protein with the charge of the amino acids in the binding site and the terbium and calcium binding affinities. For 120, 177, and 194a the terbium affinities were measured in a 20 mM PIPES, 10 mM KCl, 1 mM DTT, 1% glycerol, pH 6.8. For 194b, the terbium affinity was measured in b10 mM Tris, 1 mM DTT, 1% glycerol, pH 7.4. The calcium affinities for all four sites were measured in b10 mM Tris, 1 mM DTT, 1% glycerol, pH 7.4.

FIG. 19

FIG. 20A, Table A

| ID | Name | Method | Location | Host | Type | Other name |
|---|---|---|---|---|---|---|
| 1 | EGFP-III-172 | Grafting | 172 | EGFP-wt | Ca-sensor | Ca-G1' |
| 2 | EGFP-E-III-172 | | | | Ca-sensor | |
| 3 | EGFP-III-F-172 | | | | Ca-sensor | |
| 4 | EGFP-E-III-F-172 | | | | Ca-sensor | Ca-G1, EGFP-G1 |
| 5 | EGFP-E-III-F-172-ER | | | | Ca-sensor targeted ER | Ca-G1-ER |
| 6 | EGFP-E-III-F-172-mito | | | | Ca-sensor targeted Mito | |
| 7 | EGFP-E-III-F-172-SKEAA | | | | Ca-sensor | |
| 8 | EGFP-E-III-F-172-D/N | | | | Ca-sensor | |
| 9 | EGFP-E-III-F-172-DD/NN | | | | Ca-sensor | |
| 10 | EGFP-E-III-F-172-L194N | | | | Ca-sensor | |
| 11 | EGFP-I-172 | | | | Ca-sensor | |
| 12 | EGFP-α-Lac1-172 | | | | Ca-sensor | |
| 13 | EGFP-α-Lac2-172 | | | | Ca-sensor | |
| 14 | EGFP-α-Lac3-172 | | | | Ca-sensor | |
| 15 | EGFP-α-Lac4-172 | | | | Ca-sensor | |
| 16 | EGFP-III-172-C2 | | | EGFP-wt-C2 | Ca-sensor | |
| 17 | EGFP-E-III-172-C2 | | | | Ca-sensor | |
| 18 | EGFP-III-F-172-C2 | | | | Ca-sensor | |
| 19 | EGFP-E-III-F-172-C2 | | | | Ca-sensor | Ca-G1-37, EGFP-G1-C2 |
| 20 | EGFP-E-III-F-172-C2-ER | | | | Ca-sensor targeted ER | |
| 21 | EGFP-E-III-F-172-C2-mito | | | | Ca-sensor targeted Mito | |
| 22 | EGFP-E-III-F-172-SKEAA-C2 | | | | Ca-sensor | |
| 23 | EGFP-E-III-F-172-D/N-C2 | | | | Ca-sensor | |
| 24 | EGFP-E-III-F-172-DD/NN-C2 | | | | Ca-sensor | |
| 25 | EGFP-E-III-F-172-L194N-C2 | | | | Ca-sensor | |
| 26 | EGFP-I-172-C2 | | | | Ca-sensor | |
| 27 | EGFP-α-Lac1-172-C2 | | | | Ca-sensor | |
| 28 | EGFP-α-Lac2-172-C2 | | | | Ca-sensor | |
| 29 | EGFP-α-Lac3-172-C2 | | | | Ca-sensor | |
| 30 | EGFP-α-Lac4-172-C2 | | | | Ca-sensor | |

FIG. 20B, Table A

| # | Name | | | Type | Alt |
|---|---|---|---|---|---|
| 31 | EGFP-III-172-C3 | | | Ca-sensor | |
| 32 | EGFP-E-III-172-C3 | | | Ca-sensor | |
| 33 | EGFP-III-F-172-C3 | | EGFP-wt-C3 | Ca-sensor | |
| 34 | EGFP-E-III-F-172-C3 | | | Ca-sensor | EGFP-G1-C3 |
| 35 | EGFP-E-III-F-172-C3-ER | | | Ca-sensor targeted ER | |
| 36 | EGFP-E-III-F-172-C3-mito | | | Ca-sensor targeted Mito | |
| 37 | EGFP-E-III-F-172-SKEAA-C3 | | | Ca-sensor | |
| 38 | EGFP-E-III-F-172-D/N-C3 | | | Ca-sensor | |
| 39 | EGFP-E-III-F-172-DD/NN-C3 | | | Ca-sensor | |
| 40 | EGFP-E-III-F-172-L194N-C3 | | | Ca-sensor | |
| 41 | EGFP-I-172-C3 | | | Ca-sensor | |
| 42 | EGFP-α-Lac1-172-C3 | | | Ca-sensor | |
| 43 | EGFP-α-Lac2-172-C3 | | | Ca-sensor | |
| 44 | EGFP-α-Lac3-172-C3 | | | Ca-sensor | |
| 45 | EGFP-α-Lac4-172-C3 | | | Ca-sensor | |
| 46 | EGFP-III-157 | | 157 | Ca-binding protein | Ca-G2' |
| 47 | EGFP-E-III-F-157 | | EGFP-wt | Ca-binding protein | Ca-G2 |
| 48 | EGFP-III-157-C2 | | EGFP-wt-C2 | Ca-binding protein | |
| 49 | EGFP-III-157-C3 | | EGFP-wt-C3 | Ca-binding protein | |
| 50 | EGFP-E-III-F-157-C2 | | | Ca-binding protein | |
| 51 | EGFP-E-III-F-157-C3 | | | Ca-binding protein | |
| 52 | EGFP-E-III-F-170 | | 170 | Ca-sensor | |
| 53 | EGFP-E-I-F-170 | | EGFP-wt | Ca-sensor | |
| 54 | EGFP-E-III-F-170-C2 | | EGFP-wt-C2 | Ca-sensor | |
| 55 | EGFP-E-I-F-170-C2 | | | Ca-sensor | |
| 56 | EGFP-E-III-F-170-C3 | | EGFP-wt-C3 | Ca-sensor | |
| 57 | EGFP-E-I-F-170-C3 | | | Ca-sensor | |
| 58 | EGFP-120 | Designing | | Ca-binding protein | GFP.D3 |
| 59 | EGFP-120b | | | Ca-binding protein | |
| 60 | EGFP-177 | | | Ca-sensor | GFP.D1 |
| 61 | EGFP-194a | | | Ca-binding protein | GFP.D2' |
| 62 | EGFP-194b | | | Ca-binding protein | GFP.D2'' |
| 63 | EGFP-229 | | | Ca-binding protein | |

FIG. 20C, Table A

| | | | | |
|---|---|---|---|---|
| 64 | EGFP-site1 | | | Ca-sensor |
| 65 | EGFP-site1-ER | | | Ca-sensor targeted ER |
| 66 | EGFP-site1-mito | | | Ca-sensor targeted Mito |
| 67 | EGFP-site2 | | | Ca-binding protein |
| 68 | EGFP-site3 | | | Ca-binding protein |
| 69 | EGFP-site4 | | | Ca-binding protein |
| 70 | EGFP-site5 | | | Ca-binding protein |
| 71 | EGFP-site6 | | | Ca-binding protein |
| 72 | EGFP-120-C2 | | EGFP-wt-C2 | Ca-binding protein |
| 73 | EGFP-120b-C2 | | | Ca-binding protein |
| 74 | EGFP-177-C2 | | | Ca-sensor |
| 75 | EGFP-194a-C2 | | | Ca-binding protein |
| 76 | EGFP-194b-C2 | | | Ca-binding protein |
| 77 | EGFP-229-C2 | | | Ca-binding protein |
| 78 | EGFP-site1-C2 | | | Ca-sensor |
| 79 | EGFP-site1-C2-ER | | | Ca-sensor targeted ER |
| 80 | EGFP-site1-C2-mito | | | Ca-sensor targeted Mito |
| 81 | EGFP-site2-C2 | | | Ca-binding protein |
| 82 | EGFP-site3-C2 | | | Ca-binding protein |
| 83 | EGFP-site4-C2 | | | Ca-binding protein |
| 84 | EGFP-site5-C2 | | | Ca-binding protein |
| 85 | EGFP-site6-C2 | | | Ca-binding protein |
| 86 | EGFP-120-C3 | | EGFP-wt-C3 | Ca-binding protein |
| 87 | EGFP-120b-C3 | | | Ca-binding protein |
| 88 | EGFP-177-C3 | | | Ca-sensor |
| 89 | EGFP-194a-C3 | | | Ca-binding protein |
| 90 | EGFP-194b-C3 | | | Ca-binding protein |
| 91 | EGFP-229-C3 | | | Ca-binding protein |
| 92 | EGFP-site1-C3 | | | Ca-sensor |
| 93 | EGFP-site1-C3-ER | | | Ca-sensor targeted ER |
| 94 | EGFP-site1-C3-mito | | | Ca-sensor targeted Mito |
| 95 | EGFP-site2-C3 | | | Ca-binding protein |
| 96 | EGFP-site3-C3 | | | Ca-binding protein |

FIG. 20D, Table A

| 97 | EGFP-site4-C3 | | | | Ca-binding protein |
| --- | --- | --- | --- | --- | --- |
| 98 | EGFP-site5-C3 | | | | Ca-binding protein |
| 99 | EGFP-site6-C3 | | | | Ca-binding protein |

US 8,420,327 B2

ANALYTE SENSORS, METHODS FOR PREPARING AND USING SUCH SENSORS, AND METHODS OF DETECTING ANALYTE ACTIVITY

CROSS-REFERENCE TO RELATED APPLICATION

This application claims priority to the PCT application entitled "Analyte Sensors, Methods for Preparing and Using Such Sensors, and Methods of Detecting Analyte Activity," having serial number PCT/US2007/025623, filed on Dec. 14, 2007. This application also claims priority to and benefit of U.S. Provisional Patent Application No. 60/869,968, filed on Dec. 14, 2006, which is incorporated by reference in its entirety.

FEDERAL SPONSORSHIP

This invention was made with Government support under Contract/Grant No. GM070555, awarded by the National Institutes of Health. The Government has certain rights in this invention.

BACKGROUND $Ca^{2+}$ regulates many biological processes including neuronal signaling, muscle contraction, and cell development and proliferation. Depending on their intracellular location, $Ca^{2+}$ signals vary in amplitude and duration, together forming a complex $Ca^{2+}$ signaling code. The endoplasmic reticulum (ER) functions as the primary intracellular $Ca^{2+}$ store and is the site of protein synthesis and processing. Disruption of ER $Ca^{2+}$ homeostasis triggers the ER stress response, a source of cell death signals. The release of $Ca^{2+}$ from ER stores results in a rapid increase in $[Ca^{2+}]_{ER}$ and the released $Ca^{2+}$ binds to a number of intracellular $Ca^{2+}$ sensing proteins, such as calmodulin (CaM) and troponin C (TnC), as well as ion channels and enzymes to regulate a variety of cellular events and processes. Several human diseases, including various cardiomyopathies, Alzheimer's disease, cancer, and lens cataract formation are known to be associated with altered $Ca^{2+}$ signaling and altered $Ca^{2+}$ regulation by the ER store.

Because of the essential role of the ER in $Ca^{2+}$ signaling, the determination of free $[Ca^{2+}]_{ER}$ and its dynamic changes during cell signaling has attracted extensive interest. However, the lack of tractable biological $Ca^{2+}$ indicators with affinities in the high μM to mM range has made it difficult to directly assess changes in $[Ca^{2+}]_{ER}$. Current estimates of $[Ca^{2+}]_{ER}$ have been derived using three major types of $Ca^{2+}$ indicators and sensors (18-23). These are: (1) synthetic small molecule fluorescent indicators such as Mag-Fura-2, (2) specifically modified derivatives of the chemiluminescent protein (photoprotein) aequorin, and (3) fluorescent indicators based on green fluorescence protein (GFP) variants with CaM or TnC. Although some small molecule dyes will accumulate in certain cellular compartments of cells, they cannot be unambiguously targeted to specific intracellular locations; invasive methods are frequently required to eliminate the large fluorescence background resulting from the presence of these dyes in the cytosol. Targeted aequorins overcome some of the problems associated with the compartmentalized dye approach, but the low light output of these probes and the requirement for a soluble co-factor (coelenterazine) limit their usefulness.

GFP-based $Ca^{2+}$ sensors, such as cameleons and pericams originally engineered by the groups of Miyawaki, Persechini, and Tsien, are based on either fluorescence resonance energy transfer (FRET) between two different GFP variants, or the effect of a $Ca^{2+}$-dependent conformational change in natural $Ca^{2+}$ sensing proteins (e.g. CaM) on the protonation state of the chromophore of a single GFP variant. Because these sensors are based on naturally-occurring essential $Ca^{2+}$ binding proteins, a perturbation of the cellular environment through their introduction cannot be excluded, although many efforts have been made to decrease this possibility. Thus, there is a need to develop $Ca^{2+}$ sensors that minimally compete for $Ca^{2+}$ with existing cellular $Ca^{2+}$ binding proteins and/or its target proteins, show robust $Ca^{2+}$ responses, and exhibit $Ca^{2+}$ binding affinities comparable to that of different cellular compartments, such as the ER. Accordingly, there is a need for improved analyte sensors and methods for measuring and detecting analyte activity.

SUMMARY

Embodiments of the present disclosure provide for analyte sensors, methods for producing and using the analyte sensors, methods of detecting and/or measuring analyte activity, methods for characterizing analyte cellular activity, methods of detecting pH change in a system, method of controlling the concentration of an analyte in a system, fusion proteins, polynucleotides, and vectors corresponding to the analyte sensors, kits, and the like.

One exemplary analyte sensor, among others, includes: a molecular recognition motif that binds an analyte; and an optically-active fluorescent host protein in which the molecular recognition motif is operatively linked to or integrated therein, and wherein the interaction of the analyte to the molecular recognition motif produces a detectable change, wherein the analyte sensor has a protein sequence that includes the molecular recognition motif and the optically-active fluorescent host protein selected from: SEQ ID NOS: 1 to 99.

One exemplary analyte sensor, among others, includes: a molecular recognition motif that binds an analyte; and an optically-active fluorescent host protein in which the molecular recognition motif is operatively linked to or integrated therein, and wherein the interaction of the analyte to the molecular recognition motif produces a detectable change, wherein the analyte sensor has at least one characteristic selected from: is stable at temperatures greater than about 30° C.; increased fluorescent signals with either excitation or emission intensity changes, absorbance signal changes, NMR chemical shift changes, and combinations thereof.

One exemplary method of detecting the activity of an analyte, among others, includes: providing a analyte sensor as provided above; introducing the analyte sensor to a host; measuring a signal produced from the analyte sensor, and comparing the signal to a standard signal from the analyte sensor prior to interaction with an analyte, wherein a ratiometric change in the signal corresponds to the detection of the analyte interacting with the analyte sensor.

One exemplary fusion protein, among others, includes: an optically-active fluorescent host protein in which a molecular recognition motif is operatively linked to or integrated therein that has an amino acid sequence selected from: SEQ ID NO: 1-99.

One exemplary isolated nucleotide, among others, includes: an isolated nucleotide encoding a fusion protein, wherein the fusion protein includes an optically-active fluorescent host protein in which a molecular recognition motif is operatively linked to or integrated therein that has an amino acid sequence selected from: SEQ ID NO:1-99.

One exemplary kit for detecting analyte activity, among others, includes: an analyte sensor of claim 1, related agents that can facilitate the delivery of the protein to its desired destination, and directions.

One exemplary method for characterizing the cellular activity an analyte, among others, includes: expressing an analyte sensor in a cell, wherein the analyte sensor includes the analyte sensor noted above; measuring a signal produced from the analyte sensor; and comparing the signal to a standard signal from the analyte sensor prior to interaction with analyte, wherein a ratiometric change in the signal corresponds to the detection of the analyte interacting with the analyte sensor.

One exemplary vector, among others, includes: a vector encoding a fusion protein, wherein the fusion protein includes an optically-active fluorescent host protein in which a molecular recognition motif is operatively linked to or integrated therein that has an amino acid sequence selected from: SEQ ID NO: 1-99.

One exemplary method of detecting pH change in a system, among others, includes: providing a analyte sensor as provided above; measuring a signal produced from the analyte sensor in the system; and comparing the signal to a standard signal from the analyte sensor prior to interaction with an analyte, wherein a change in the signal corresponds to a change in pH the environment.

One exemplary method of controlling the concentration of an analyte in a cell, among others, includes: introducing a analyte sensor as provided above to the cell, wherein the analyte sensor binds with the analyte.

These embodiments, uses of these embodiments, and other uses, features and advantages of the present disclosure, will become more apparent to those of ordinary skill in the relevant art when the following detailed description of the preferred embodiments is read in conjunction with the appended figures.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

The patent or application file contains at least one drawing executed in color. Copies of this patent or patent application publication with color drawing(s) will be provided by the Office upon request and payment of the necessary fee.

FIG. 1 illustrates a model structure of EGFP-based $Ca^{2+}$ sensors based on 1ema.pdb. All $Ca^{2+}$ sensors are composed of a $Ca^{2+}$ binding motif grafted into enhanced green fluorescent protein (EGFP). FIG. 1A illustrates the domain structure of GFP variants used for expression and imaging experiments. CRsig: calreticulin signal peptide, MLLSVPLLLGLLG-LAAAD; KDEL: ER retention signal; kz: Kozak consensus sequence for optimal translational initiation in mammalian cells. Note that constructs Ca-G1 and Ca-G2 contain the flanking sequences whereas Ca-G1', Ca-G2' and Ca-G3' were designed without flanking sequences. FIG. 1B is the schematic topology of grafting locations Glu172-Asp173 (position 1), Gln157-Lys158 (position 2), and Asn144-Tyr145 (position 3) in EGFP using PyMol v 0.98 (Delano Scientific LLC).

FIG. 2 illustrates the visible absorbance FIG. 2A and fluorescence FIG. 2B spectra of EGFP-wt and its variants. The measurements were performed in 10 mM Tris and 1 mM DTT (pH 7.4). The protein concentrations were 20 μM and 10 μM for absorbance and fluorescence experiments, respectively. The length of the cell was 1 cm. The fluorescence experiments were performed with a slit width of 1 nm for both excitation and emission. $\lambda_{ex}$=398 nm. Symbols of EGFP-wt and its variants in FIG. 2 B is the same as those in FIG. 2A.

FIG. 3A illustrates the visible absorption spectrum for sensor Ca-G1-37 with increasing $Ca^{2+}$ concentrations. $Ca^{2+}$ dependence of fluorescence emission spectra with excitation of $\lambda_{ex}$=398 nm FIG. 3B and $\lambda_{ex}$=490 nm FIG. 3C. Symbols of different $Ca^{2+}$ concentrations in FIG. 3B and FIG. 3C are the same as those in FIG. 3A. The measurements were performed at 17 μM Ca-G1-37 for visible absorption and 1.7 μM Ca-G1-37 for fluorescence experiments with 10 mM Tris and 1 mM DTT (pH 7.4), respectively. The slit width of excitation and emission was 1 and 2 nm, respectively. The arrows indicate the direction of signal change resulting from an increase in the $Ca^{2+}$ concentration. FIG. 3D shows normalized $F_{(398\ nm)}/F_{(490\ nm)}$ ratio curve-fitting of the $Ca^{2+}$ titration data.

FIG. 5A: Stopped-flow traces of fluorescence increase ($\lambda_{ex}$=398 nm) upon rapid mixing of Ca-G1 at a final concentration of 20 μM with $Ca^{2+}$ at different concentrations. FIG. 5B: Observed rates of fluorescence increases as a function of $Ca^{2+}$ concentration. FIG. 5C: Maximal changes in the amplitude of the fluorescence intensities observed in panel A as a function of $Ca^{2+}$ concentration. FIG. 5D: Stopped-flow trace of fluorescence decrease ($\lambda_{ex}$=398 nm) upon rapid mixing of 40 μM Ca-G1 preloaded with 0.8 mM $Ca^{2+}$ with Tris buffer. All measurements were carried out in 10 mM Tris and 1 mM DTT (pH 7.4) at 25° C. A 455 nm long pass filter was used to collect the emission with a main peak at 510 nm. Data were fit to Eqs 6 (FIGS. 5A and 5D), 8 (FIG. 5B) and 2 (FIG. 5C), respectively.

FIG. 14 illustrates Table 1 in Example 1.

FIG. 19 illustrates Table 1 of Example 3.

FIG. 20A-D illustrates embodiments of the present disclosure.

FIG. 22B illustrates curve-fitting of C2-Gd complex to quantify Kd. The Kd for $Gd^{3+}$ was 2.0 μM.

DETAILED DESCRIPTION

Figure 3:
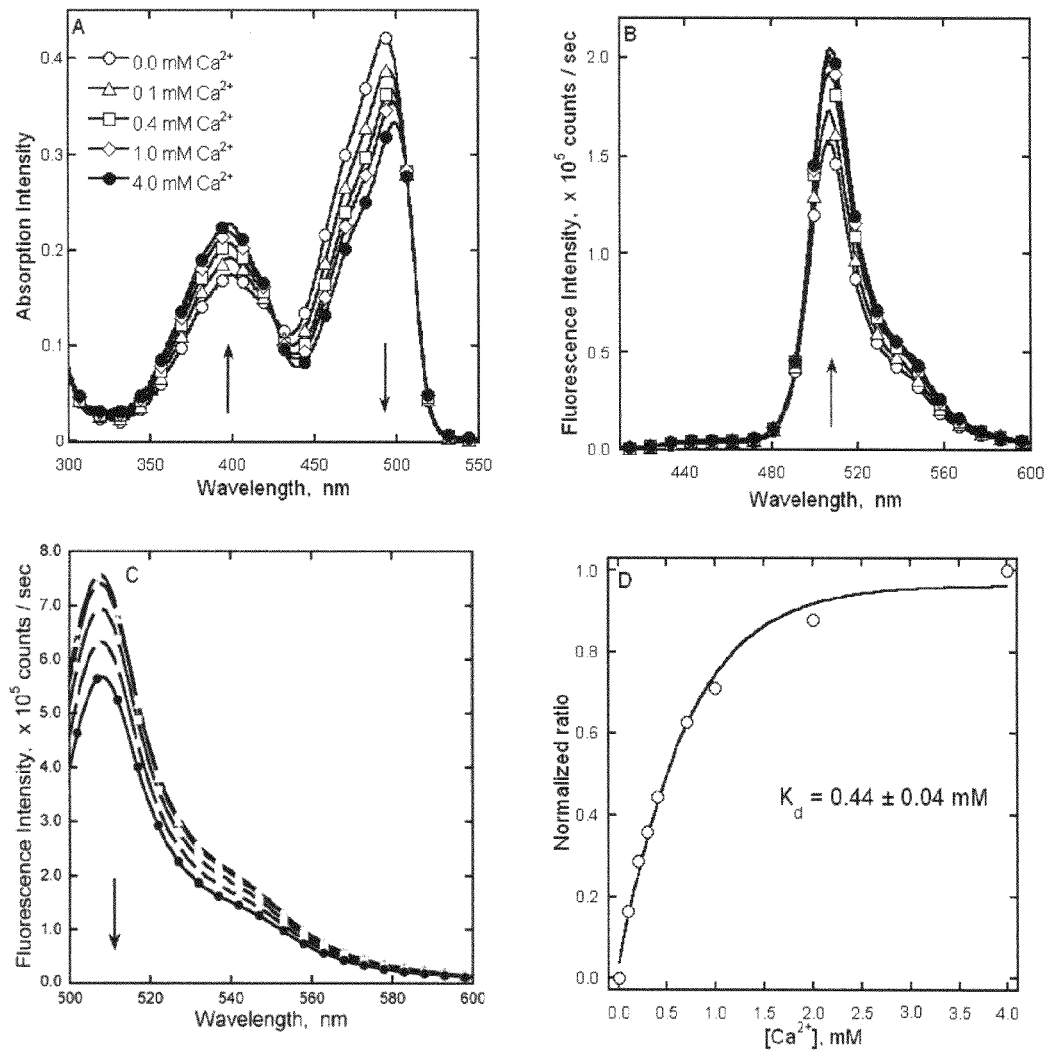
FIG. 3 illustrates the spectroscopic characterization of $Ca^{2+}$ sensor Ca-G1-37.

Embodiments of the present disclosure will employ, unless otherwise indicated, techniques of synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely-utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall (homologous) and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of this disclosure and still result in a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biologically functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073, (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present invention.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution (including conservative and non-conservative substitution), or insertion, and wherein said alterations may occur at the amino- or carboxy-terminus positions of the reference polypeptide sequence or anywhere between those terminal positions, interspersed either individually among the amino acids in the reference sequence, or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-aza-phenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an E. coli S30 extract and commercially-available enzymes and other reagents. Proteins are purified by chromatography. (Robertson, et al., J. Am. Chem. Soc., 113: 2722, 1991; Ellman, et al., Methods Enzymol., 202: 301, 1991; Chung, et al., Science, 259: 806-9, 1993; and Chung, et al., Proc. Natl. Acad. Sci. USA, 90: 10145-9, 1993). In a second method, translation is carried out in Xenopus oocytes by microinjection of mutated mRNA and chemically aminoacylated suppressor tRNAs (Turcatti, et al., J. Biol. Chem., 271: 19991-8, 1996). Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., Biochem., 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al., Protein Sci., 2: 395-403, 1993).

As used herein, the term "polynucleotide" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompass a polynucleotide as defined above.

In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including simple and complex cells, inter alia.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminus positions of the reference nucleotide sequence or anywhere between those terminus positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

As used herein, DNA may obtained by any method. For example, the DNA includes complementary DNA (cDNA) prepared from mRNA, DNA prepared from genomic DNA, DNA prepared by chemical synthesis, DNA obtained by PCR amplification with RNA or DNA as a template, and DNA constructed by appropriately combining these methods.

As used herein, an "isolated nucleic acid" is a nucleic acid, the structure of which is not identical to that of any naturally occurring nucleic acid or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA molecules, transfected cells, or cell clones, e.g., as these occur in a DNA library such as a cDNA or genomic DNA library.

The term "substantially pure" as used herein in reference to a given polypeptide means that the polypeptide is substantially free from other biological macromolecules. For example, the substantially pure polypeptide is at least 75%, 80, 85, 95, or 99% pure by dry weight. Purity can be measured by any appropriate standard method known in the art, for example, by column chromatography, polyacrylamide gel electrophoresis, or HPLC analysis.

The DNA encoding the protein disclosed herein can be prepared by the usual methods: cloning cDNA from mRNA encoding the protein, isolating genomic DNA and splicing it, chemical synthesis, and so on.

cDNA can be cloned from mRNA encoding the protein by, for example, the method described below:

First, the mRNA encoding the protein is prepared from the above-mentioned tissues or cells expressing and producing the protein. mRNA can be prepared by isolating total RNA by a known method such as guanidine-thiocyanate method (Chirgwin et al., Biochemistry, 18:5294, 1979), hot phenol method, or AGPC method, and subjecting it to affinity chromatography using oligo-dT cellulose or poly-U Sepharose.

Then, with the mRNA obtained as a template, cDNA is synthesized, for example, by a well-known method using reverse transcriptase, such as the method of Okayama et al (Mol. Cell. Biol. 2:161 (1982); Mol. Cell. Biol. 3:280 (1983)) or the method of Hoffman et al. (Gene 25:263 (1983)), and converted into double-stranded cDNA. A cDNA library is prepared by transforming $E.$ $coli$ with plasmid vectors, phage vectors, or cosmid vectors having this cDNA or by transfecting $E.$ $coli$ after in vitro packaging.

The plasmid vectors used herein are not limited as long as they are replicated and maintained in hosts. Any phage vector that can be replicated in hosts can also be used. Examples of commonly used cloning vectors are pUC19, .lambda.gt10, .lambda.gt11, and so on. When the vector is applied to immunological screening as mentioned below, a vector having a promoter that can express a gene encoding the desired protein in a host is preferably used.

cDNA can be inserted into a plasmid by, for example, the method of Maniatis et al. (Molecular Cloning, A Laboratory Manual, second edition, Cold Spring Harbor Laboratory, p. 1.53, 1989). cDNA can be inserted into a phage vector by, for example, the method of Hyunh et al. (DNA cloning, a practical approach, 1, p. 49 (1985)). These methods can be simply performed by using a commercially available cloning kit (for example, a product from Takara Shuzo). The recombinant plasmid or phage vector thus obtained is introduced into an appropriate host cell such as a prokaryote (for example, $E.$ $coli$: HB101, DH5a, MC1061/P3, etc).

Examples of a method for introducing a plasmid into a host are, calcium chloride method, calcium chloride/rubidium chloride method, lipidsome method, and electroporation method, described in Molecular Cloning, A Laboratory Manual (second edition, Cold Spring Harbor Laboratory, p. 1.74 (1989)). Phage vectors can be introduced into host cells by, for example, a method in which the phage DNAs are introduced into grown hosts after in vitro packaging. In vitro packaging can be easily performed with a commercially available in vitro packaging kit (for example, a product from Stratagene or Amersham).

The identification of cDNA encoding protein, its expression being augmented depending on the stimulation of cytokines like AID protein disclosed herein, can be carried out by for example suppression subtract hybridization (SSH) (Proc. Natl. Acad. Sci. USA, 93:6025-6030, 1996; Anal. Biochem., 240:90-97, 1996) taking advantage of suppressive PCR effect (Nucleic Acids Res., 23:1087-1088, 1995), using two cDNA libraries, namely, cDNA library constructed from mRNA derived from stimulated cells (tester cDNA library) and that constructed from mRNA derived from unstimulated cells (driver cDNA library).

Embodiments of the present disclosure relate to a recombinant vector comprising the DNA encoding the protein used herein. As a recombinant vector disclosed herein, any vector can be used as long as it is capable of retaining replication or self-multiplication in each host cell of prokaryotic and/or eukaryotic cells, including plasmid vectors and phage vectors. The recombinant vector can easily be prepared by ligating the DNA encoding protein with a vector for recombination available in the art (plasmid DNA and bacteriophage DNA) by the usual method.

Specific examples of the vectors for recombination used are $E.$ $coli$-derived plasmids such as pBR322, pBR325, pUC12, pUC13, and pUC19, yeast-derived plasmids such as pSH19 and pSH15, and $Bacillus$ $subtilis$-derived plasmids such as pUB110, pTP5, and pC194. Examples of phages are a bacteriophage such as lambda phage, and an animal or insect virus (pVL1393, Invitrogen) such as a retrovirus, vaccinia virus, and nuclear polyhedrosis virus.

An "expression vector" is useful for expressing the DNA encoding the protein used herein and for producing the protein. The expression vector is not limited as long as it expresses the gene encoding the protein in various prokaryotic and/or eukaryotic host cells and produces this protein. Examples thereof are pMAL C2, pEF-BOS (Nucleic Acids Res. 18:5322 (1990) and so on), pME18S, $_p$cDNA (Experimental Medicine: SUPPLEMENT, "Handbook of Genetic Engineering" (1992)), etc.

When bacteria, particularly $E.$ $coli$ are used as host cells, an expression vector generally comprises, at least, a promoter/operator region, an initiation codon, the DNA encoding the protein termination codon, terminator region, and replicon.

When yeast, animal cells, or insect cells are used as hosts, an expression vector is preferably comprised of, at least; a promoter, an initiation codon, the DNA encoding the protein and a termination codon. It may also comprise the DNA encoding a signal peptide, enhancer sequence, 5'- and 3'-untranslated region of the gene encoding the protein, splicing junctions, polyadenylation site, selectable marker region, and replicon. The expression vector may also contain, if required, a gene for gene amplification (marker) that is usually used. DNA plasmids can also be directly introduced to the mammalian cells of animals to express proteins.

A promoter/operator region to express the protein in bacteria comprises a promoter, an operator, and a Shine-Dalgarno (SD) sequence (for example, AAGG). For example, when the host is *Escherichia*, it preferably comprises Trp promoter, lac promoter, recA promoter, lambda.PL promoter, b 1 pp promoter, tac promoter, or the like. Examples of a promoter to express the protein in yeast are PH05 promoter, PGK promoter, GAP promoter, ADH promoter, and so on. When the host is *Bacillus*, examples thereof are SL01 promoter, SP02 promoter, penP promoter, and so on. When the host is a eukaryotic cell such as a mammalian cell, examples thereof are SV40-derived promoter, retrovirus promoter, heat shock promoter, and so on, and preferably SV-40 and retrovirus-derived one. As a matter of course, the promoter is not limited to the above examples. In addition, using an enhancer is effective for expression.

A preferable initiation codon is, for example, a methionine codon (ATG).

A commonly used termination codon (for example, TAG, TAA, TGA) is exemplified as a termination codon. Usually, used natural or synthetic terminators are used as a terminator region.

A "replicon" means a DNA capable of replicating the whole DNA sequence in host cells, and includes a natural plasmid, an artificially modified plasmid (DNA fragment prepared from a natural plasmid), a synthetic plasmid, and so on. Examples of preferable plasmids are pBR322 or its artificial derivatives (DNA fragment obtained by treating pBR322 or $_p$RSET with appropriate restriction enzymes) for *E. coli*, yeast 2.mu. plasmid or yeast chromosomal DNA for yeast, and pRSVneo ATCC 37198, pSV2dhfr ATCC 37145, pdBPV-MMTneo ATCC 37224, pSV2neo ATCC 37149, and such for mammalian cells.

An enhancer sequence, polyadenylation site, and splicing junction that are usually used in the art, such as those derived from SV40 can also be used.

A selectable marker usually employed can be used according to the usual method. Examples thereof are resistance genes for antibiotics, such as tetracycline, ampicillin, or kanamycin.

Examples of genes for gene amplification are dihydrofolate reductase (DHFR) gene, thymidine kinase gene, neomycin resistance gene, glutamate synthase gene, adenosine deaminase gene, ornithine decarboxylase gene, hygromycin-B-phosphotransferase gene, aspartate transcarbamylase gene, etc.

The expression vector used herein can be prepared by continuously and circularly linking at least the above-mentioned promoter, initiation codon, DNA encoding the protein, termination codon, and terminator region, to an appropriate replicon. If desired, appropriate DNA fragments (for example, linkers, restriction sites, and so on), can be used by the usual method such as digestion with a restriction enzyme or ligation using T4 DNA ligase.

Affinity tags such His-tag and GST can be added at the sequence end to facilitate protein purification and recognition by Western blot and pulldown assay. Examples of other tags such as HA and FLAG can also be added to allow further manipulation of the constructs.

As used herein, "transformants" can be prepared by introducing the expression vector mentioned above into host cells.

As used herein, "host" cells are not limited as long as they are compatible with an expression vector mentioned above and can be transformed. Examples thereof are various cells such as wild-type cells or artificially established recombinant cells usually used in technical field (for example, bacteria (*Escherichia* and *Bacillus*), yeast (*Saccharomyces, Pichia*, and such), animal cells, or insect cells).

*E. coli* or animal cells are preferably used. Specific examples are *E. coli* (DH5 alpha, TB1, HB101, and such), mouse-derived cells (COP, L, C127, Sp2/0, NS-1, NIH 3T3, and such), rat-derived cells (PC12, PC12h), hamster-derived cells (BHK, CHO, and such), monkey-derived cells (COS1, COS3, COS7, CV1, Velo, and such), and human-derived cells (Hela, diploid fibroblast-derived cells, myeloma cells, and HepG2, and such).

An expression vector can be introduced (transformed (transfected)) into host cells by known methods.

Transformation can be performed, for example, according to the method of Cohen et al. (Proc. Natl. Acad. Sci. USA, 69:2110 (1972)), protoplast method (Mol, Gen. Genet., 168: 111 (1979)), or competent method (J. Mol. Biol., 56:209 (1971)) when the hosts are bacteria (*E. coli, Bacillus subtilis*, and such), the method of Hinnen et al. (Proc. Natl. Acad. Sci. USA, 75:1927 (1978)), or lithium method (J. Bacteriol., 153: 163 (1983)) when the host is *Saccharomyces cerevisiae*, the method of Graham (Virology, 52:456 (1973)) when the hosts are animal cells, and the method of Summers et al. (Mol. Cell. Biol., 3:2156-2165 (1983)) when the hosts are insect cells.

The protein disclosed herein, can be produced by cultivating transformants (in the following, this term includes transfectants) comprising an expression vector prepared as mentioned above in nutrient media.

The nutrient media preferably comprise a carbon source, an inorganic or organic nitrogen source necessary for the growth of host cells (transformants). Examples of the carbon source are glucose, dextran, soluble starch, and sucrose, and examples of the inorganic or organic nitrogen source are ammonium salts, nitrates, amino acids, corn steep liquor, peptone, casein, meat extract, soy bean cake, and potato extract. If desired, they may comprise other nutrients (for example, an inorganic salt (for example, calcium chloride, sodium dihydrogenphosphate, and magnesium chloride), vitamins, antibiotics (for example, tetracycline, neomycin, ampicillin, kanamycin, and so on).

Cultivation of cell lines is performed by a method known in the art. Cultivation conditions such as temperature, pH of the media, and cultivation time are selected appropriately so that the protein is produced in large quantities.

Examples of the isolation and purification method are a method utilizing solubility, such as salting out and solvent precipitation method; a method utilizing the difference in molecular weight, such as dialysis, ultrafiltration, gel filtration, and sodium dodecyl sulfate-polyacrylamide gel electrophoresis; a method utilizing charges, such as ion exchange chromatography and hydroxylapatite chromatography; a method utilizing specific affinity, such as affinity column chromatography; a method utilizing the difference in hydrophobicity, such as reverse phase high performance liquid chromatography; and a method utilizing the difference in isoelectric point, such as isoelectric focusing.

Furthermore, unless the context demands otherwise, the term peptide, polypeptide and protein are used interchangeably to refer to amino acids in which the amino acid residues are linked by covalent peptide bonds or alternatively (where post-translational processing has removed an internal segment) by covalent di-sulphide bonds, etc. The amino acid chains can be of any length and comprise at least two amino acids, they can include domains of proteins or full-length proteins. Unless otherwise stated the terms, peptide, polypeptide and protein also encompass various modified forms thereof, including but not limited to glycosylated forms, phosphorylated forms etc.

It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including simple and complex cells, inter alia.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminus positions of the reference nucleotide sequence or anywhere between those terminus positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

The term "codon" means a specific triplet of mononucleotides in the DNA chain or mRNA that make up an amino acid or termination signal.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (e.g., GAU and GAC triplets each encode Asp).

As used herein, the term "exogenous DNA" or "exogenous nucleic acid sequence" or "exogenous polynucleotide" refers to a nucleic acid sequence that was introduced into a cell or organelle from an external source. Typically the introduced exogenous sequence is a recombinant sequence.

As used herein, the term "transfection" refers to the introduction of a nucleic acid sequence into the interior of a membrane enclosed space of a living cell, including introduction of the nucleic acid sequence into the cytosol of a cell as well as the interior space of a mitochondria, nucleus or chloroplast. The nucleic acid may be in the form of naked DNA or RNA, associated with various proteins, or the nucleic acid may be incorporated into a vector.

As used herein, the term "vector" or "expression vector" is used to denote a DNA molecule, linear or circular, which includes a segment encoding a polypeptide of interest operably linked to additional segments that provide for its transcription and translation upon introduction into a host cell or host cell organelles. Such additional segments include promoter and terminator sequences, and may also include one or more origins of replication, one or more selectable markers, an enhancer, a polyadenylation signal, etc. Expression vectors are generally derived from yeast or bacterial genome or plasmid DNA, animal virus genome, or viral DNA, or may contain elements of both.

"DNA regulatory sequences", as used herein, are transcriptional and translational control sequences, such as promoters, enhancers, polyadenylation signals, termination signals, and the like, that provide for and/or regulate expression of a coding sequence in a host cell.

A "promoter sequence" is a DNA regulatory region in an operon capable of binding RNA polymerase in a cell and initiating transcription of a downstream (3' direction) coding sequence. The promoter sequence is bound at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present disclosure.

The terms "chimeric", "fusion" and "composite" are used to denote a protein, peptide domain or nucleotide sequence or molecule containing at least two component portions that are mutually heterologous in the sense that they are not, otherwise, found directly (covalently) linked in nature. More specifically, the component portions are not found in the same continuous polypeptide or gene in nature, at least not in the same order or orientation or with the same spacing present in the chimeric protein or composite domain. Such materials contain components derived from at least two different proteins or genes or from at least two non-adjacent portions of the same protein or gene. Composite proteins, and DNA sequences that encode them, are recombinant in the sense that they contain at least two constituent portions that are not otherwise found directly linked (covalently) together in nature.

The term "domain" in this context is not intended to be limited to a single discrete folding domain.

A "reporter polynucleotide" includes any gene that expresses a detectable gene product, which may be RNA or a reporter polypeptide. Reporter genes include coding sequences for which the transcriptional and/or translational products are readily detectable or selectable.

An "insertion" or "addition", as used herein, refers to a change in an amino acid or nucleotide sequence resulting in the addition or insertion of one or more amino acid or nucleotide residues, respectively, as compared to the corresponding naturally occurring molecule.

A "deletion" or "subtraction", as used herein, refers to a change in an amino acid or nucleotide sequence resulting in the deletion or subtraction of one or more amino acid or nucleotide residues, respectively, as compared to the corresponding naturally occurring molecule.

A "substitution", as used herein, refers to the replacement of one or more amino acids or nucleotides by different amino acids or nucleotides, respectively.

A "mutation" is an inheritable change in a DNA sequence relative to a reference "wild-type" DNA sequence. Mutations can occur as a result of a single base change, multiple base changes, or the addition or deletion of more than one nucleotide to a DNA sequence.

The term "genotoxicity" is used to broadly refer to any deleterious change in the genetic material of a cell, regardless of the mechanism by which the change is induced.

As used herein the term mutagenicity and genotoxic activity are used to refer to the ability of an agent (e.g., a chemical compound or a drug candidate) to cause a permanent change in the structure of the genetic material of a cell which causes a heritable change in the effected cell. Contemplated changes include alterations in the sequences of the bases in the nucleic acid (gene mutation), structural changes to chromosomes (clastogenicity) and/or changes to the number of chromosomes present.

A "mutagen" or a "genotoxic agent" is an agent that creates or causes mutations. It is well-established that chemical mutagens vary in their modes of action. However, in general terms, a chemical mutagen changes a nucleic acid or nucleoside relative to the nucleotide sequence of a reference or "wild-type" genome. Generally speaking a mutagen or genotoxic agent increases the frequency of reversion or forward mutation.

The term "mutant" is employed broadly to refer to a protein that differs in some way from a reference wild-type protein, where the protein may retain biological properties of the reference wild-type (e.g., naturally occurring) protein, or may have biological properties that differ from the reference wild-type protein. The term "biological property" of the subject proteins includes, but is not limited to, spectral properties, such as emission maximum, quantum yield, and brightness, and the like; in vivo and/or in vitro stability (e.g., half-life); and the like. Mutants can include single amino acid changes (point mutations), deletions of one or more amino acids (point-deletions), N-terminal truncations, C-terminal truncations, insertions, and the like. Mutants can be generated using standard techniques of molecular biology.

A "gene mutation" refers to a mutation that occurs entirely within one gene, or its upstream regulatory sequences and can comprise either a point mutation or other disruption of normal chromosomal structure that occurs entirely within one gene.

A "reversion assay" is an assay of genotoxic activity that detects a reverse mutation which confers normal function to a mutant gene thereby causing a gain of function. Typically, the genotoxic activity of compounds are evaluated using a bacterial reverse mutation assay that utilizes an amino acid-requiring (i.e., auxotrophic) tester strains of *Salmonella typhimurium* (*S. typhimurium*) or *Escherichia coli* (*E. coli*) to evaluate the genotoxic activity of a compound. Generally speaking, reversion assays are capable of detecting point mutations, such as a substitution, an addition or a deletion of one or more DNA bases, which are introduced into the genome of an affected tester strain.

A "forward mutation assay" is an assay of genotoxic activity which detects "forward" mutations that alter a functional gene in a way that causes a loss, rather than a gain, of function.

A "wild-type" strain is capable of a full range of metabolic activities. For example, wild-type strains of *Salmonella* can synthesize all 20 amino acids from a single carbon source.

A "mutant" strain is not capable of all of the activities of the wild-type strain from which it is derived. For example, a mutant bacterial strain that is defective in its ability to synthesize the amino acid histidine (his strain) requires the presence of exogenous histidine in order to grow.

A "point mutation" is a change in one, or a small number of base pairs, in a DNA sequence. Point mutations may result from base pair substitutions or from small insertions or deletions.

A "transition" is a point mutation in which a purine is replaced with a purine or a pyrimidine is replaced with a pyrimidine.

A "transversion" is a point mutation in which a purine is replaced with a pyrimidine or a pyrimidine with a purine. Generally speaking, transitions are more common than transversions because the former are not detected by the proofreading enzymes.

Alternatively, point mutation can also cause a nonsense mutation resulting from the insertion of a stop codon (amber, ochre, opal). Base pair mutations that generate a translation stop codon causes premature termination of translation of the coded protein.

A "frameshift mutation" results from the insertion or deletion of one or more nucleotides within a gene. The "reading frame" of a gene refers to the order of the bases with respect to the starting point for translation of the mRNA. Deletion of a single base pair results in moving ahead one base in all of the codons, and is often referred to as a positive frameshift. Addition of one base pair (or loss of two base pairs) shifts the reading frame behind by one base, and is often referred to as a negative frameshift.

As used herein the term "DNA Repair Mechanism" refers to any one of the potential repair mechanisms that exist in both prokaryotes and eukaryotes. For example: postreplication; mismatch repair; nucleotide excision-repair and photoreactivation or light-dependent repair (not found in mammals).

A "base pair substitution mutagen" is an agent that causes a base (i.e., nucleotide) change in DNA. In the context of a reversion test this change may occur at the site of the original mutation, or at a second site in the bacterial genome.

A "frameshift mutagen" is an agent that causes the addition or deletion of one or more base pairs in the DNA, thus changing the reading frame in the RNA.

As used herein, the term "hybridization" refers to the process of association of two nucleic acid strands to form an antiparallel duplex stabilized by means of hydrogen bonding between residues of the opposite nucleic acid strands.

"Hybridizing" and "binding", with respect to polynucleotides, are used interchangeably. The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

In accordance with the present disclosure, "a detectably effective amount" of the sensor of the present disclosure is defined as an amount sufficient to yield an acceptable image using equipment that is available for clinical use. A detectably effective amount of the sensor of the present disclosure may be administered in more than one injection. The detectably effective amount of the sensor of the present disclosure can vary according to factors such as the degree of susceptibility of the individual, the age, sex, and weight of the individual, idiosyncratic responses of the individual, the dosimetry, and the like. Detectably effective amounts of the sensor of the present disclosure can also vary according to instrument and film-related factors. Optimization of such factors is well within the level of skill in the art.

By "administration" is meant introducing a sensor of the present disclosure into a subject. The preferred route of administration of the sensor is intravenous. However, any route of administration, such as oral, topical, subcutaneous, peritoneal, intraarterial, inhalation, vaginal, rectal, nasal, introduction into the cerebrospinal fluid, or instillation into body compartments can be used.

In accordance with the present disclosure, "a detectably effective amount" of the sensor of the present disclosure is defined as an amount sufficient to yield an acceptable image using equipment that is available for clinical use. A detectably effective amount of the sensor of the present disclosure may be administered in more than one injection. The detectably effective amount of the sensor of the present disclosure can vary according to factors such as the degree of susceptibility of the individual, the age, sex, and weight of the individual, idiosyncratic responses of the individual, the dosimetry, and the like. Detectably effective amounts of the sensor of the present disclosure can also vary according to instrument and film-related factors. Optimization of such factors is well within the level of skill in the art.

As used herein the term "isolated" is meant to describe a polynucleotide, a polypeptide, an antibody, or a host cell that is in an environment different from that in which the polynucleotide, the polypeptide, the antibody, or the host cell naturally occurs.

"Fluorescent protein" refers to any protein capable of emitting light when excited with appropriate electromagnetic radiation. Fluorescent proteins include proteins having amino acid sequences that are either natural or engineered, such as the fluorescent proteins derived from *Aequorea*-related fluorescent proteins.

A "fluorescent protein" as used herein is an *Aequorea victoria* green fluorescent protein (GFP), structural variants of GFP (i.e., circular permutants, monomeric versions), folding variants of GFP (i.e., more soluble versions, superfolder versions), spectral variants of GFP (i.e., YFP, CFP), and GFP-like fluorescent proteins (i.e., DsRed and mcherry). Fluorescent proteins can be from different resources. For class Hydrozoa, GFP can be from *Aequorea victoria, Mitrocoma* (synonym Halistaura), *Obelia, Phialidium* etc. For class Anthozoa, GFP can be from *Acanthopilum, Cavernularia, Renilla, Ptilosarcus* and *Pennatula, Stylatula*, etc. we also have GFP-like proteins from *Anemonia majna*, FP595 from *Anemonia sulcata*, FPs from *Zoanthus*, etc. The term "GFP-like fluorescent protein" is used to refer to members of the Anthozoa fluorescent proteins sharing the 11-beta strand "barrel" structure of GFP, as well as structural, folding and spectral variants thereof. The terms "GFP-like non-fluorescent protein" and "GFP-like chromophoric protein" (or, simply, "chromophoric protein" or "chromoprotein") are used to refer to the Anthozoa and Hydrozoa chromophoric proteins sharing the 11-beta strand "barrel" structure of GFP, as well as structural, folding and spectral variants thereof. GFP-like proteins all share common structural and functional characteristics, including without limitation, the capacity to form internal chromophores without requiring accessory co-factors, external enzymatic catalysis or substrates, other than molecular oxygen.

A variety of fluorescent proteins may be used in the present disclosure, including proteins that fluoresce due to intramolecular rearrangements or the addition of cofactors that promote fluorescence. For example, green fluorescent proteins of cnidarians, which act as their energy-transfer acceptors in bioluminescence, are suitable fluorescent proteins for use in the fluorescent indicators. A green fluorescent protein ("GFP") is a protein that emits green light, and a blue fluorescent protein ("BFP") is a protein that emits blue light. GFPs have been isolated from the Pacific Northwest jellyfish, *Aequorea victoria*, the sea pansy, *Renilla reniformis*, and *Phialidium gregarium* (see Ward, W. W., et al., Photochem. Photobiol., 35:803-808 (1982); and Levine, L. D., et al., Comp. Biochem. Physiol., 72B:77-85 (1982)).

A variety of *Aequorea*-related GFPs having useful excitation and emission spectra have been engineered by modifying the amino acid sequence of a naturally occurring GFP from *Aequorea victoria*. See Prasher, D. C., et. al., Gene, 111:229-233 (1992); Heim, R., et al., Proc. Natl. Acad. Sci., USA, 91:12501-04 (1994); U.S. Ser. No. 08/337,915, filed Nov. 10, 1994; International application PCT/US95/14692, filed Nov. 10, 1995; and U.S. Ser. No. 08/706,408, filed Aug. 30, 1996. The cDNA of GFP can be concatenated with those encoding many other proteins; the resulting fusions often are fluorescent and retain the biochemical features of the partner proteins. See, Cubitt, A. B., et al., Trends Biochem. Sci. 20:448-455 (1995). Mutagenesis studies have produced GFP mutants with shifted wavelengths of excitation or emission. See, Heim, R. & Tsien, R. Y. Current Biol. 6:178-182 (1996). Suitable pairs, for example a blue-shifted GFP mutant P4-3 (Y66H/Y145F) and an improved green mutant S65T can respectively serve as a donor and an acceptor for fluorescence resonance energy transfer (FRET). See, Tsien, R. Y., et al., Trends Cell Biol. 3:242-245 (1993). A fluorescent protein is an *Aequorea*-related fluorescent protein if any contiguous sequence of 150 amino acids of the fluorescent protein has at least 85% sequence identity with an amino acid sequence, either contiguous or non-contiguous, from the wild type *Aequorea* green fluorescent protein. More preferably, a fluorescent protein is an *Aequorea*-related fluorescent protein if any contiguous sequence of 200 amino acids of the fluorescent protein has at least 95% sequence identity with an amino acid sequence, either contiguous or non-contiguous, from the wild type *Aequorea* green fluorescent protein. Similarly, the fluorescent protein can be related to *Renilla* or *Phialidium* wild-type fluorescent proteins using the same standards.

A variant of GFP with two mutations at F64L and S65 used in embodiments of the present disclosure includes enhanced green fluorescent protein (EGFP) (SEQ ID NO: 119). Its chromophore has an excitation maximum at 488 nm and emission maxima at 510 nm. Its fluorescent signal is significantly greater than that of w.t. GFP without these two mutations.

Another variant of GFP is called Cycle 3 (Patternson et al., 19967; Ward, 1997, which is included herein by reference). This GFP variant with mutations at F99S, M153T and V163A at w.t. GFP has improved folding and chromophore formation at 37° C. or above.

Other fluorescent proteins can be used in the fluorescent indicators, such as, for example, yellow fluorescent protein from *Vibrio fischeri* strain Y-1, Peridinin-chlorophyll a binding protein from the dinoflagellate *Symbiodinium* sp. phycobiliproteins from marine cyanobacteria such as *Synechococcus*, e.g., *phycoerythrin* and *phycocyanin*, or oat phytochromes from oat reconstructed with phycoerythrobilin. These fluorescent proteins have been described in Baldwin, T. O., et al., Biochemistry 29:5509-5515 (1990), Morris, B. J., et al., Plant Molecular Biology, 24:673-677 (1994), and Wilbanks, S. M., et al., J. Biol. Chem. 268:1226-1235 (1993), and Li et al., Biochemistry 34:7923-7930 (1995).

The term "link" as used herein refers to a physical linkage as well as linkage that occurs by virtue of co-existence within a biological particle, e.g., phage, bacteria, yeast or other eukaryotic cell.

The construction of expression vectors and the expression of genes in transfected cells involves the use of molecular cloning techniques also well known in the art. Sambrook et al., Molecular Cloning—A Laboratory Manual, Cold Spring Harbor Laboratory, Cold Spring Harbor, N.Y., (1989) and Current Protocols in Molecular Biology, F. M. Ausubel et al., eds., (Current Protocols, a joint venture between Greene Publishing Associates, Inc. and John Wiley & Sons, Inc., most recent Supplement).

Nucleic acids used to transfect cells with sequences coding for expression of the polypeptide of interest generally will be in the form of an expression vector including expression control sequences operatively linked to a nucleotide sequence coding for expression of the polypeptide. As used, the term "nucleotide sequence coding for expression of" a polypeptide refers to a sequence that, upon transcription and translation of mRNA, produces the polypeptide. This can include sequences containing, e.g., introns. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Methods that are well known to those skilled in the art can be used to construct expression vectors containing the fluorescent indicator coding sequence and appropriate transcriptional/translational control signals. These methods include in vitro recombinant DNA techniques, synthetic techniques and in vivo recombination/genetic recombination. (See, for example, the techniques described in Maniatis, et al., Molecular Cloning A Laboratory Manual, Cold Spring Harbor Laboratory, N.Y., 1989).

Transformation of a host cell with recombinant DNA may be carried out by conventional techniques as are well known to those skilled in the art. Where the host is prokaryotic, such as E. coli, competent cells that are capable of DNA uptake can be prepared from cells harvested after exponential growth phase and subsequently treated by the $CaCl_2$ method by procedures well known in the art. Alternatively, $MgCl_2$ or $RbCl_2$ can be used. Transformation can also be performed after forming a protoplast of the host cell or by electroporation as well as by lipidsomes.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the calcium sensing system of the present disclosure, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Preferably, a eukaryotic host is utilized as the host cell as described herein.

Techniques for the isolation and purification of either microbially or eukaryotically expressed polypeptides of the embodiments of the present disclosure may be by any conventional means such as, for example, preparative chromatographic separations and immunological separations such as those involving the use of monoclonal or polyclonal antibodies or antigen.

A variety of host-expression vector systems may be utilized to express the bioluminescent indicator coding sequence. These include, but are not limited to, microorganisms such as bacteria transformed with recombinant bacteriophage DNA, plasmid DNA or cosmid DNA expression vectors containing the calcium sensing system sequences; yeast transformed with recombinant yeast expression vectors containing the calcium sensing system sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid vectors containing the calcium sensing system sequences; insect cell systems infected with recombinant virus expression vectors (e.g., baculovirus) vectors containing the calcium sensing system sequences; or animal cell systems infected with recombinant virus expression vectors (e.g., retroviruses, adenovirus, vaccinia virus vectors containing the calcium sensing system sequences, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (See, e.g., Bitter, et al., Methods in Enzymology 153:516-544, 1987). For example, when cloning in bacterial systems, inducible promoters such as pL of bacteriophage lamda, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted fluorescent indicator coding sequence.

In bacterial systems a number of expression vectors may be advantageously selected depending upon the use intended for calcium sensing system.

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., Expression and Secretion Vectors for Yeast, in Methods in Enzymology, Eds. Wu & Grossman, 31987, Acad. Press, N.Y., Vol. 153, pp. 516-544, 1987; Glover, DNA Cloning, Vol. II, IRL Press, Wash., D.C., Ch. 3, 1986; and Bitter, Heterologous Gene Expression in Yeast, Methods in Enzymology, Eds. Berger & Kimmel, Acad. Press, N.Y., Vol. 152, pp. 673-684, 1987; and The Molecular Biology of the Yeast *Saccharomyces*, Eds. Strathem et al., Cold Spring Harbor Press, Vols. I and II, 1982. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, IRL Press, Wash., D.C., 1986). Alternatively, vectors may be used which promote integration of foreign DNA sequences into the yeast chromosome.

In cases where plant expression vectors are used, the mutation assay system may be driven by any of a number of promoters. For example, viral promoters such as the 35S RNA and 19S RNA promoters of CaMV (Brisson, et al., Nature 310:511-514, 1984), or the coat protein promoter to TMV (Takamatsu, et al., EMBO J. 6:307-311, 1987) may be used; alternatively, plant promoters such as the small subunit of RUBISCO (Coruzzi, et al., 1984, EMBO J. 3:1671-1680; Broglie, et al., Science 224:838-843, 1984); or heat shock promoters, e.g., soybean hsp17.5-E or hsp17.3-B (Gurley, et al., Mol. Cell. Biol. 6:559-565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, Methods for Plant Molecular Biology, Academic Press; N.Y., Section VIII, pp. 421-463, 1988; and Grierson & Corey, Plant Molecular Biology, 2d Ed., Blackie, London, Ch. 7-9, 1988.

An alternative expression system, which could be used to express mutation assay system, is an insect system. In one such system, *Autographa californica* nuclear polyhedrosis virus (AcNPV) is used as a vector to express foreign genes. The virus grows in *Spodoptera frugiperda* cells. The calcium sensing system sequences may be cloned into non-essential regions (for example, the polyhedrin gene) of the virus and placed under control of an AcNPV promoter (for example the polyhedrin promoter). Successful insertion of the calcium sensing system sequences will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith, et al., J. Viol. 46:584, 1983; Smith, U.S. Pat. No. 4,215,051.

DNA sequences encoding the mutation assay system of the present disclosure can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

"Physical linkage" refers to any method known in the art for functionally connecting two molecules (which are termed "physically linked"), including without limitation, recombinant fusion with or without intervening domains, intein-mediated fusion, non-covalent association, covalent bonding (e.g., disulfide bonding and other covalent bonding), hydrogen bonding; electrostatic bonding; and conformational bonding, e.g., antibody-antigen, and biotin-avidin associations.

"Fused" refers to linkage by covalent bonding.

As used herein, "linker" or "spacer" refers to a molecule or group of molecules that connects two molecules, such as a fluorescent binding ligand and a display protein or nucleic acid, and serves to place the two molecules in a preferred configuration.

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence that is transcribed into DNA and then incorporated into the genome. The transgenes used herein include DNA sequences that encode the fluorescent indicator that may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. As used herein, the term "transgenic" includes any transgenic technology familiar to those in the art which can produce an organism carrying an introduced transgene or one in which an endogenous gene has been rendered non-functional or "knocked out."

A "zymogen" or "proenzyme" is an inactive enzyme precursor. A zymogen requires a biochemical change (e.g., such as a hydrolysis reaction revealing the active site, or changing the configuration to reveal the active site) for it to become an active enzyme. In an embodiment, the biochemical change usually occurs in a lysosome where a specific part of the precursor enzyme is cleaved in order to activate it. The amino acid chain that is released upon activation is called the activation peptide.

As used herein, the term "organelle" refers to cellular membrane-bound structures such as the chloroplast, mitochondrion, and nucleus. The term "organelle" includes natural and synthetic organelles.

As used herein, the term "non-nuclear organelle" refers to any cellular membrane bound structure present in a cell, except the nucleus.

As used herein, the term "host" or "organism" includes humans, mammals (e.g., cats, dogs, horses, etc.), living cells, and other living organisms. A living organism can be as simple as, for example, a single eukaryotic cell or as complex as a mammal. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications.

The term "system" can include a host and a non-host. The non-host includes hosts not described above. For example, a non-host can include a solution in a container (e.g, test tube, beaker, and the like).

"Analytes" are atoms, molecules or ions that can bind to proteins or peptides. An analyte may bind reversibly or irreversibly and such a bond may be covalent or non-covalent. While $Ca^{2+}$, $Ln^{3+}$ and $Pb^{2+}$ are used in preferred embodiments of this disclosure as an exemplary analyte, it is understood that analytes suitable with this disclosure include, but are not limited to, metal ions including Group IIA metal ions, transition metal ions, and Lanthanide Series ions.

"Analytes" can also be $H^+$ or $OH^-$ that can bind to the proteins to change the optical properties of the sensors. "Binding site" refers to any section of a peptide or protein involved in forming bonds with an analyte.

"Binding motif" is part of a binding site, often in a larger protein. The term binding site may be used interchangeably with the term binding motif and vice versa.

"Chemical reactions" can include the formation or dissociation of ionic, covalent, or noncovalent structures through known means. Chemical reactions can include changes in environmental conditions such as pH, ionic strength, and temperature.

"Conformation" is the three-dimensional arrangement of the primary, secondary, and tertiary structures of a molecule, and in some instances the quaternary structure of a molecule, including side groups in the molecule; a change in conformation occurs when the three-dimensional structure of a molecule changes. A conformational change may be a shift from an alpha-helix to a beta-sheet or a shift from a beta-sheet to an alpha-helix.

"Detectable changes" or "responsiveness" means any response of a protein to its microenvironment. Such detectable changes or responsiveness may be a small change or shift in the orientation of an amino acid or peptide fragment of the sensor polypeptide as well as, for example, a change in the primary, secondary, or tertiary structure of a polypeptide, and in some instances the quaternary structure of a polypeptide, including changes in protonation, electrical and chemical potential and or conformation.

A "measurable difference" in any fluorescent properties between the active and inactive states suffices for the utility of the fluorescent protein substrates of the disclosure in assays for activity. A measurable difference can be determined by measuring the amount of any quantitative fluorescent property, e.g., the fluorescence signal at a particular wavelength or the integral of fluorescence over the emission spectrum.

"Operatively inserted" or "linked" refers to a juxtaposition wherein the components so described are in a relationship permitting them to function in their intended manners. A control sequence operatively linked to a coding sequence is ligated such that expression of the coding sequence is achieved under conditions compatible with the control sequences.

"Responsive" is intended to encompass any response of a polypeptide or protein to an interaction with an analyte.

Discussion

Analyte sensors, methods for producing and using analyte sensors, methods of detecting and/or measuring analyte activity, detecting pH change, and/or, controlling the concentration of an analyte in a system, are disclosed. Embodiments of the analyte sensors can provide an accurate and convenient method for characterizing analyte activity, detecting pH change, controlling the concentration of an analyte in a system, and the like, in both in vivo and in vitro environments, in particular in living cell imaging.

Embodiments of the analyte sensors include an optically-active fluorescent host protein and a molecular recognition motif that interacts with an analyte (e.g., calcium (or other metal as noted herein) or a flux of calcium in its microenvironment). Upon interaction of an analyte with the molecular recognition motif, the analyte sensor generates an optically-detectable signal (or the optically-detectable signal is altered) which is produced during exposure to an analyte. The molecular recognition motif is integrated or operatively linked into (within the amino acid sequence) an optically-active fluorescent host protein. The interaction of the analyte with the molecular recognition motif produces a detectable change in fluorescence properties (e.g., change of the intensity, or maxima wavelength or the imaging of the absorption, transmitted light, fluorescent excitation or emission change, light scattering, and/or energy transfer of the chromophore and the protein) of the analyte sensor based on the quantity of the analyte.

Using relevant molecular recognition motifs, the analyte sensor can be used to investigate the mechanisms of diseases, track the process of diseases and diagnose some diseases related to analytes (calcium) activity in vitro, in living cells and in vivo. In addition, a specific signal peptide is also useful for investigating mechanisms such as their activation or inhibition of diseases related to calcium (or other metals as noted herein) activities in various cellular compartments in real time and in situ, which is useful in biotechnology, cell biology and medicinal chemistry, disease diagnosis and prognosis, calcium inhibitor screening and drug development.

Embodiments of the analyte sensors include an optically-active fluorescent host protein (hereinafter "fluorescent host protein") and a molecular recognition motif that includes an analyte binding site. The native signal of the fluorescent protein is altered by the inclusion of the analyte binding site within the amino acid sequence of the fluorescent host protein. In an embodiment of the present disclosure, specific insertion positions of the analyte binding site are selected so that the analyte sensor produces and/or alters emissions at two or more wavelengths. In this regard, the relative three dimensional position of the chromophore within the fluorescent host protein is altered by the inclusion of the analyte binding site, where such alteration generates the altered signal.

Upon interaction of the analyte (e.g., calcium, lead, or a lanthanide) with the analyte binding site, the analyte sensor produces an altered signal relative to the analyte sensor prior to interaction. In this regard, the relative three dimensional position of the chromophore within the fluorescent host protein is altered upon interaction of the analyte with the analyte binding site, where such alteration generates the altered signal.

In other words, the analyte sensors have a folding arrangement in a three-dimensional space that produces a specific signal. The analyte sensor can undergo a local conformational change into another folding arrangement with an alteration of the chromophore microenvironment under the inducement of an analyte (e.g., calcium, lead, or a lanthanide) with the analyte binding site. The conformational change can be detected and measured and compared to the signal generated by the calcium sensor prior to interaction with the analyte.

The advantages of embodiments of the present disclosure can include one or more of the following. First, embodiments of the present disclosure are capable of monitoring numerous cellular events in living cells or organisms via live cell imaging. Embodiments of the present disclosure can provide continuous and dynamic movies of the cellular event and their responses by the stimuli or drugs. Embodiments of the present disclosure largely overcome the limitations of currently commercial available small molecule dyes, peptide/mimics probes with one snap shot of the analyte action. Second, embodiments of the present disclosure include single fluorescent proteins that are more easily and better translocated under cellular environment to probe analyte reaction in situ than FRET pairs that used two fluorescent proteins. With the addition of signal peptides, these analyte sensors can be specifically expressed/placed at the cellular environments such as ER, mitochondral, Golgi or nuclei to monitor cellular event with spational resolution in addition to temporal resolution. Currently available dye detection methods simply rely on passive diffusion of the probe through the membrane, and permits only short snapshots of calcium actions without the capability of detecting reactions at targeted cellular locations. These probes do not provide continuous dynamic imaging of calcium actions due to limited cellular lifetime and specificity.

Third, embodiments of the present disclosure do not use existing/natural calcium binding proteins to sense metal ions (e.g., calcium, lead, or a lanthanide), thus they have minimized perturbation of cellular network. Fourth, embodiments of the present disclosure include single fluorescent protein units that overcome the limitations observed with FRET-based sensors that are prone to fluorescence photobleaching, poor orientation and translocation in the cellular compartments due to their large size. Fifth, the ratiometric signal change of embodiments of the present disclosure with absorption or excitations at 398 and 490 nm permits quantitative and accurate measurement of the calcium (or other metal as noted herein) action by normalizing the concentration change of the sensors and cellular and instrumental interference of the fluorescence signal. Sixth, creating different sensors with different analyte affinities allows for monitoring of cellular response with high accuracy and sensitivity. Seventh, the structural motifs used in embodiments of the present disclosure allow the maximal optical responses as well the optimal molecular recognition required for chemical reactions. Eighth, the developed analyte sensors can be expressed in bacterial, mammalian cells, and animals such as mice with good optical properties such as those described herein.

Embodiments of the present disclosure can produce a difference in the analyte sensor signal prior to and after interaction with the analyte. The difference is a measurable and a statistically-significant difference. A statistically-significant difference is indicated by a difference sufficient to distinguish between these two states, such as about 0.1%, 1%, 3%, 5%, 10%, 15%, 20%, 25%, 30%, or 40% or more difference between the amount of energy emitted in each state, where the statistically significant difference is determined, at least in part, by the components of the calcium sensors or systems as well as the detection system.

Thus, the systems, sensors, and methods of the present disclosure can be used to detect, measure, quantitate, and image interactions between the analytes with the analyte binding site, in vitro and in vivo. In particular, embodiments of the present disclosure can be used to detect (and visualize) and/or quantitate calcium interactions or events in vitro as well as in in vivo. In addition, the systems, sensors, and methods of the present disclosure can be used to detect, measure, quantitate pH change with the analyte binding site, in vitro and in vivo. Furthermore, the systems, sensors, and methods of the present disclosure can be used to control the concentration of an analyte in a system.

In another embodiment, the analyst sensors include a fluorescent host protein and a molecular recognition motif. The molecular recognition motif includes an analyte binding site and a full or partial structural motif (e.g., a primary structure motif, a secondary structure motif, a tertiary structure motif, and/or a quaternary structure motif, such as a, loop, loop-helix, helix-loop, helix-loop-helix motif (including EF-hand motif)), beta-loop-helix, beta-loop-beta and other structural motifs. The structural motifs can be a small domain or fragments and their peptide mimics. The structural motifs provide good accessibility of the analyte binding sites, as well as local perturbation of the environment of the chromophore. The native signal of the fluorescent protein is altered by the inclusion of the analyte binding site within the amino acid sequence of the fluorescent host protein and the structural motif. In particular, embodiments of the present disclosure provide for insertion positions of the analyte binding site so that the analyte sensor produces emissions at two or more wavelengths. In this regard, the relative three dimensional position of the chromophore within the fluorescent host protein is altered by the inclusion of the analyte binding site and the structural motif, where such alteration generates the altered signal.

Upon interaction of the analyte (e.g., calcium, lead, and/or lanthanide) with the analyte binding site, the analyte sensor produces an altered signal relative to the analyte sensor prior to interaction. In this regard, the relative three dimensional position of the chromophore within the fluorescent host protein is altered upon interaction of the analyte with the analyte binding site, where such alteration generates the altered signal. The ratiometric change of the signal (chromophore signal) after the interaction allows an accurate measurement of the analyte activity (e.g., in vitro and in vivo with normalized sensor concentration). The inclusion of the structure motif allows optimal molecular recognition by incorporating essential structural and chemical properties required for a specific type of analyte. For example, inclusion of the structure motif allows for: solvent accessibility for the easy access of calcium, flexibility required for the recognition, a special geometric pocket for the interaction, a hydrophilic surface or charged environments to facilitate the binding process and a required environment for the fast kinetic rates such as good off rate required for real time measurements.

Briefly described, embodiments of this disclosure, among others, include analyte sensors and systems, fusion proteins including the analyte sensor, vectors and other encoding schemes for encoding the analyte sensor and system, and methods of using the analyte sensors and systems, fusion proteins, vectors, and the like. Note that for each of the analyte sensors and systems, proteins, fusion proteins, protein fragments, and nucleotides, one skilled in the art would be able to determine the corresponding nucleotide sequence or protein sequence, respectively, and be able to introduce each into a system of interest.

In an embodiment, the present disclosure provides for analyte sensors including a molecular recognition motif that binds an analyte (e.g., calcium, lead, and/or lanthanide) and an optically-active fluorescent host protein in which the molecular recognition motif is operatively linked to or integrated therein. Interaction of the analyte with the molecular recognition motif produces a detectable change. Table A, FIG. 20A-D, lists embodiments of the analyte sensors, the corresponding SEQ ID NO, and characteristics of the particular analyte sensor. Although SEQ ID NOS. 1-99 includes specific order of amino acids, each of the groups (e.g., molecular recognition motif, fluorescent host protein, and the like) could be positioned differently as long as the analyte sensor produces results consistent with the embodiments disclosed herein.

Additional details regarding the analyte sensors is noted below.

SEQ ID. No. 1, EGFP-III-172, amino acids (aa) 1 to 173 and 186 to 256 correspond to EGFP, aa 174 to 185 correspond to III.

SEQ ID. No. 2, EGFP-E-III-172, amino acids (aa) 1 to 173 and 197 to 262 correspond to EGFP, aa 174 to 196 correspond to E-III.

SEQ ID. No. 3, EGFP-III-F-172, amino acids (aa) 1 to 173 and 194 to 259 correspond to EGFP, aa 174 to 193 correspond to III-F.

SEQ ID. No. 4, EGFP-E-III-F-172, amino acid (aa) 1 to 173 and 205 to 270 correspond to EGFP, as 174 to 204 correspond to E-III-F.

SEQ ID. No. 5, EGFP-E-III-F-172-ER, amino acid (aa) 25 to 197 and 229 to 294 correspond to EGFP, aa 198 to 228 correspond to E-III-F.

SEQ ID. No. 6, EGFP-E-III-F-172-mito, amino acid (aa) 36 to 213 and 245 to 310 correspond to EGFP, aa 214 to 244 correspond to E-III-F.

SEQ ID. No. 7, EGFP-E-III-F-172-SKEAA, amino acid (aa) 1 to 173 and 206 to 271 correspond to EGFP, aa 174 to 205 correspond to E-III-F.

SEQ ID. No. 8, EGFP-E-III-F-172-D/N, amino acid (aa) 1 to 173 and 205 to 270 correspond to EGFP, aa 174 to 204 correspond to E-III-F.

SEQ ID. No. 9, EGFP-E-III-F-172-DD/NN, amino acid (aa) 1 to 173 and 205 to 270 correspond to EGFP, aa 174 to 204 correspond to E-III-F.

SEQ ID. No. 10, EGFP-E-III-F-172-L194N, amino acid (aa) 1 to 173 and 205 to 270 correspond to EGFP, aa 174 to 204 correspond to E-III-F.

SEQ ID. No. 11, EGFP-I-172, amino acid (aa) 1 to 173 and 186 to 251 correspond to EGFP, aa 174 to 185 correspond to I.

SEQ ID. No. 12, EGFP-α-Lac1-172, amino acid (aa) 1 to 173 and 206 to 271 correspond to EGFP, aa 174 to 205 correspond to α-Lac1.

SEQ ID. No. 13, EGFP-α-Lac2-172, amino acid (aa) 1 to 173 and 206 to 271 correspond to EGFP, aa 174 to 205 correspond to α-Lac2.

SEQ ID. No. 14, EGFP-α-Lac3-172, amino acid (aa) 1 to 173 and 206 to 271 correspond to EGFP, aa 174 to 205 correspond to α-Lac3.

SEQ ID. No. 15, EGFP-α-Lac4-172, amino acid (aa) 1 to 173 and 206 to 271 correspond to EGFP, aa 174 to 205 correspond to α-Lac4.

SEQ ID. No. 16, EGFP-III-172-C2, amino acids (aa) 1 to 173 and 186 to 256 correspond to EGFP, aa 174 to 185 correspond to III.

SEQ ID. No. 17, EGFP-E-III-172-C2, amino acids (aa) 1 to 173 and 197 to 262 correspond to EGFP, aa 174 to 196 correspond to E-III.

SEQ ID. No. 18, EGFP-III-F-172-C2, amino acids (aa) 1 to 173 and 194 to 259 correspond to EGFP, aa 174 to 193 correspond to III-F.

SEQ ID. No. 19, EGFP-E-III-F-172-C2, amino acid (aa) 1 to 173 and 205 to 270 correspond to EGFP, aa 174 to 204 correspond to E-III-F.

SEQ ID. No. 20, EGFP-E-III-F-172-ER-C2, amino acid (aa) 25 to 197 and 229 to 294 correspond to EGFP, aa 198 to 228 correspond to E-III-F.

SEQ ID. No. 21, EGFP-E-III-F-172-mito-C2, amino acid (aa) 36 to 213 and 245 to 310 correspond to EGFP, aa 214 to 244 correspond to E-III-F.

SEQ ID. No. 22, EGFP-E-III-F-172-SKEAA-C2, amino acid (aa) 1 to 173 and 206 to 271 correspond to EGFP, aa 174 to 205 correspond to E-III-F.

SEQ ID. No. 23, EGFP-E-III-F-172-DIN-C2, amino acid (aa) 1 to 173 and 205 to 270 correspond to EGFP, aa 174 to 204 correspond to E-III-F.

SEQ ID. No. 24, EGFP-E-III-F-172-DD/NN-C2, amino acid (aa) 1 to 173 and 205 to 270 correspond to EGFP, aa 174 to 204 correspond to E-III-F.

SEQ ID. No. 25, EGFP-E-III-F-172-L194N-C2, amino acid (aa) 1 to 173 and 205 to 270 correspond to EGFP, aa 174 to 204 correspond to E-III-F.

SEQ ID. No. 26, EGFP-I-172-C2, amino acid (aa) 1 to 173 and 186 to 251 correspond to EGFP, aa 174 to 185 correspond to I.

SEQ ID. No. 27, EGFP-α-Lac1-172-C2, amino acid (aa) 1 to 173 and 206 to 271 correspond to EGFP, aa 174 to 205 correspond to α-Lac1.

SEQ ID. No. 28, EGFP-α-Lac2-172-C2, amino acid (aa) 1 to 173 and 206 to 271 correspond to EGFP, aa 174 to 205 correspond to α-Lac2.

SEQ ID. No. 29, EGFP-α-Lac3-172-C2, amino acid (aa) 1 to 173 and 206 to 271 correspond to EGFP, aa 174 to 205 correspond to α-Lac3.

SEQ ID. No. 30, EGFP-α-Lac4-172-C2, amino acid (aa) 1 to 173 and 206 to 271 correspond to EGFP, aa 174 to 205 correspond to α-Lac4.

SEQ ID. No. 31, EGFP-III-172-C3, amino acids (aa) 1 to 173 and 186 to 256 correspond to EGFP, aa 174 to 185 correspond to III.

SEQ ID. No. 32, EGFP-E-III-172-C3, amino acids (aa) 1 to 173 and 197 to 262 correspond to EGFP, aa 174 to 196 correspond to E-III.

SEQ ID. No. 33, EGFP-III-F-172-C3, amino acids (aa) 1 to 173 and 194 to 259 correspond to EGFP, aa 174 to 193 correspond to III-F.

SEQ ID. No. 34, EGFP-E-III-F-172-C3, amino acid (aa) 1 to 173 and 205 to 270 correspond to EGFP, aa 174 to 204 correspond to E-III-F.

SEQ ID. No. 35, EGFP-E-III-F-172-ER-C3, amino acid (aa) 25 to 197 and 229 to 294 correspond to EGFP, aa 198 to 228 correspond to E-III-F.

SEQ ID. No. 36, EGFP-E-III-F-172-mito-C3, amino acid (aa) 36 to 213 and 245 to 310 correspond to EGFP, aa 214 to 244 correspond to E-III-F.

SEQ ID. No. 37, EGFP-E-III-F-172-SKEAA-C3, amino acid (aa) 1 to 173 and 206 to 271 correspond to EGFP, aa 174 to 205 correspond to E-III-F.

SEQ ID. No. 38, EGFP-E-III-F-172-D/N-C3, amino acid (aa) 1 to 173 and 205 to 270 correspond to EGFP, aa 174 to 204 correspond to E-III-F.

SEQ ID. No. 39, EGFP-E-III-F-172-DD/NN-C3, amino acid (aa) 1 to 173 and 205 to 270 correspond to EGFP, aa 174 to 204 correspond to E-III-F.

SEQ ID. No. 40, EGFP-E-III-F-172-L194N-C3, amino acid (aa) 1 to 173 and 205 to 270 correspond to EGFP, aa 174 to 204 correspond to E-III-F.

SEQ ID. No. 41, EGFP-I-172-C3, amino acid (aa) 1 to 173 and 186 to 251 correspond to EGFP, aa 174 to 185 correspond to I.

SEQ ID. No. 42, EGFP-α-Lac1-172-C3, amino acid (aa) 1 to 173 and 206 to 271 correspond to EGFP, aa 174 to 205 correspond to α-Lac1.

SEQ ID. No. 43, EGFP-α-Lac2-172-C3, amino acid (aa) 1 to 173 and 206 to 271 correspond to EGFP, aa 174 to 205 correspond to α-Lac2.

SEQ ID. No. 44, EGFP-α-Lac3-172-C3, amino acid (aa) 1 to 173 and 206 to 271 correspond to EGFP, aa 174 to 205 correspond to α-Lac3.

SEQ ID. No. 45, EGFP-α-Lac4-172-C3, amino acid (aa) 1 to 173 and 206 to 271 correspond to EGFP, aa 174 to 205 correspond to α-Lac4.

SEQ ID. No. 46, EGFP-III-157, amino acid (aa) 1 to 158 and 171 to 251 correspond to EGFP, aa 159 to 170 correspond to III.

SEQ ID. No. 47, EGFP-E-III-F-157, amino acid (aa) 1 to 158 and 190 to 270 correspond to EGFP, aa 159 to 189 correspond to E-III-F.

SEQ ID. No. 48, EGFP-III-157-C2, amino acid (aa) 1 to 158 and 171 to 251 correspond to EGFP, aa 159 to 170 correspond to III.

SEQ ID. No. 49, EGFP-E-III-F-157-C2, amino acid (aa) 1 to 158 and 190 to 270 correspond to EGFP, as 159 to 189 correspond to E-III-F.

SEQ ID. No. 50, EGFP-III-157-C3, amino acid (aa) 1 to 158 and 171 to 251 correspond to EGFP, aa 159 to 170 correspond to III.

SEQ ID. No. 51, EGFP-E-III-F-157-C3, amino acid (aa) 1 to 158 and 190 to 270 correspond to EGFP, aa 159 to 189 correspond to E-III-F.

SEQ ID. No. 52, EGFP-E-III-F-170, amino acid (aa) 1 to 171 and 203 to 270 correspond to EGFP, aa 172 to 202 correspond to E-III-F.

SEQ ID. No. 53, EGFP-E-I-F-170, amino acid (aa) 1 to 171 and 206 to 273 correspond to EGFP, aa 172 to 205 correspond to E-I-F.

SEQ ID. No. 54, EGFP-E-III-F-170-C2, amino acid (aa) 1 to 171 and 203 to 270 correspond to EGFP, aa 172 to 202 correspond to E-III-F.

SEQ ID. No. 55, EGFP-E-I-F-170-C2, amino acid (aa) 1 to 171 and 206 to 273 correspond to EGFP, aa 172 to 205 correspond to E-I-F.

SEQ ID. No. 56, EGFP-E-III-F-170-C3, amino acid (aa) 1 to 171 and 203 to 270 correspond to EGFP, aa 172 to 202 correspond to E-III-F.

SEQ ID. No. 57, EGFP-E-I-F-170-C3, amino acid (aa) 1 to 171 and 206 to 273 correspond to EGFP, aa 172 to 205 correspond to E-I-F.

SEQ ID. No. 58, EGFP-120, amino acid (aa) 1 to 239 correspond to EGFP, as 16, 114, 116, 121, and 123 correspond to a $Ca^{2+}$ binding site.

SEQ ID. No. 59, EGFP-120b, amino acid (aa) 1 to 239 correspond to EGFP, aa 16, 112, 116, 121, and 123 correspond to a $Ca^{2+}$ binding site.

SEQ ID. No. 60, EGFP-177, amino acid (aa) 1 to 239 correspond to EGFP, aa 136, 172, 174, 176, and 178 correspond to a $Ca^{2+}$ binding site.

SEQ ID. No. 61, EGFP-194a, amino acid (aa) 1 to 239 correspond to EGFP, aa 6, 80, 83, 86, and 195 correspond to a $Ca^{2+}$ binding site.

SEQ ID. No. 62, EGFP-194b, amino acid (aa) 1 to 239 correspond to EGFP, aa 6, 80, 83, 87, and 195 correspond to a $Ca^{2+}$ binding site.

SEQ ID. No. 63, EGFP-229, amino acid (aa) 1 to 239 correspond to EGFP, aa 79, 82, 198, 200, and 230 correspond to a $Ca^{2+}$ binding site.

SEQ ID. No. 64, EGFP-site1, amino acid (aa) 1 to 239 correspond to EGFP, aa 3, 6, 83, 87, and 195 correspond to a $Ca^{2+}$ binding site.

SEQ ID. No. 65, EGFP-site1-ER, amino acid (aa) 25 to 263 correspond to EGFP, aa 27, 30, 107, 111, and 219 correspond to a $Ca^{2+}$ binding site.

SEQ ID. No. 66, EGFP-site1-mito, amino acid (aa) 36 to 274 correspond to EGFP, aa 38, 41, 118, 122, and 230 correspond to a $Ca^{2+}$ binding site.

SEQ ID. No. 67, EGFP-site2, amino acid (aa) 1 to 239 correspond to EGFP, aa 16, 18, 116, 121, and 123 correspond to a $Ca^{2+}$ binding site.

SEQ ID. No. 68, EGFP-site3, amino acid (aa) 1 to 239 correspond to EGFP, aa 84, 153, 155, 162, and 195 correspond to a $Ca^{2+}$ binding site.

SEQ ID. No. 69, EGFP-site4, amino acid (aa) 1 to 239 correspond to EGFP, aa 60, 101, 137, 142, and 178 correspond to a $Ca^{2+}$ binding site.

SEQ ID. No. 70, EGFP-site5, amino acid (aa) 1 to 239 correspond to EGFP, aa 8, 13, 89, 115, and 120 correspond to a $Ca^{2+}$ binding site.

SEQ ID. No. 71, EGFP-site6, amino acid (aa) 1 to 239 correspond to EGFP, aa 8, 13, 89, 115, and 120 correspond to a $Ca^{2+}$ binding site.

SEQ ID. No. 72, EGFP-120-C2, amino acid (aa) 1 to 239 correspond to EGFP, aa 16, 114, 116, 121, and 123 correspond to a $Ca^{2+}$ binding site.

SEQ ID. No. 73, EGFP-120b-C2, amino acid (aa) 1 to 239 correspond to EGFP, aa 16, 112, 116, 121, and 123 correspond to a $Ca^{2+}$ binding site.

SEQ ID. No. 74, EGFP-177-C2, amino acid (aa) 1 to 239 correspond to EGFP, aa 136, 172, 174, 176, and 178 correspond to a $Ca^{2+}$ binding site.

SEQ ID. No. 75, EGFP-194a-C2, amino acid (aa) 1 to 239 correspond to EGFP, aa 6, 80, 83, 86, and 195 correspond to a $Ca^{2+}$ binding site.

SEQ ID. No. 76, EGFP-194b-C2, amino acid (aa) 1 to 239 correspond to EGFP, aa 6, 80, 83, 87, and 195 correspond to a $Ca^{2+}$ binding site.

SEQ ID. No. 77, EGFP-229-C2, amino acid (aa) 1 to 239 correspond to EGFP, aa 79, 82, 198, 200, and 230 correspond to a $Ca^{2+}$ binding site.

SEQ ID. No. 78, EGFP-site1-C2, amino acid (aa) 1 to 239 correspond to EGFP, aa 3, 6, 83, 87, and 195 correspond to a $Ca^{2+}$ binding site.

SEQ ID. No. 79, EGFP-site1-ER-C2, amino acid (aa) 25 to 263 correspond to EGFP, aa 27, 30, 107, 111, and 219 correspond to a $Ca^{2+}$ binding site.

SEQ ID. No. 80, EGFP-site1-mito-C2, amino acid (aa) 36 to 274 correspond to EGFP, aa 38, 41, 118, 122, and 230 correspond to a $Ca^{2+}$ binding site.

SEQ ID. No. 81, EGFP-site2-C2, amino acid (aa) 1 to 239 correspond to EGFP, aa 16, 18, 116, 121, and 123 correspond to a $Ca^{2+}$ binding site.

SEQ ID. No. 82, EGFP-site3-C2, amino acid (aa) 1 to 239 correspond to EGFP, aa 84, 153, 155, 162, and 195 correspond to a $Ca^{2+}$ binding site.

SEQ ID. No. 83, EGFP-site4-C2, amino acid (aa) 1 to 239 correspond to EGFP, aa 60, 101, 137, 142, and 178 correspond to a $Ca^{2+}$ binding site.

SEQ ID. No. 84, EGFP-sites-C2, amino acid (aa) 1 to 239 correspond to EGFP, aa 8, 13, 89, 115, and 120 correspond to a $Ca^{2+}$ binding site.

SEQ ID. No. 85, EGFP-site6-C2, amino acid (aa) 1 to 239 correspond to EGFP, aa 8, 13, 89, 115, and 120 correspond to a $Ca^{2+}$ binding site.

SEQ ID. No. 86, EGFP-120-C3, amino acid (aa) 1 to 239 correspond to EGFP, aa 16, 114, 116, 121, and 123 correspond to a $Ca^{2+}$ binding site.

SEQ ID. No. 87, EGFP-120b-C3, amino acid (aa) 1 to 239 correspond to EGFP, aa 16, 112, 116, 121, and 123 correspond to a $Ca^{2+}$ binding site.

SEQ ID. No. 88, EGFP-177-C3, amino acid (aa) 1 to 239 correspond to EGFP, aa 136, 172, 174, 176, and 178 correspond to a $Ca^{2+}$ binding site.

SEQ ID. No. 89, EGFP-194a-C3, amino acid (aa) 1 to 239 correspond to EGFP, aa 6, 80, 83, 86, and 195 correspond to a $Ca^{2+}$ binding site.

SEQ ID. No. 90, EGFP-194b-C3, amino acid (aa) 1 to 239 correspond to EGFP, aa 6, 80, 83, 87, and 195 correspond to a $Ca^{2+}$ binding site.

SEQ ID. No. 91, EGFP-229-C3, amino acid (aa) 1 to 239 correspond to EGFP, aa 79, 82, 198, 200, and 230 correspond to a $Ca^{2+}$ binding site.

SEQ ID. No. 92, EGFP-site1-C3, amino acid (aa) 1 to 239 correspond to EGFP, aa 3, 6, 83, 87, and 195 correspond to a $Ca^{2+}$ binding site.

SEQ ID. No. 93, EGFP-site1-ER-C3, amino acid (aa) 25 to 263 correspond to EGFP, aa 27, 30, 107, 111, and 219 correspond to a $Ca^{2+}$ binding site.

SEQ ID. No. 94, EGFP-site1-mito-C3, amino acid (aa) 36 to 274 correspond to EGFP, aa 38, 41, 118, 122, and 230 correspond to a $Ca^{2+}$ binding site.

SEQ ID. No. 95, EGFP-site2-C3, amino acid (aa) 1 to 239 correspond to EGFP, aa 16, 18, 116, 121, and 123 correspond to a $Ca^{2+}$ binding site.

SEQ ID. No. 96, EGFP-site3-C3, amino acid (aa) 1 to 239 correspond to EGFP, aa 84, 153, 155, 162, and 195 correspond to a $Ca^{2+}$ binding site.

SEQ ID. No. 97, EGFP-site4-C3, amino acid (aa) 1 to 239 correspond to EGFP, aa 60, 101, 137, 142, and 178 correspond to a $Ca^{2+}$ binding site.

SEQ ID. No. 98, EGFP-site5-C3, amino acid (aa) 1 to 239 correspond to EGFP, aa 8, 13, 89, 115, and 120 correspond to a $Ca^{2+}$ binding site.

SEQ ID. No. 99, EGFP-site6-C3, amino acid (aa) 1 to 239 correspond to EGFP, aa 8, 13, 89, 115, and 120 correspond to a $Ca^{2+}$ binding site.

The optically-active fluorescent host protein can have the molecular recognition motif inserted or integrated into the optically-active fluorescent host protein at one of a number of locations, where each different insertion point provides an analyte sensor with different characteristics. For example, when the optically-active fluorescent host protein is an enhanced fluorescent protein (EGFP), the molecular recognition motif can be inserted into the positions 152, 172, or 170. Additional details and the examples that describe specific embodiments of the present disclosure are provided below.

It should also be noted that the optically-active fluorescent host protein can be modified to enhance the thermal stability and/or the fluorescent properties of the analyte sensor by including two or three mutations to the optically-active fluorescent host protein. In particular, the EGFP can include two mutations (M153T, V163A) and/or three mutations (F99S, M153T, V163A), which increase thermal stability and or fluorescence properties, as described herein. These mutations are noted in SEQ ID Nos. 16 to 45, SEQ ID Nos. 48 to 51, SEQ ID Nos. 54 to 57, and SEQ ID Nos. 72 to 99 respectively, as described herein. Additional details and the examples that describe specific embodiments of the present disclosure are provided below.

The molecular recognition motif can include an analyte binding site. The analyte binding motif includes a $Ca^{2+}$ binding motif. The $Ca^{2+}$ binding motif can include, but is not limited to, EF-hand calcium binding motifs such as, but not limited to, motifs from EF-hand motifs I-IV, from calmodulin and alpha-lactalbumin and their variants (SEQ ID Nos. 1-58, where the specific sequence listings are noted above) or other calcium binding sites. As mentioned above, the motifs can be positioned differently than described herein as long as they have characteristics that are consistent with the embodiments disclosed. It should be noted that the $Ca^{2+}$ binding motif could be used to detect other metal ions such as, lead ions and lanthanide ions. Additional details and the examples that describe specific embodiments of the present disclosure are provided below.

In another embodiment, the molecular recognition motif can include the analyte binding site and one or more structural motifs. The analyte binding site can include those described above. The structural motif includes, but is not limited to, a loop (e.g., EF-loops), a loop-helix, a helix-loop, a helix-loop-helix motif, a beta-loop-helix, and a beta-loop-beta; such as those noted in SEQ ID Nos. 1-58, where the specific amino acid sequences are noted above. As mentioned above, the motifs can be positioned differently than described herein as long as they have characteristics that are consistent with the embodiments disclosed. Additional details are provided below and the Examples that describe specific embodiments of the present disclosure.

In another embodiment, the molecular recognition motif can include the analyte binding site, one or more structural motif, and a targeting motif. The analyte binding site and the structural can include those described above. The targeting motif can target organelles and sub-organelles such as, but not limited to, ER, mitochondrion, Golgi, nucleus, channels, gap junctions, and extracellular spaces. The targeting motif includes, but is not limited to, signal peptides encoded in the proteins located in the target organelles. The targeting motif includes those listed in SEQ ID Nos. 5-6, 20-21, 35-36, 65-66, 79-80, 93-94, where the specific amino acid sequences are noted above. As mentioned above, the motifs can be positioned differently than described herein as long as they have characteristics that are consistent with the embodiments disclosed. Additional details and the examples that describe specific embodiments of the present disclosure are provided below.

In an embodiment, the present disclosure provides for analyte sensors including a molecular recognition motif that binds an analyte (e.g., calcium, lead, and/or lanthanide) and an optically-active fluorescent host protein in which the molecular recognition motif is operatively linked to or integrated therein. Interaction of the analyte with the molecular recognition motif produces a detectable change. The analyte sensor has a protein sequence that includes the molecular recognition motif and the optically-active fluorescent host protein selected from: SEQ ID NOS: 5, 6, 20, 21, 35, 36, 80, 81, 94, and 95.

In another embodiment, the present disclosure provides for analyte sensors including a molecular recognition motif that binds an analyte (e.g., calcium, lead, and/or lanthanide) and an optically-active fluorescent host protein in which the molecular recognition motif is operatively linked to or integrated therein. Interaction of the analyte with the molecular recognition motif produces a detectable change. The analyte sensor has at least one characteristic selected from the following: is stable at temperatures greater than about 30° C.; has enhanced fluorescent and optical properties (e.g., mutations of the fluorescent protein (e.g., F99S, M153T and V163A)), and combinations thereof. In particular, embodiments of the analyte sensors (denoted as c2 or c3 variants in the Examples) (SEQ ID NOS. 16-45, 48-51, 54-57, and 72-99) are able to maintain fluorescence at both mammalian and bacterial cells. Each of the embodiments described herein are able to bind calcium and other metal ions (e.g., $Pb^{2+}$, $Tb^{3+}$, $La^{3+}$, and $Gd^{3+}$). Additional details and the examples that describe specific embodiments of the present disclosure are provided below.

Methods, Systems, and Processes for Constructing Analyte Sensors

The analyte sensor can be constructed by first constructing a molecular recognition motif (e.g., including the analyte binding site) capable of responding to an analyte (e.g., calcium, lead, and/or lanthanide) and second by operatively inserting the molecular recognition motif into a fluorescent host protein. Molecular recognition motifs typically have a primary structure, a secondary structure, and a tertiary structure in most cases and in some cases a quaternary structure, at least one of which can be tailored to the analyte sensor to achieve a desired level of analyte sensitivity. That is, each of the primary structure, the secondary structure, the tertiary structure, and if present, the quaternary structure can be tailored to the analyte sensor independently or in combination with one or more others of the structures to achieve a desired level of sensitivity for the sensor relative to the analyte. For example, the binding of the analyte to the molecular recognition motif preferably produces a detectable change (fluorescence) and the manipulation of the molecular recognition motif manipulates the responsiveness of the sensor.

The analyte sensor also allows the quantification of an analyte (e.g., calcium, lead, and/or lanthanide) by introducing a nucleotide sequence for a protein to an analyte sensor with a molecular recognition motif that is able to produce a detectable change upon excitation, expressing the protein, providing excitement to the analyte sensor, and then quantifying the detectable change. Preferably, the protein can include a fluorescent host protein, whose emission intensity is relative to the quantity of analyte in a microenvironment.

Additionally, a nucleic acid sequence can be created for an analyte sensor comprising a molecular recognition motif sequence for an analyte binding peptide that produces a detectable change upon excitation and a host sequence for a fluorescent host protein. In this nucleic acid sequence, the molecular recognition motif sequence and the fluorescent host protein sequence are operatively linked, and manipulation of the molecular recognition motif sequence manipulates the responsiveness of the analyte sensor. Methods for constructing analyte sensors are described in U.S. patent application Ser. Nos. 10/914,572; 10/914,769; 10/914,573, each of which were filed on Aug. 9, 2004, each of which are incorporated herein by reference.

One method for creating a molecular recognition motif is through the use of a grafting method. The grafting method focuses on engineering and constructing a molecular recognition motif by modifying the primary, secondary, tertiary, and/or quaternary structure of an identified binding site. In one example, a $Ca^{2+}$ binding motif may be constructed from continuous binding motifs such as conserved calcium binding motifs from EF-hand proteins (EF-loop) using a grafting method, which can involve criteria to obtain a preferred intrinsic metal-binding affinity for each calcium binding motif.

An illustrative method for constructing a molecular recognition motif using the grafting method includes first identifying an analyte binding peptide that binds an analyte with specificity and then ascertaining at least a portion of a nucleic acid sequence encoding the analyte binding peptide. Once this is accomplished, the nucleic acid sequence encoding the analyte binding peptide is tailored into a molecular recognition motif that includes an analyte binding site. After the tailoring is completed, a fluorescent host protein is selected and a relevant portion of the nucleic acid sequence of the fluorescent host protein is identified, and the tailored nucleic acid sequence encoding the analyte binding peptide is operatively linked with the fluorescent host protein nucleic acid sequence into a molecular recognition motif sequence. Finally, the molecular recognition motif sequence is expressed. In this method, the nucleic acid sequence encoding the analyte binding peptide is tailored so as to achieve the molecular recognition motif with a desired specificity for the analyte. Preferably, the nucleic acid sequence encoding the analyte binding peptide is tailored to have specificity for the analyte over other analytes. Resultant proteins encoded by the molecular recognition motif sequence are useful products of this disclosure.

As mentioned previously, analyte binding sites typically have a primary structure, a secondary structure, in most cases a tertiary structure, and in some cases a quaternary structure, each of which can be modified independently or in combination with others of the structures when tailoring of the nucleic acid sequence encoding the analyte binding peptide. For example, the primary structure can be tailored by inserting at least one codon into the nucleic acid sequence encoding the analyte binding peptide. Similarly, codons for charged amino acids can be inserted into the nucleic acid sequence encoding the analyte binding peptide.

The analyte binding site can be tailored by selectively manipulating and adding helices, loops, bridges or linkers, among other methods. Charged amino acids can be inserted into the amino acid sequence encoding the analyte binding peptide and or aromatic amino acids can be introduced into the amino acid sequence encoding the analyte binding peptide.

Another method for creating a molecular recognition motif is through the use of a computational approach in which a computational method for engineering and constructing a molecular recognition motif de novo is based on optimal binding characteristics of an analyte with other moieties. In one illustrative embodiment, using established criteria for evaluating $Ca^{2+}$ binding data, a $Ca^{2+}$ binding site of desired sensitivity may be constructed by molecular modeling. For example, such computation algorithms may be used to develop desired ion binding motifs based on parameters such as the metal's binding geometry, the folding of the host protein, the location of the charges on the fluorescent protein, the particular chromophores, and other criteria specific to the $Ca^{2+}$ binding data.

The computational approach can be used to construct a molecular recognition motif by accessing public and or private databases that include structural data on analyte binding sites, generating at least one preliminary analyte binding site from the structural data based on certain previously selected criteria, selecting one or more suitable analyte binding sites from the preliminary analyte binding sites, and constructing the analyte binding motif by tailoring the selected analyte binding site and operatively linking it with a host protein, keeping in mind that the molecular recognition motif preferably has a specificity for a selected analyte. The structural data typically can include amino acid sequences, secondary structures, nucleic acid sequences, geometric parameters, electrostatic properties, and coordination properties of the analyte binding sites, such as in protein and gene banks.

An illustrative version of this computational approach is the computerized (or otherwise automated) querying of one or more databases that include structural data on analyte binding sites using selected criteria relevant to the molecular recognition motif, generating at least one preliminary analyte binding site from the database information based on compatibility with the selected criteria, and selecting one or more suitable analyte binding sites from the preliminary analyte binding sites based on optimal compatibility with the selected criteria. Once a suitable analyte binding site is selected, the nucleic acid sequence of the selected analyte binding site is obtained, tailored, and operatively linked with a fluorescent host protein sequence, whereby the nucleic acid sequence of the selected analyte binding site is tailored so to achieve the molecular recognition motif having a desired specificity for the analyte. In one embodiment of the computational approach, at least one preliminary binding site is generated based on random portions of the structural data. Further, a nucleic acid sequence encoding the preliminary binding sites can be generated from the structural data. The computational approach also can be used to express the molecular recognition motif.

The computational approach can be performed on or by a system including at least one database that comprises the structural data on analyte binding sites, an algorithm for generating the preliminary analyte binding sites from portions of the structural data using selected criteria relevant to the molecular recognition motif and rating the preliminary analyte binding sites based on specificity for a selected analyte, and a computer for executing the algorithm so as to query the databases to generate the preliminary analyte binding sites. The algorithm generally is a relatively simple searching algorithm that will query the databases based on inputted criteria.

Once the molecular recognition motif has been tailored and operatively linked into the fluorescent host protein, the analyte sensor may show responsiveness to analyte dependant fluorescence variations. The responsiveness of the analyte sensor is caused by the interaction of the fluorescent host protein with the molecular recognition motif, which then may display fluorescence properties proportional to the analyte concentration or flux. In particular, the responsiveness is thought to be caused by changes in the orientation and protonation of the chromophore of the fluorescent protein. The interaction between the analyte and the fluorescent host protein may result in a shift in the emission spectra, quantum yield, and/or extinction coefficient, which may be quantitatively analyzed in real-time to probe the microenvironment.

In use and application, the analyte sensor may be used to detect and quantify the analyte concentration and flux thereof in a sample as a non-ratiometric dye. More particularly, the analyte sensor is inserted into the sample, the sample then is excited by radiation, the fluorescence from the sample then is measured using an optical device, and the fluorescence or flux thereof then is analyzed to quantify or detect the analyte concentration in the sample. In order to analyze the sample, it may be necessary to generate a standard curve based on the fluorescence generated from known analyte concentrations. Specifically, the fluorescence signal of the analyte sensor is compared to the fluorescence of the standard curve so as to determine the concentration of analyte in the sample.

Fluorescent Host Proteins

As mentioned above, the analyte sensor includes a fluorescent host protein (also referred to as "optically active fluorescent host protein" or "optically active fluorescent protein"). The native signal of the fluorescent protein is altered by the inclusion of the analyte binding site within the amino acid sequence of the fluorescent host protein. Embodiments of the present disclosure provide for specific insertion positions (described in more detail below) of the analyte binding site within the fluorescent host protein so that the analyte sensor produces an emission that is altered upon interaction of the analyte with the analyte binding site. In this regard, the relative three dimensional position of the chromophore within the fluorescent host protein is altered by the inclusion of the analyte binding site, where such alteration generates the altered signal. In an embodiment, the analyte sensors can emit at two or more wavelengths.

One group of fluorescent host proteins includes the Green Fluorescent Protein isolated from *Aequorea Victoria* (GFP), as well as a number of GFP variants, such as enhanced fluorescent proteins (EGFP).

In particular, *Aequorea* green fluorescent proteins (GFPs) and its enhanced fluorescent proteins have 238 amino acid residues in a single polypeptide chain. The native molecule has been shown to regenerate its intrinsic fluorescence from the totally denatured state. GFPs display a strong visible absorbance and fluorescence that is thought to be generated by the autocyclization and oxidation of the chromophore having a tripeptide Ser-Tyr-Gly sequence at positions 65 to 67. Mutations to GFPs have resulted in various shifts in absorbance and fluorescence. The usefulness of GFPs stems from the fact that fluorescence from GFP requires no additional co-factors; the fluorophore is self-assembling via a cyclization reaction of the peptide backbone.

The chromophore of GFP is formed by the cyclization of the tripeptide Ser65-Tyr66-Gly67. This chromophore is located inside of the β-barrel that is composed of 11 antiparallel strands and a single central α-helix. There are short helices capping the ends of the β-barrel. The chromophore has extensive hydrogen bonding with the protein frame and can be affected by water molecules under the different folding states. The chromophore in a tightly constructed β-barrel that exhibits absorption peaks at 400 and 480 nm and an emission peak at 510 nm with a quantum yield of about 0.72 when excited at 470 nm. The chromophore in enhanced green fluorescent protein (EGFP), which is GFP with a mutation S65T, has an improved fluorescence intensity and thermo-sensitivity.

Two (M153T, V163A) or three additional mutations (F99S, M153T, V163A) were added to EGFP to increase the protein expression, stability, chromophore formation at 37° C. or above.

In particular, the fluorescent host protein can include, but is not limited to, enhanced green fluorescent protein and variants or mutants thereof. The linker containing specific analyte binding sites are grafted between the position 170, 172, and 157, all of sequence are shown in SEQ ID from NO. 1 to NO. 58, where the specific amino acid sequences are noted above.

The analyte binding sites can be created by mutation in the fluorescent proteins to form a proper binding pocket without using amino acids from a continuous stretch of the sequence. All of the sequences are shown in SEQ ID NOs. 59 to 100 include these mutations, where the specific amino acid sequences are noted above.

The term "mutant" is employed broadly to refer to a protein that differs in some way from a reference wild-type protein, where the protein may retain biological properties of the reference wild-type (e.g., naturally occurring) protein, or may have biological properties that differ from the reference wild-type protein. The term "biological property" of the subject proteins includes, but is not limited to, spectral properties, such as emission maximum, quantum yield, and brightness, and the like; in vivo and/or in vitro stability (e.g., half-life); and the like. Mutants can include single amino acid changes (point mutations), deletions of one or more amino acids (point-deletions), N-terminal truncations, C-terminal truncations, insertions, and the like. Mutants can be generated using standard techniques of molecular biology.

The fluorescent protein can include conservatively modified variants as long as the conservatively modified variant retains certain characteristics (e.g., the ability to fluoresce upon complementation) of the analyte sensor. It should be noted that polynucleotides encoding the conservatively modified variants are intended to be disclosed by and included in this disclosure.

The analyte sensor can be expressed in a system (e.g., a cell) using a vector, for example by methods described herein or by methods known to those of skill in the art.

Analyte Binding Site

As described above, the analyte sensor can have a molecular recognition motif that includes an analyte binding site. The native signal of the fluorescent protein is altered by the inclusion of the analyte binding site within the amino acid sequence of the fluorescent host protein. In this regard, the relative three dimensional position of the chromophore within the fluorescent host protein is altered by the inclusion of the analyte binding site, where such alteration generates the altered signal. This signal change in the majority of our sensors results in a ratiometric change i.e. changes (e.g., increase, decrease, or increase at one wavelength and a decrease at another wavelength) at two wavelengths for both absorption and fluorescence excitation.

The analyte binding site functions by interacting with an analyte (e.g., calcium, lead, and/or lanthanide), where such interaction causes the analyte sensor to produce an altered signal relative to the analyte sensor prior to interaction. In this regard, the relative three dimensional position of the chromophore within the fluorescent host protein is altered upon interaction of the analyte with the analyte binding site, where such alteration generates the altered signal.

The analyte binding site can include, but is not limited to, a binding site where the analyte binds to the analyte sensor. The binding site is the location where the analyte binds to the analyte sensor. Usually specific types of amino acids in specific arrangements in sequence and in three dimensions are used for a specific type of analyte. Depending on the reaction and the nature of the binding and relative alteration of the chromophore, the binding of the analyte causes an alteration in the analyte sensor signal. However, the cleavage reaction will cause large changes of the sensor signal. This can be due to the alteration of the local environment of the three dimensional position of the chromophore within the fluorescent host protein which results in alteration of the signal. Such alteration could be due to the perturbation of the hydrogen network, the dynamic properties, the solvent accessibility or chemical properties such as hydrphic and electrostatic interaction.

The site within the fluorescent host protein for inserting the analyte binding site cleavage site can be selected so that the location is accessible by the analyte (calcium). In addition, the location within the fluorescent host protein can be selected so that the location does not substantially reduce the fluorescence from the fluorescent host protein and so that the locations do not substantially denature or alter the protein folding of the fluorescent host protein or chromophore. Furthermore, the site within the fluorescent host protein for inserting the analyte binding site cleavage site can be selected based on one or more of the following criteria: maximization of solvent accessibility to allow efficient enzymatic action, maximization of fluorescent/optical signals once the analyte binding site is operatively incorporated into the fluorescent host protein; minimization of the disruption to the chromophore environment after interaction of the analyte binding site with the analyte; minimizing the effects on the protein folding and packing of the fluorescent host protein; and maximization of the ratiometric change of chromophore signal due to interaction of the analyte binding site with the analyte so to allow an accurate measurement of the analyte activity in vitro or in vivo.

It should be noted that the analyte binding site can be include within or between motifs of the fluorescent host protein, such as within or between a secondary structure motif, a tertiary structure motif, or a quaternary structure motif. In particular, the analyte binding site can be inserted in the loop of the β-barrel, and between loops.

Structure Motifs

The inclusion of the structure motif in the molecular recognition motif allows optimal molecular recognition by incorporating essential structural and chemical properties required for a specific type of analyte. For example, good solvent accessibility for easier access by analytes, good flexibility required for recognition, a special geometric pocket for the interaction, a hydrophilic surface or charged environment to facilitate the binding process and a required environment for the fast kinetic rates such as good off rate required for real time measurements.

Any exposed motifs with a good solvent accessibility and flexibility such as helix-loop-helix or partial motif is a good selection. These helix-loop-helix motifs can be from EF-hand motifs from calcium binding proteins such as calmodulin or trponic c, S100, or from nucleic binding motifs.

In an embodiment, the structural motifs can include the calcium binding motif with helix-loop-helix from one site of calmodulin. In addition, other structural motifs from calmodulin (total 4), other EF-hand proteins with EF-hand motifs (>3000), and from alpha-lactalbumin can be incorporated as well, as long as they contain the analyte binding/cleavage sequence in the motif by modification.

In addition, other structural motifs such as beta-loop-beta or beta-loop-helix, or coiled structures or domains and fragments that contain the cleavage sequence, and which are located at a sensitive location relative to the chromophore with the capability to alter the chromophore environment, can be used in embodiments of the present disclosure.

Sequences for various structural motifs are noted above in reference to Table A, FIG. 20A-D.

Targeting Motif

The target motif has an affinity for a target such as cells, tissue, chemicals, enzymes, organelles, sub-organelles, and the like. In general, the targeting motif can include, but is not limited to, polypeptides (e.g., proteins such as, but not limited to, antibodies (monoclonal or polyclonal)), nucleic acids (both monomeric and oligomeric), polysaccharides, sugars, fatty acids, steroids, purines, pyrimidines, ligands, or combinations thereof. The targeting motif has an affinity for one or more targets. In general, the target can include, but is not limited to, a cell type, a cell surface, extracellular space, intracellular space, an organelle, a sub-organelle, a tissue type, a tissue surface, the vascular, a polypeptide, a nucleic acid, a polysaccharide, a sugar, a fatty acid, a steroid, a purine, a pyrimidine, a hapten, a ligand, and the like, related to a condition, disease, or related biological event or other chemical, biochemical, and/or biological event of the sample or host.

In particular, the targeting motif can be specific or non-specific. The specific targeting moiety can be selected to have an affinity (e.g., an attraction to) for a target such as, but not limited to, a specific protein, a cell type, a receptor, a transporter, an antigen, and a saccharide (e.g., a monosaccharide, a disaccharide and a polysaccharide), as well as other molecules that can interact with the targeting moiety. The specific targeting moiety can include, but is not limited to, an antibody, a polypeptide, an aptamer, small molecules, and ligands, as well as other molecules that bind to the target.

The non-specific targeting moiety can be selected to do one or more of the following: enter a cell or a cell type, enter the vasculature, enter extracellular space, enter intracellular space, have an affinity for a cell surface, diffuse through a cell membrane, react with a non-specified moiety on the cell membrane, enter tumors due to leaky vasculature, and the like. In an embodiment, the non-specific targeting moiety can include a chemical, biochemical, or biological entity that facilitates the uptake of the probe into a cell. The non-specific targeting moiety can include, but is not limited to, cell penetrating peptides, polyaminoacid chains, small molecules, and peptide mimics.

The purified proteins can also be directly injected into the cells or cellular space to measure the analyte concentration. Sensor proteins selected from the SEQ ID NOs. 1-99 can be also used to measure analyte changes in vitro such as in solution.

The purified proteins can also function as a buffer or chelator to control the concentration of the analyte in vitro and in vivo.

Sequences for various targeting motifs are noted above in reference to Table A, FIGS. 20A-D.

Methods of Use

In general, analyte sensors or systems can be used in vivo and/or in vitro. In an embodiment, the analyte sensors or systems can be introduced into a system (e.g., inside a cell or outside a cell and/or to a host), the analyte sensors or systems can be expressed (e.g., using a vector or other appropriate expression system) in the system, and/or the analyte sensors or systems can be included in a transgenic animal or plant. In an embodiment, the analyte sensors or systems can be introduced into a cell, host, or organism in vivo. In another embodiment, the analyte sensor can include a specific signal peptide for the delivery of analyte sensor to different subcellular compartments (e.g., cytosol, nucleus, mitochondrial matrix, endoplasmic reticulum, golgi and peroxisome, and the like).

Embodiments of the present disclosure provide for methods of detecting and measuring analyte (e.g., calcium, lead, and/or lanthanide) activity. In an embodiment, the methods can include: introducing an analyte sensor into a system; allowing the analyte sensor to interact with the analyte of interest, which can interact with the analyte binding site of the analyte sensor; and detecting or measuring the fluorescent properties or changes. The analyte sensor can include any of the analyte sensors described herein. As the change in fluorescent activity of the analyte sensor is a proxy for the activity of the analyte of interest, this method provides a means for studying and evaluating analyte activity.

In another embodiment, the methods can include: introducing a plasmid containing an analyte sensor into a host cell by standard gene transfer methods; expressing the analyte sensor in the host cell; allowing the analyte sensor to interact with the analyte of interest, which can interact with the analyte binding site of the analyte sensor, and thereby detect or measure the fluorescent properties or changes. The analyte sensor can include any of the analyte sensors described herein. As the change in fluorescent activity of the analyte sensor is a proxy for the activity of the analyte of interest, this method provides a means for studying and evaluating analyte activity.

Embodiments of the present disclosure provide for methods of detecting and measuring pH change. In an embodiment, the methods can include: introducing an analyte sensor into a system; allowing the analyte sensor to interact with an analyte (e.g., calcium, lead, and/or lanthanide), which can interact with the analyte binding site of the analyte sensor; and detecting or measuring the fluorescent properties or changes, which can be correlated to a pH change.

Embodiments of the present disclosure provide for methods of controlling the concentration of one or more analytes (e.g., calcium, lead, and/or lanthanide). In an embodiment, the methods can include: introducing an analyte sensor into a system; allowing the analyte sensor to interact with the analyte, which can interact with the analyte binding site of the analyte sensor. The bonding of the analyte with the analyte controls the amount of analyte in the system (e.g., cell or host).

Samples useful with this disclosure include biological samples, environmental samples, or any other samples for which it is desired to determine whether a particular molecule is present therein. With some embodiments, the sample can include a living cell or a cell extract, which may be obtained from an animal (e.g., mammal or humans) or a plant. Alternatively, the cells can originate from or be derived from bacterial cells. Further, the cells may be obtained from a culture of such cells, for example, a cell line, or can be isolated from an organism. Where the method is performed using an intact living cell or a freshly isolated tissue or organ sample, the presence of a molecule of interest in living cells can be identified, thus providing a means to determine, for example, the intracellular compartmentalization of the molecule in real time. One of ordinary skill in the art may select a suitable sample without undue experimentation.

Methods for detecting with the analyte sensor or of a cell expressing containing an analyte sensor may include, for example, illuminating the analyte sensor or cell expressing the v sensor with an illumination source such that the analyte sensor or cell expressing the analyte sensor emits radiation. Such detection methods may use an illumination source such as an incandescent light source, a fluorescent light source, a halogen light source, sunlight, and other equivalent sources. When illuminated by such an illumination source, the analyte sensor will emit fluorescent light that may be detected by unaided optical observation or by other qualitative or quantitative methods. Suitable methods for measuring fluorescence of samples are known and understood by those with ordinary skill in the art.

Based on the fluorescence properties of the analyte sensor, a DNA construct of the analyte sensor may be inserted into a recombinant vector or any suitable vectors that may conveniently be subjected to recombinant DNA procedures. The specific vector can depend on the type of host cells. For example, recombinant DNA plasmid vectors, which can exist as an extrachromosomal entity, may be a suitable vector. Alternatively, the vector may be one that, when introduced into a host cell, is integrated into the host cell genome and replicates together with the chromosome(s) into which it has been integrated. Once the analyte sensor has been constructed, vectors comprising the fluorescent nucleic acid molecules may be formulated into a variety of compositions, such as solutions (for example, buffer solutions) to be used in transfecting host cells.

A fluorescent host protein or variant thereof can be linked to the molecule directly or indirectly, using any linkage that is stable under the conditions to which the protein-molecule complex is to be exposed. Thus, the fluorescent host protein and molecule can be linked via a chemical reaction between reactive groups present on the protein and molecule, or the linkage can be mediated by a linker moiety, which contains reactive groups specific for the fluorescent host protein and the molecule. It will be recognized that the appropriate conditions for linking the fluorescent host protein variant and the molecule are selected depending, for example, on the chemical nature of the molecule and the type of linkage desired. Where the molecule of interest is a polypeptide, a convenient means for linking a fluorescent host protein variant and the molecule is by expressing them as a fusion protein from a recombinant nucleic acid molecule, which includes a polynucleotide encoding, for example, a fluorescent host protein operatively linked to a polynucleotide encoding the polypeptide molecule.

The analyte sensor may be produced as chimeric proteins by recombinant DNA technology. Recombinant production of proteins including fluorescent host proteins involves expressing nucleic acids having sequences that encode the proteins. Nucleic acids encoding fluorescent host proteins can be obtained by methods known in the art. For example, a nucleic acid encoding the protein can be isolated by a polymerase chain reaction of DNA from *A. victoria* using primers based on the DNA sequence of *A. victoria* GFP. Mutant versions of fluorescent host proteins can be made by site-specific mutagenesis of other nucleic acids encoding fluorescent proteins, or by random mutagenesis caused by increasing the error rate of PCR of the original polynucleotide with 0.1 mM $MnCl_2$ and unbalanced nucleotide concentrations.

One advantage of the analyte sensor is that it can be relatively small. As a small protein sensor, it may be applied to measure calcium activity. The smaller size can allow expression in various organisms due to characteristics of fluorescent host protein expression which does not require cofactors. The analyte sensor also can easily targeted to different subcellular compartments with the help of signal peptides, which offers significant benefits for monitoring the analyte activity in various cellular compartments in real time in vivo. As such, the analyte sensor can be small, sensitive, and quantitative.

It is contemplated that embodiments of the present disclosure can be used to measure and characterize calcium activity associated with various diseases and disorders. For example, heart and bone diseases. In addition, they can be used in drug discovery.

Kits

This disclosure encompasses kits that include, but are not limited to, analyte sensor (e.g., proteins or polynucleotides), related agents that can facilitate the delivery of the protein to its desired destination and directions (written instructions for their use). The components listed above can be tailored to the particular biological event to be monitored as described herein. A kit for use in transfecting host cells may be assembled using the nucleic acid molecules encoding the analyte sensor, or for labeling target polypeptides with the analyte sensor. Host cell transfection kits may include at least one container containing one or more of the nucleic acid molecules encoding a analyte sensor (or a composition including one or more of the nucleic acid molecules or plasmids described above), which nucleic acid molecule preferably includes plasmid. The kit can further include appropriate buffers and reagents known in the art for administering various combinations of the components listed above to the host cell or host organism. The components of the present disclosure and carrier may be provided in solution or in lyophilized form. When the components of the kit are in lyophilized form, the kit may optionally contain a sterile and physiologically acceptable reconstitution medium such as water, saline, buffered saline, and the like.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

EXAMPLES

Now having described the embodiments of the disclosure, in general, the example describes some additional embodiments. While embodiments of present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Introduction $Ca^{2+}$ regulates numerous biological processes through spatio-temporal changes in the cytosolic $Ca^{2+}$ concentration and subsequent interactions with $Ca^{2+}$ binding proteins. The endoplasmic reticulum (ER) serves as an intracellular $Ca^{2+}$ store and plays an essential role in cytosolic $Ca^{2+}$ homeostasis. There is a strong need to develop $Ca^{2+}$ sensors capable of real-time quantitative $Ca^{2+}$ measurements in specific subcellular environments without using natural $Ca^{2+}$ binding proteins such as calmodulin, which themselves participate as signaling molecules in cells. In this Example, a strategy is described for creating such sensors by grafting a $Ca^{2+}$-binding motif into chromophore sensitive locations in green fluorescence protein. The engineered $Ca^{2+}$ sensors exhibit large ratiometric fluorescence and absorbance changes upon $Ca^{2+}$ binding with affinities corresponding to the $Ca^{2+}$ concentrations found in the ER ($K_d$ values range from 0.4-2 mM). In addition to characterizing the optical and metal binding properties of the newly developed $Ca^{2+}$ sensors with various spectroscopic methods, the kinetic properties were also examined using stopped-flow spectrofluorimetry to ensure accurate monitoring of dynamic $Ca^{2+}$ changes. The developed $Ca^{2+}$ sensor was successfully targeted to the ER of mammalian cell lines to monitor $Ca^{2+}$ changes occurring in this compartment in response to stimulation with agonists. It is envisioned that this class of $Ca^{2+}$ sensors can be modified further to measure $Ca^{2+}$ in other cellular compartments, providing tools to study the contribution of these compartments to cellular $Ca^{2+}$ signaling.

Materials and Methods

Construction of EGFP Based $Ca^{2+}$ Sensors.

The $Ca^{2+}$ binding motifs of CaM, loop-III (DKDGNGYISAAE) and EF hand motif (EEEIREAFRVFDKDGNGYISAAELRHVMTNL), were inserted into enhanced GFP (EGFP) as previously reported (*J Biotechnol* 119, 368-378, which is incorporated herein by reference) and the insertions were verified by automated DNA sequencing. In brief, the cDNA encoding the EGFP variant grafted with a $Ca^{2+}$ binding motif was cloned into bacterial and mammalian expression vectors between BamH I and EcoR I restriction enzyme sites. For bacterial expression, the vector pET28(a) with a 6×His-tag was utilized. For mammalian expression, the protein-encoding DNA was subcloned into a pcDNA3.1+ vector. The ER retention sequence, KDEL, was attached to the C-terminus and the ER targeting sequence of calreticulin (CRsig), MLLSVPLLLGLLGLAAAD, was attached to the N-terminus of the EGFP-based $Ca^{2+}$ sensors through PCR. The Kozak consensus sequence was placed at the N-terminus of the calreticulin sequence for the optimal initiation of protein expression in mammalian cells (Nature 388, 882-887, J Cell Biol 108, 229-241, each of which are incorporated herein by reference). DsRed2-ER (BD Biosciences Clontech), which contains CRsig and KDEL signal peptides at the N and C-terminals, respectively, was used as a marker for the ER in co-localization experiments. To improve the folding at 37° C., two additional mutations, M153T and V163A, were also added to the Ca$^{2+}$ sensors (Nature biotechnology 14, 315-319, Biochemistry 39, 12025-12032, each of which is incorporated herein by reference).

Expression and Purification of EGFP and its Variants.

EGFP and its variants were expressed in BL21 (DE3) *Escherichia coli* (*E. coli*). Cells were grown at 37° C. in LB medium containing 30 μg/ml kanamycin to an O.D.$_{.600}$>0.6 before protein induction with 0.2 mM Isopropyl β-D-thiogalactoside (IPTG). Since EGFP exhibits reduced fluorescence at 37° C. in vivo, high-level expression of the soluble mature form of EGFP was achieved by growing the cultures overnight in LB broth at 30° C. EGFP and its variants were purified by sonication of the cell pellet and centrifugation at 22,500×g for 20 min. The supernatant was injected into a fast performance liquid chromatography (FPLC) system, AKTAprime, connected to a Hitrap Ni$^{2+}$ chelating column (Amersham Biosciences). The protein was eluted from the column with a gradient of imidazole in 50 mM NaH$_2$PO$_4$/Na$_2$HPO$_4$ and 250 mM NaCl (pH 7.4) and identified by mass spectrometry. Imidazole was removed by dialysis against 10 mM Tris and 1 mM DTT (pH 7.4).

Ultra-Violet and Visible Absorption Spectroscopy.

Ultra-violet and visible (UV-VIS) absorption spectra of EGFP and its variants were determined with a Shimadzu UV-1601 Spectrophotometer. Protein concentration was determined by UV-VIS absorbance at 280 nm using the molar extinction coefficient of 21,890 M$^{-1}$ cm$^{-1}$ for EGFP-wt calculated from the contribution from aromatic residues (1 Trp and 11 Tyr) (5500 and 1490 M$^{-1}$ cm$^{-1}$ for Trp and Tyr, respectively). The extinction coefficients (at 398 nm or 490 nm) of the EGFP variants were obtained with the Eq. (1):

$$\varepsilon_P = \varepsilon_{P,280\ nm}\left(\frac{A_P}{A_{P,280\ nm}}\right) \quad (1)$$

in which, the $\varepsilon_p$ is the extinction coefficient at 398 nm or 490 nm of EGFP variants, $\varepsilon_{p,280\ nm}$ is the extinction coefficient at 280 nm of EGFP variants, $A_p$ is the absorption of EGFP variants at 398 nm or 490 nm, and $A_{p,280\ nm}$ is the absorption of EGFP variants at 280 nm. EGFP was used as a reference in the measurement of the extinction coefficients of the EGFP variants.

Fluorescence Spectroscopy.

The properties of EGFP and its variants were monitored using a Fluorescence Spectrophotometer (Photon Technology International, Inc.) with a 10 mm path length quartz cell at 20° C. Fluorescence spectra of the chromophore in proteins were measured in the emission region of 410 to 600 nm and 500 to 600 nm with 398 and 490 nm excitation wavelengths, respectively. The ratio of emission at 500 to 600 nm when excited at 398 and 490 nm as a function of Ca$^{2+}$ concentrations was utilized to calculate the apparent dissociation constant $K_d$ for Ca$^{2+}$ binding of various EGFP-based Ca$^{2+}$ sensors by fitting Eq 2 with a 1:1 metal binding equation:

$$f = \frac{([P]_T + [Ca]_T + K_d) - \sqrt{([P]_T + [Ca]_T + K_d)^2 - 4[P]_T[Ca]_T}}{2[P]_T} \quad (2)$$

in which f is the fraction of Ca$^{2+}$ bound protein, $[P]_T$ is the total protein concentration (mM), $[Ca]_T$ is the total Ca$^{2+}$ concentration (mM), and $K_d$ is the Ca$^{2+}$ dissociation constant of the protein. The fraction of the protein bound with Ca$^{2+}$ was calculated according to Eq 3:

$$f = \frac{R - R_{min}}{R_{max} - R_{min}} \quad (3)$$

in which $R_{min}$, R, $R_{max}$ are the fluorescence emission ratios (excited at 398 and 490 nm) or the amplitudes measured with a stopped-flow spectrofluorimeter for Ca$^{2+}$-free, Ca$^{2+}$-bound, and Ca$^{2+}$-saturated protein, respectively. The fluorescence emission ratio (excited at 398 and 490 nm) was obtained by fitting the data to Eq 4:

$$R = \frac{F_{(398\ nm)}}{F_{(490\ nm)}} \quad (4)$$

in which $F_{(398\ nm)}$ and $F_{(490\ nm)}$ are the integrated fluorescence intensities in the range of 500 to 600 nm excited at 398 and 490 nm, respectively. The dynamic range value of Ca$^{2+}$ sensors was calculated by dividing the fluorescence emission ratio excited at 398 and 490 nm of the Ca$^{2+}$ saturated state ($R_{max}$) with that of the Ca$^{2+}$-free state ($R_{min}$).

The apparent dissociation constant for Ca$^{2+}$ binding ($K_d$) of EGFP-based Ca$^{2+}$ sensors was also measured by competitive titration with Rhodamine-5N. Rhodamine-5N is a fluorescent dye (Molecular Probes) with a $K_d$ of 319±13 μM for Ca$^{2+}$ in 100 mM Tris, pH 7.4. The dye concentration was calculated using an extinction coefficient of 63,000 M$^{-1}$ cm$^{-1}$ at 552 nm. Measurements with different Ca$^{2+}$ concentrations were performed by maintaining the concentration of dye (10 uM) and protein constant. The fluorescence emission signal from 560 to 650 nm was measured with a cell of 1 cm path length excited at 552 nm. The slit widths of excitation and emission were set at 2 and 4 nm, respectively. The apparent dissociation constants were obtained by globally fitting the spectra from 560 to 650 nm using Specfit/32 with the metal and two ligand model (Spectrum Software Associates).

The Ca$^{2+}$ selectivity of the EGFP-based Ca$^{2+}$ sensor was examined by monitoring the change of the fluorescence ratio $F_{(398\ nm)}/F_{(490\ nm)}$ with 1.0 mM Ca$^{2+}$ in the presence of metal ions including 0.1 μM Cu$^{2+}$, 0.1 mM Zn$^{2+}$, 10.0 mM Mg$^{2+}$, 5.0 μM Tb$^{3+}$, or 5.0 μM La$^{3+}$. The normalized change of the ratio (ΔR) was calculated using Eq (5):

$$\Delta R = \frac{R_{metal} - R_0}{R_{Ca} - R_0} \times 100 \quad (5)$$

in which $R_0$ is ratio of the EGFP-based Ca$^{2+}$ sensor in the absence of Ca$^{2+}$ and metal ions, $R_{Ca}$ is the ratio of the EGFP-based Ca$^{2+}$ sensor with 1.0 mM Ca$^{2+}$ in the absence of metal ions, and $R_{metal}$ is the ratio of the EGFP-based Ca$^{2+}$ sensor with 1.0 mM Ca$^{2+}$ in the presence of the metal ions. Eq (5) was also used to examine the effect of small molecules including adenosine triphosphate (ATP), adenosine diphosphate (ADP), guanosine triphosphate (GTP), guanosine diphosphate (GDP), and Glutathione (GSH) on the Ca$^{2+}$ response of GFP-based Ca$^{2+}$ sensors. Data are expressed as a percentage.

Stopped-Flow Spectrofluorometry.

Stopped-flow kinetic measurements were performed on a Hi-Tech SF-61 stopped-flow spectrofluorometer (10 mm path length, dead time of <2 ms) with a 1:1 (v/v) ratio of the protein sensor and calcium at 20° C., as described previously (J Am Chem Soc 127, 2067-2074). Fluorescence emission changes associated with binding of $Ca^{2+}$ to Ca-G1 were determined by mixing $Ca^{2+}$ and Ca-G1 in 10 mM Tris and 1 mM DTT (pH 7.4) with excitation at 398 nm and a long-pass 455 nm filter. The concentrations of $Ca^{2+}$ ranged from 0 to 10 mM. Fluorescence emission changes associated with dissociation of $Ca^{2+}$ from Ca-G1 were measured upon mixing Ca-G1 preloaded with $Ca^{2+}$ in 10 mM Tris and 1 mM DTT (pH 7.4) with the same buffer. Generally, six duplicate measurements were carried out for each point and the last three were fitted to obtain the observed rate, $k_{obs}$. The $k_{obs}$ for each $Ca^{2+}$ concentration was obtained by fitting of the stopped-flow traces according to the single exponential function shown in Eq. 6:

$$F_t = F_0 + Amp[1-\exp(-k_{obs}t)] \quad (6)$$

in which $F_t$ is the fluorescence intensity at any stopped-flow time, $F_0$ is the initial fluorescence intensity, Amp is the final value of the fluorescence signal at the end of the process at a given $Ca^{2+}$ concentration, $k_0$ is the observed rate of fluorescence change ($s^{-1}$), and t is the reaction time (s). Measurements typically differed by less than 1% between duplicate experiments.

Cell Culture and Transfection.

Both BHK-21 and HeLa cells were grown on 100 mm culture dishes or glass coverslips ($0.5-1.0\times10^6$ cells/dish) in 35 mm culture dishes in Dulbecco's Modified Eagles Medium (DMEM, Sigma Chemical Co., St. Louis, Mo.) with 44 mM $NaHCO_3$, pH 7.2 and supplemented with 10% (v/v) Fetal Bovine Serum (FBS), 100 U/ml penicillin and 0.1 mg/ml streptomycin (Pen/Strep) at 37° C. with 5% $CO_2$ in a humidified incubation chamber. The cells were seeded and grown overnight before transient transfection with $Ca^{2+}$ sensor plasmid constructs.

Plasmid DNA used for transfection was harvested from transformed E. coli (DH5-☐) using a QIAGEN Miniprep protocol (Qiagen). Each of the GFP variants was individually and transiently transfected into BHK-21 and HeLa cells with Lipofectamine-2000 (Invitrogen Life Technologies) and serum-free Opti-MEMI (Gibco Invitrogen Corporation) per the manufacturer's instructions. The plasmid DNA (2 μg) with a ratio of DNA to Lipofectamine between 1:1 and 1:3 (μg/μl) was generally used in a typical transfection. Following incubation at 37° C. for 4 hrs, the medium containing the DNA-Lipofectamine complex was removed and replaced with DMEM enriched with FBS and Pen/Strep. The cells were then grown for 1 to 3 days in a humidified chamber with 5% $CO_2$ at 30 or 37° C. before fluorescence or confocal microscope imaging.

Confocal Microscope Imaging.

BHK-21 and HeLa cells were transferred from DMEM to Hank's Balanced Salt Solution without divalent cations (HBSS(—), Sigma Chemical Co., St. Louis, Mo.) media with 10 mM HEPES, 5 mM $NaHCO_3$, 1 mM EGTA, and pH 7.2 for live imaging experiments on a LSM 510 laser confocal microscope (Carl Zeiss Inc., Thornwood, N.Y.) using a 100× oil-immersion objective (Zeiss, Fluar, 1.30 n.a.). Prior to imaging, cells and buffers were brought to ambient temperature and allowed to equilibrate to room air. The localization of EGFP-based $Ca^{2+}$ sensors was visualized by excitation of EGFP with the 488 nm line of an Argon laser and the narrowest bandpass filter (505-530 nm) was employed for emission. DsRed2-ER was excited with the 543 nm line of a He—Ne laser, and emission was detected through a long-pass filter (emission above 560 nm). Zeiss LSM 510 software (Carl Zeiss, Inc.) was used to control the image acquisition parameters. All images were acquired at high resolution (1024× 1024).

Fluorescence Microscope Imaging and Its Quantification.

BHK-21 cells were imaged 1-3 days following transfection with GFP variants. A Nikon TE200 microscope running Metafluor software (Universal Imaging) with dual excitation capability was used for the cell imaging experiments (46). The ratio of fluorescence emission of EGFP-based $Ca^{2+}$ sensors (measured at 510 nm) in response to excitation wavelengths of 385 nm and 480 nm was measured to monitor changes in $[Ca^{2+}]_{ER}$ in time series experiments. The $[Ca^{2+}]_{ER}$ in BHK-21 cells was quantified according to Eq 7:

$$[Ca^{2+}] = K_d \times \left(\frac{R - R_{min}}{R_{max} - R}\right)^{\frac{1}{n}} \quad (7)$$

in which R is the fluorescent emission ratio (measured at 510 nm) for 385 nm/480 nm excitation at the initial state, $R_{min}$ is the minimum of the emission ratio determined at the $Ca^{2+}$-free state, $R_{max}$ is the maximum of the emission ratio at the $Ca^{2+}$-saturated state, $K_d$ is the apparent dissociation constant (mM) and n is the Hill coefficient (n=1). $Ca^{2+}$-free and $Ca^{2+}$-saturated states were obtained on cells treated with 5 μM ionomycin and exposed to 1.0 mM EGTA and 1.0 mM $Ca^{2+}$, respectively.

Results

Design of EGFP-Based $Ca^{2+}$ Sensors with a Single Inserted $Ca^{2+}$-Binding Motif.

FIG. 1 illustrates the design of $Ca^{2+}$ sensors made by grafting a $Ca^{2+}$-binding motif, a combination of CaM loop-III and its flanking helices, into EGFP based on the following criteria. First, $Ca^{2+}$-binding motifs such as loop-III or intact EF-hand motif III from CaM were used to create $Ca^{2+}$-binding sites in EGFP. $Ca^{2+}$ is chelated by 12-residues in the EF-hand motif. To our knowledge it has not been reported that peptide fragments of an EF-motif of CaM interact with any CaM target enzymes, thereby producing a sensor that is unlikely to interfere with cellular signaling events. Our previous studies have shown that the $Ca^{2+}$-binding affinity of the grafted loop can be varied by modifying charged residues in the loop and flanking helices (J Am Chem Soc 127, 3743-3750, J Inorg Biochem 99, 1376-1383, each of which are incorporated herein by reference), providing a convenient method to alter the $Ca^{2+}$ binding affinity of any designed sensor. Second, the locations in EGFP where the $Ca^{2+}$ binding motif is grafted should be in a solvent-exposed loop region and have good solvent accessibility to enable rapid $Ca^{2+}$ binding. Ideally, grafting of the $Ca^{2+}$ binding motif should not impact the protein folding and chromophore functionality. Third, in order to generate a $Ca^{2+}$-induced change in optical signal following $Ca^{2+}$ binding, the graft location should enable efficient $Ca^{2+}$-induced charge transfer from the grafted $Ca^{2+}$ binding motif to the fluorescent chromophore.

According to these criteria and previous mutation or permutation studies, three grafting sites were selected: Glu172-Asp173 within Loop-9 of EGFP (position 1), Gln157-Lys158 within Loop-8 (position 2), and Asn144-Tyr145 within Loop-7 (position 3). Loop-III of CaM, with or without the flanking helices, was used as a $Ca^{2+}$ binding motif and grafted at these positions to construct EGFP-based $Ca^{2+}$ sensors (FIG. 1A). Next, mutations M153T and V163A were inserted into construct Ca-G1 to create a sensor with improved expression at 37° C. (Ca-G1-37) (Nature biotechnology 14, 315-319, Biochemistry 39, 12025-12032, each of which are incorporated herein by reference). Finally, a construct with both ER targeting sequence and retention sequence, which specifically targets Ca-G1 to the ER of mammalian cells, was designed and is referred to as Ca-G1-ER.

Spectroscopic Properties of EGFP-Based $Ca^{2+}$ Sensors and Sensitive Locations of EGFP.

Spectroscopic properties of $Ca^{2+}$ sensors were first investigated using purified proteins (pH 7.4). FIGS. 2A and B show the visible absorbance and the fluorescence emission spectra of EGFP-wt and different $Ca^{2+}$ sensor constructs. The spectroscopic properties including extinction coefficients and quantum yields of $Ca^{2+}$ sensors are summarized in Table 1. The insertion of loop-III of CaM at Gln157-Lys158 of EGFP (Ca-G2' and Ca-G2 (only Ca-G2' is shown in FIGS. 2A and B), FIG. 1A) resulted in a protein with spectroscopic properties similar to EGFP-wt with a slight decrease in absorbance intensity. Note that the major absorbance peak at 490 nm and minor absorbance peak at 398 nm reflect the relative population of anionic and neutral states of the chromophore. FIG. 2B shows that excitation at 398 nm (the neutral state) contributed greatly to the emission peak at 510 nm. As summarized in Table 1, the constructs with a $Ca^{2+}$-binding motif grafted at Gln157-Lys158 (position 2) (Ca-G2' and Ca-G2) had spectroscopic properties (extinction coefficients and quantum yield constants at both 398 nm and 490 nm) similar to that of EGFP-wt. Strikingly, grafting loop III of CaM at Glu172-Asp173 of EGFP (Ca-G1') resulted in the formation of a protein which showed a slight increase of absorbance at 398 nm and a decrease of absorbance at 490 nm compared to EGFP-wt. Moreover, the insertion of loop III containing the flanking EF-helices at the same location (Ca-G1) resulted in a protein which had a further increase in absorbance at 398 nm and a decrease at 490 nm. The extinction coefficients of Ca-G1 were increased 2.6 fold at 398 nm and decreased about 60% at 490 nm compared to EGFP-wt. Concurrently, a corresponding increase in fluorescence emission was observed for both Ca-G1' and Ca-G1 (FIG. 2B). In contrast, the chromophore was not formed after insertion of loop III at Asn144-Tyr145 of EGFP (Ca-G3'), indicated by the lack of green fluorescence in the bacterial expression as well as in the purified protein. Thus, the grafting of a $Ca^{2+}$ binding motif at Glu172-Asp173 in EGFP significantly shifts the population of the chromophore from the anionic state as indicated by the 490 nm peak to the neutral state as indicated by 398 nm peak. It is likely that Glu172-Asp173 of EGFP is a chromophore sensitive location.

Figure 7:
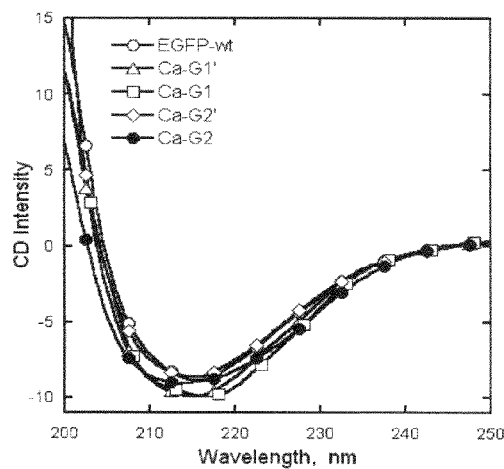
FIG. 7 illustrates CD spectra of EGFP-wt and its variants in 10 mM Tris and 1 mM DTT (pH 7.4). The protein concentrations were 10 μM for CD experiments with 1 mm cell length.
Figure 8:
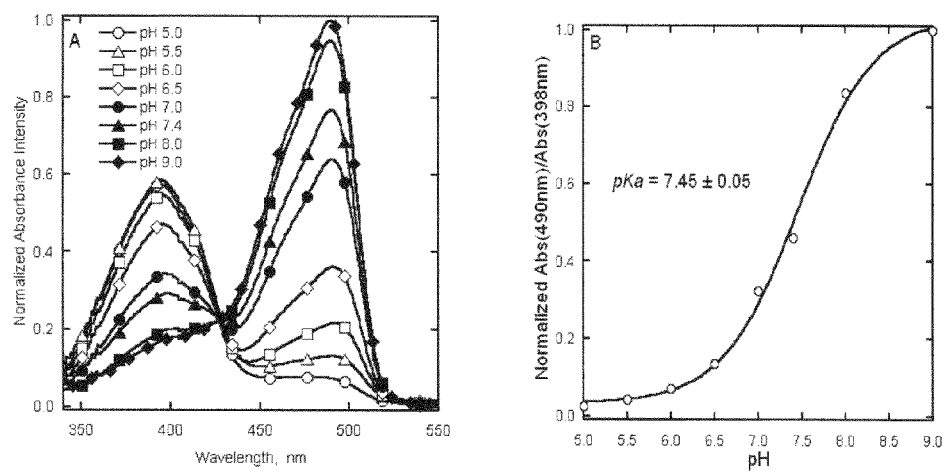
FIG. 8 illustrates the visible absorbance spectra FIG. 8A and its curve fitting (FIG. 8B) of Ca-G1' at different pHs. Symbols of different pHs are shown in FIG. 8A. The measurements were performed in 1 mM DTT and 10 mM MES (pH 5.0, 5.5, 6.0), 10 mM PIPES (pH 6.5, 7.0), and 10 mM Tris (pH 7.4, 8.0, 9.0). The protein concentrations were 10 μM for absorbance experiments. The length of the cell was 1 cm.

CD analysis was performed to test whether the changes in the chromophore properties of the $Ca^{2+}$ sensor constructs were due to structural changes. All $Ca^{2+}$ sensor constructs exhibited CD spectra similar to that of EGFP-wt (FIG. 7 in Supporting Information), suggesting that the insertion of a $Ca^{2+}$ binding motif into EGFP did not significantly change the folding of the β-sheet structure of GFP. Next, we examined the pH sensitivity of the optical properties of Ca-G1', since a few GFP-based biosensors have been reported to be pH sensitive. FIG. 8 shows the absorbance spectra of Ca-G1' as a function of pH. Changing pH from 9.0 to 5.0 resulted in an increase of the absorbance at 398 nm and a decrease of the absorbance at 488 nm. The $pK_a$ of Ca-G1' is 7.45±0.05 whereas the $pK_a$ of EGFP is 6.0. These data suggest that the optical properties of the designed $Ca^{2+}$ sensor are more sensitive to pH at physiological pH than those of EGFP-wt. Caution should be taken to maintain pH value when applying our sensor to measure calcium responses.

TABLE 1

Spectroscopic Properties of EGFP and $Ca^{2+}$ Sensor Constructs

| | Extinction coefficient | | | |
|---|---|---|---|---|
| | $\epsilon$ (398 nm)[a] | $\epsilon$ (490 nm) | $\epsilon$ (490 nm)/ $\epsilon$ (398 nm) | Quantum yield |
| EGFP[b] | 9.8 | 55.9 | 5.7 | 0.60 |
| Ca-G1' | 10.9 | 34.4 | 3.2 | 0.53 |
| Ca-G1 | 25.9 | 21.5 | 0.8 | 0.59 |
| Ca-G2' | 9.3 | 46.4 | 5.0 | 0.60 |
| Ca-G2 | 8.5 | 38.6 | 4.5 | 0.69 |
| Ca-G3'[c] | N/A[d] | N/A | N/A | N/A |

[a] $\epsilon$ is the extinction coefficient in units of $10^3$ $M^{-1}$ $cm^{-1}$. The wavelengths in absorption peaks are shown in the parentheses.
[b] EGFP-wt was used as a reference in the calculation of absorbance extincion coefficient ($\epsilon$) and fluorescent quantum yield of EGFP variants.
[c] The chromophore was not formed in Ca-G3'.
[d] N/A, not available.

Effect of $Ca^{2+}$ Binding on Spectroscopic Properties of EGFP-Based $Ca^{2+}$ Sensors.

As shown in FIG. 3A, an increase in absorbance at 398 nm concomitant with a decrease at 490 nm was observed in response to the addition of $Ca^{2+}$ to Ca-G1-37. Similarly, $Ca^{2+}$ binding resulted in an increase in fluorescence with excitation at 398 nm (FIG. 3B) and a decrease with excitation at 490 nm (FIG. 3C). The dynamic range value was 1.8 and was calculated by dividing the fluorescence emission ratio excited at 398 and 490 nm of the $Ca^{2+}$ saturated state ($R_{max}$) by that of the $Ca^{2+}$-free state ($R_{min}$) (see Experimental procedures). FIG. 3D shows the fluorescence emission ratio, $F_{(398\ nm)}/F_{(490\ nm)}$, of Ca-G1-37 as a function of $Ca^{2+}$ concentration. The normalized fluorescence emission ratio change could be fitted as a 1:1 Ca-G1-37-$Ca^{2+}$ complex (Eq 2), yielding an apparent dissociation constant ($K_d$=0.44±0.04 mM) for its $Ca^{2+}$ binding affinity. The $Ca^{2+}$ binding affinity of EGFP-based $Ca^{2+}$ sensors was also determined using a Rhodamine-5N competition titration approach. The $Ca^{2+}$ binding affinities of these $Ca^{2+}$ sensors varied from 0.4 to 2 mM (Table 2), as determined by different techniques. These values agreed well with the approximate [$Ca^{2+}$] found in cellular compartments such as the ER, making these $Ca^{2+}$ sensors promising candidates for physiological experiments in living cells.

TABLE 2

Comparison of $Ca^{2+}$ Binding Affinities of Different EGFP-based $Ca^{2+}$Sensors

| | $Ca^{2+}$ Binding Affinity, $K_d$ (mM) | |
|---|---|---|
| | $Ca^{2+}$ titration | Rhodamine-5N Competitive titration |
| Ca-G1' | 2.0 ± 0.4 | 0.9 ± 0.2 |
| Ca-G1 | 0.8 ± 0.1[a] | 0.4 ± 0.1 |
| | 0.8 ± 0.1[b] | |
| | 0.6 ± 0.1[c] | |
| Ca-G1-37 | 0.44 ± 0.04 | 0.2 ± 0.1 |
| Ca-G2' | N/A | 0.8 ± 0.2 |
| Ca-G2 | N/A | 0.2 ± 0.1 |
| Ca-G3' | N/A | 0.7 ± 0.2 |

[a] estimated with results of fluorescence spectrophotometer.
[b] estimated with fitting Scheme 1 using results from stopped-flow spectrofluorometer.
[c] estimated with fitting normalized changes (Amp) of stopped-flow spectrofluorimeter.

Ca²⁺ Selectivity of the EGFP-Based Ca²⁺ Sensor.

Figure 4:
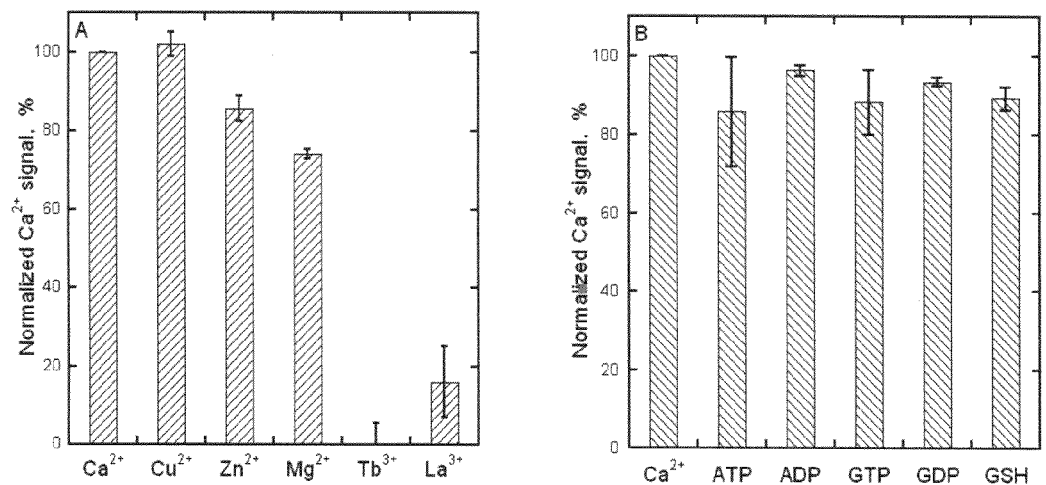
FIG. 4 illustrates $Ca^{2+}$ responses of Ca-G1-37 in the presence of different metal ions FIG. 4A $Cu^{2+}$ (0.1 μM), $Zn^{2+}$ (0.1 mM), $Mg^{2+}$ (10.0 mM), $Tb^{3+}$ (5.0 μM) and $La^{3+}$ (5.0 μM), and the intracellular molecules FIG. 4B ATP (0.2 mM), ADP (0.2 mM), GTP (0.1 mM), GDP (0.1 mM), and GSH (1.0 mM). The ratio of fluorescence emission of Ca-G1-37 with 398 nm and 490 nm excitation in the presence of 1.0 mM $Ca^{2+}$ was used to normalize the values obtained with the other metals or intracellular molecules using Eq (5). These measurements were performed using 1.7 μM Ca-G1-37 with 10 mM Tris and 1 mM DTT (pH 7.4). Excitation and emission slit widths were 1 and 2 nm, respectively.

We next examined the binding selectivity of our developed Ca²⁺ sensors for Ca²⁺ in experiments in which various other metal ions were used in a competition binding assay. Thus, the binding selectivity of our developed Ca²⁺ sensors for Ca²⁺ was examined by measuring the change of the ratio $F_{(398\ nm)}/F_{(490\ nm)}$ in the presence of 1.0 mM Ca²⁺ before and following the addition of various metal ions. In cells, total metal concentrations for Cu²⁺, Zn²⁺, and Mg²⁺ are estimated to be ~10 µM, ~0.1 mM, and >10 mM, respectively. However, the free levels of these metal ions are significantly lower than the total concentrations, which protects the cell against potentially toxic reactions (50). For example, intracellular free copper is not detected and copper chaperone is used in vivo to allocate copper to its target proteins directly. FIG. 4A shows the Ca²⁺ responses of sensor Ca-G1-37 in the presence of Cu²⁺, Zn²⁺, Mg²⁺, Tb³⁺, and La³⁺. Note that no effect of Cu²⁺ (0.1 µM) on the fluorescence response of the sensor for Ca²⁺ was observed (101.95±3.02% compared to the reference value of 100% for 1.0 mM Ca²⁺). Zn²⁺ (0.1 mM) and Mg²⁺ (10.0 mM) produced only a small change in the fluorescence response (reduction to 85.71±3.34% and 74.29±1.22%, respectively). Non-physiological metal ions, such as Tb³⁺ (5.0µM) and La³⁺ (5.0 µM) have metal coordination properties similar to Ca²⁺ and are able to compete more strongly with Ca²⁺ responses of the sensor (0.15±5.4% and 16.0±9.0%, respectively). These results suggest that the developed Ca²⁺ sensor, Ca-G1-37, has good metal selectivity for Ca²⁺, La³⁺ and Tb³⁺ and only to a lesser degree with the other physiological metal ions.

The effects of small molecules including adenosine triphosphate (ATP), adenosine diphosphate (ADP), guanosine triphosphate (GTP), guanosine diphosphate (GDP), and Glutathione (GSH) on the Ca²⁺ response of GFP-based Ca²⁺ sensors were also analyzed by measuring the change of the ratio $F_{(398\ nm)}/F_{(490\ nm)}$ in the presence of 1.0 mM Ca²⁺ before and following their addition. FIG. 4B indicates that the addition of ATP (0.2 mM), ADP (0.2 mM), GTP (0.1 mM), GDP (0.1 mM), and GSH (1.0 mM) only resulted in a small decrease in the fluorescence response (reduction to 85.75±13.98%, 96.17±1.36%, 88.30±8.09%, 93.29±1.01%, and 89.18±2.90%, respectively). These results indicate that the developed Ca²⁺ sensor, Ca-G1-37, has a high Ca²⁺ binding affinity to compete with small molecules including ATP, ADP, GTP, GDP, and GSH in the intracellular environment.

Kinetics of Ca²⁺ Binding to the EGFP-Based Ca²⁺ Sensor.

Figure 5:
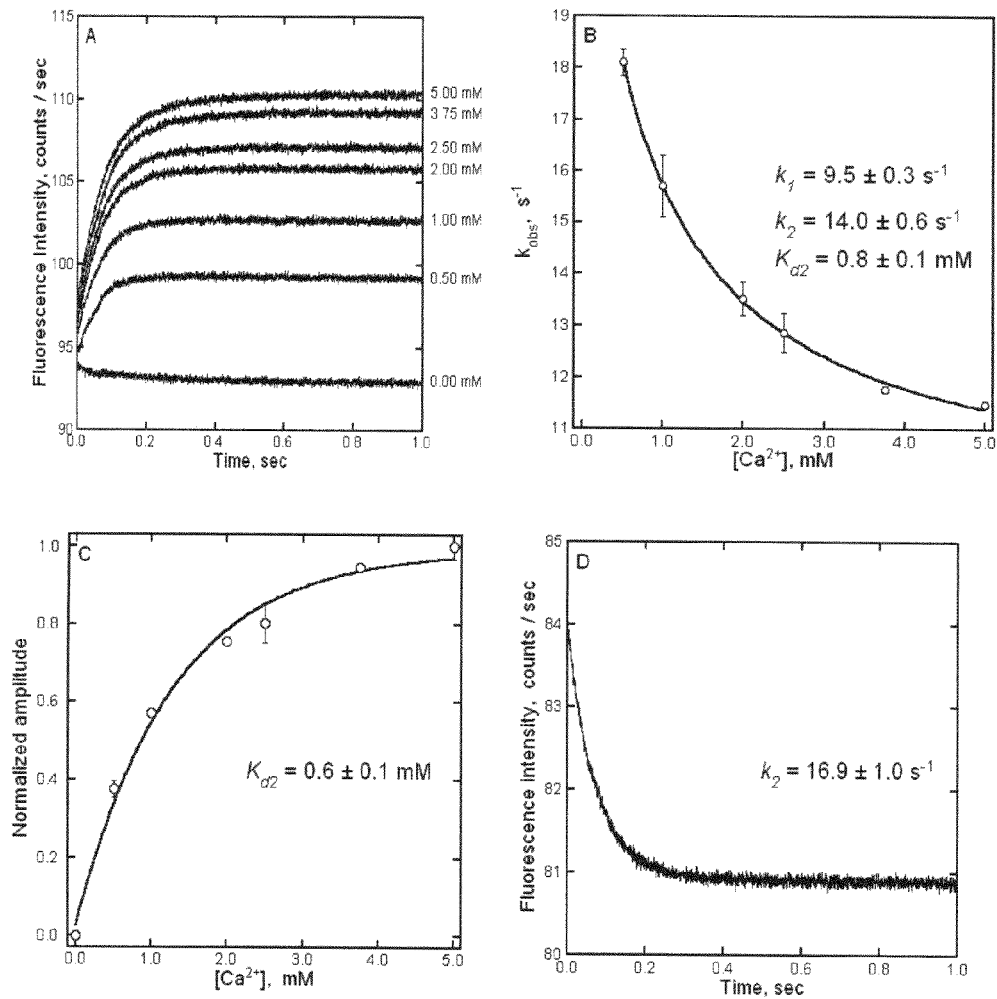
FIG. 5 illustrates a kinetic analysis of $Ca^{2+}$ association to Ca-G1.

As shown in FIG. 5A, mixing Ca-G1 with various concentrations of Ca²⁺ resulted in a rapid increase in the fluorescence emission at 510 nm with excitation at 398 nm. The change in fluorescence signal is consistent with a single exponential function (Eq 6) yielding observed rates for fluorescence emission change ($k_{obs}$) and amplitudes (Amp). As shown in FIG. 5B, the $k_{obs}$ values of Ca-G1 decreased with increasing concentration of Ca²⁺, consistent with the kinetic model of Scheme 1, in which Ca²⁺ rapidly associates with one species of Ca-G1 that is in equilibrium with a second form of the biosensor. The increases in fluorescence emission excited at 398 nm of Ca-G1 observed upon Ca²⁺ binding as shown in FIG. 5A further suggest that the neutral form of Ca-G1 is the species that binds Ca²⁺ (E** in Scheme 1), whereas the anionic form of the biosensor (E*) does not bind Ca²⁺. According to this kinetic model, $k_1$ is the first order rate constant (s⁻¹) for the conversion of the anionic species to the neutral species of Ca-G1, $k_2$ is first order rate constant (s⁻¹) for the conversion of the neutral species to the anionic form of Ca-G1, and $K_{d2}$ represents the apparent dissociation constant for the binding of Ca²⁺ to the neutral form of Ca-G1 (mM).

Scheme 1

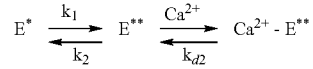

By fitting $k_{obs}$ values determined as a function of Ca²⁺ concentration to Eq 8, the $k_1$ and $k_2$ values were estimated to be 9.5±0.3 s⁻¹ and 14.0±0.6 s⁻¹, respectively, and a $K_{d2}$ value of 0.8±0.1 mM was determined. The $K_{d2}$ value was independently estimated to be 0.6±0.1 mM by fitting the normalized amplitude in fluorescence emission as a function of the concentration of Ca²⁺ by using Eq 2 (FIG. 5C). Within errors associated with the measurements, the $K_d$ values determined using stopped-flow fluorescence spectroscopy are in agreement with the $K_d$ value independently determined in static titrations using a spectrofluorometer, which yielded a $K_d$ value of 0.8±0.1 mM (Table 2). This, in turn, strongly supports the validity of the proposed minimal kinetic mechanism of Scheme 1 for Ca²⁺ binding to Ca-G1, where rates of fluorescence changes associated with Ca²⁺ binding to the neutral species of Ca-G1 reflect rates of interconversion of the neutral and anionic forms of Ca-G1, as compared to the rapid association and dissociation of Ca²⁺ to and from the biosensor.

$$k_{obs} = k_1 + k_2 \left( \frac{K_{d2}}{K_{d2} + [Ca^{2+}]} \right) \quad (8)$$

According to the minimal kinetic mechanism of Scheme 1 and the data shown in FIG. 5A, the release of Ca²⁺ from preloaded Ca-G1 is expected to be associated with a decrease in fluorescence whose rate of fluorescence change represents the slow rate of conversion from the neutral to the anionic form of Ca-G1, i.e., $k_2$. Consequently, stopped-flow spectroscopy was utilized to independently determine $k_2$ by mixing equal volumes of Ca²⁺-saturated sensor with 10 mM Tris and 1 mM DTT (pH 7.4). As expected, the fluorescence intensity at 510 nm decreased following Ca²⁺ release and the time course of fluorescence change was consistent with a single exponential process (Eq 6). As shown in FIG. 5D, a $k_{obs}$ value of 16.9±1.0 s⁻¹ was estimated in this experiment by fitting the data to Eq. 6, in good agreement with the value of 14 s⁻¹ determined for $k_2$ from the data in FIG. 5B. Together, the kinetic data support the conclusion that Ca²⁺ rapidly associates with and dissociates from the neutral form of Ca-G1, yielding a change in the relative amounts of neutral and anionic species that is associated with a change in the intensity of the fluorescence signal from Ca-G1.

Monitoring ER Ca²⁺ Responses in Cells.

Figure 6:
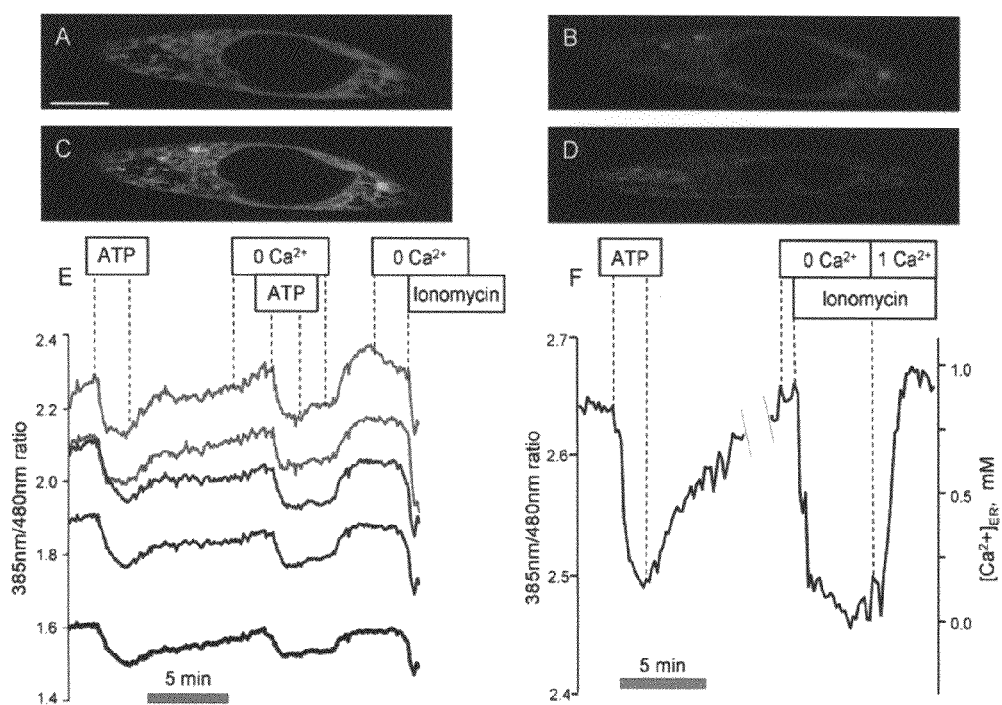
FIG. 6 Illustrates localization of the sensor Ca-G1-ER in two cell types (HeLa and BHK-21 cells) and Ca response of this sensor in BHK-21 cells. Localization of Ca-G1-ER FIG. 6A, DsRed2-ER FIG. 6B, and overlay of Ca-G1-ER and DsRed2-ER in HeLa cells, FIG. 6C. Localization of Ca-G1-ER in BHK-21 cell is shown in FIG. 6D. Confocal images of Ca-G1-ER and DsRed2-ER localization were performed with the 488 nm line of an argon laser for the green channel and the 543 nm line of a He—Ne laser for the red channel using a 100× oil immersion objective. The scale bar indicates 10 μm in panel FIG. 6A-6D. Time course of $Ca^{2+}$ responses in the ER of BHK-21 cells in response to different treatments is shown in FIG. 6E and pseudo calibration of $Ca^{2+}$ concentrations in the ER is shown in FIG. 6F. The time course of $Ca^{2+}$ signal response was expressed as the fluorescence emission ratio at 510 nm for excitation at 385 and 480 nm on a Nikon TE200 microscope running Metafluor software (Universal Imaging). The left-hand ordinate represents the 510 nm fluorescence emission ratio (excitation 385 and 480 nm) in both FIG. 6E and FIG. 6F, and the right-hand ordinate represents the calibrated $Ca^{2+}$ concentration in the ER in FIG. 6F.

Localization of the Ca²⁺ sensor, Ca-G1-ER, was confirmed in HeLa cells by co-transfecting the cells with the ER marker DsRed2-ER that has been shown to localize exclusively to this region in mammalian cells. FIG. 6 shows images taken through the green (A, Ca-G1-ER) and red (B, DsRed2-ER) channels which were excited at 488 and 543 nm, respectively. The yellow color seen in the merged image (FIG. 6C) indicates the complete co-localization of Ca-G1-ER with the ER marker DsRed2-ER in the ER of HeLa cells. FIG. 6D shows the ER distribution of Ca-G1-ER in a BHK-21 cell, a mammalian fibroblast cell line. Note the same granular distribution of Ca-G1-ER in FIGS. 6A and D, suggesting that the Ca²⁺ sensor also specifically localizes to the ER of BHK cells. In contrast, Ca-G1, which lacked the ER signal peptides, was expressed diffusely throughout the cytoplasm of the cells, thereby serving as a negative control (data not shown).

BHK-21 cells have been used previously to investigate the physiological roles of $[Ca^{2+}]_{ER}$ in intact cells by using small, low-affinity $Ca^{2+}$ indicators (46, 53). ATP (100 μM) is a $Ca^{2+}$-mobilizing agonist of this cell type and elicits $Ca^{2+}$ release from the ER through Ins(1,4,5)P$_3$-mediated pathways. As shown in FIG. 6E, the addition of ATP (100 μM) resulted in a significant decrease (7.3±0.6% relative change) in the fluorescence ratio measured at 510 nm (excitation at 385 and 480 nm). The experiment shows five representative cells imaged in the same experiment and the results are typical of results obtained in 5 independent experiments. This decrease of $[Ca^{2+}]_{ER}$ was also observed following application of ATP in $Ca^{2+}$-free buffer, suggesting that ATP released $Ca^{2+}$ from the ER independent of extracellular $Ca^{2+}$. The refilling of the $Ca^{2+}$ store required several minutes in the presence of normal extracellular $Ca^{2+}$ in the medium. Similarly, the addition of the $Ca^{2+}$ ionophore, ionomycin, under $Ca^{2+}$ free conditions significantly emptied the ER store as indicated by the decreased 385 nm/480 nm fluorescence ratio. To obtain an estimate of $[Ca^{2+}]_{ER}$, a pseudo-calibration was performed in BHK-21 cells using Eq 7 and a $K_d$ of 0.8 mM for Ca-G1 as shown in Table 2 (FIG. 6F). The 385 nm/480 nm fluorescence ratio decreased to a minimum value ($R_{min}$) following a wash with $Ca^{2+}$ free medium (EGTA) and the subsequent addition of ionomycin (~5 μM) to the $Ca^{2+}$-free medium (estimated to contain less than 10 nM $Ca^{2+}$ using the freeware program 'Bound and Determined'). The addition of millimolar extracellular $Ca^{2+}$ (~1 mM) resulted in a large increase in the $Ca^{2+}$ signal with a plateau that approached the saturation state with a maximum of 385 nm/480 nm fluorescence ratio ($R_{max}$). The initial $Ca^{2+}$ concentration in the ER of the BHK-21 cell was estimated to be less than 1 mM using Eq 7 and addition of ATP (100 μM) reduced $[Ca^{2+}]_{ER}$ to approximately 0.15 mM (FIG. 6F). As expected, no significant fluorescence signal change was observed in response to the above experimental protocol in cells transfected with the wild type control construct, EGFP-wt-ER (data not shown). These imaging experiments demonstrate the usefulness of this novel class of $Ca^{2+}$ sensors in living cells and it is anticipated that their future application will facilitate the investigation of the role of the ER in $Ca^{2+}$ signaling and $Ca^{2+}$ homeostasis.

Discussion

Creating $Ca^{2+}$ Binding EGFP Variants.

We have shown previously that when continuous $Ca^{2+}$ binding motifs are grafted into non-$Ca^{2+}$-binding host proteins, such as the cell adhesion protein CD2, the $Ca^{2+}$ binding motifs maintain their native $Ca^{2+}$ binding properties (Protein Eng 14, 1001-1013, Protein Eng 16, 429-434, each of which is incorporated herein by reference). This grafting approach has been applied to study isolated EF-hand motifs and to estimate their cooperativity. The $Ca^{2+}$ binding affinity of these motifs can be changed by varying the length of the glycine linker, attaching flanking helices, and changing the number of charged residues in the EF-loop. In the present Example, we demonstrate that the $Ca^{2+}$ binding motif grafted into EGFP also binds $Ca^{2+}$ and that the $Ca^{2+}$ binding affinity of this motif can be altered several fold (with $K_d$ ranging from 0.4 to 2 mM) depending on the presence or absence of flanking helices. Our results clearly demonstrate that EGFP-based sensors with different $Ca^{2+}$ binding affinities can be created by this grafting approach. Affinities of these sensors are very similar to those of $Ca^{2+}$ binding proteins found in the ER and the extracellular environment. For example, $Ca^{2+}$ binding proteins in the ER have a low $Ca^{2+}$ binding affinity corresponding to the sub-millimolar free resting $Ca^{2+}$ concentration in the ER lumen. Calreticulin, one of the most prominent $Ca^{2+}$ binding proteins in the ER lumen, binds $Ca^{2+}$ with low-affinity and high-capacity ($K_d$=2 mM, $B_{max}$=25 mol $Ca^{2+}$/mol protein) (56). Using competitive assays, we have also demonstrated that the developed $Ca^{2+}$ sensor has good metal selectivity for $Ca^{2+}$ over other physiological metal ions. Furthermore, the existence of small molecules including ATP, ADP, GTP, GDP, and GSH do not alter $Ca^{2+}$ sensing capability of the developed sensor.

Developing $Ca^{2+}$ Sensors at Chromophore-Sensitive Locations of a Fluorescent Protein.

As shown in FIG. 2, the grafting of a $Ca^{2+}$-binding motif into three different locations of EGFP results in different effects on the EGFP chromophore properties. Grafting the $Ca^{2+}$-binding motif at Asn144-Tyr145 (FIG. 1) resulted in the lack of chromophore formation, although the same site in the enhanced yellow fluorescent protein, EYFP, has been used to fuse CaM or a zinc finger domain to newly introduced termini. Grafting at Gln157-Lys158 had only a small effect on the chromophore properties, as this construct had similar extinction coefficients and quantum yield constants compared to that of EGFP-wt (Table 1). While previous studies have inserted either a pentapeptide, a hexapeptide, TEM1 β-lactamase, and CaM or a zinc finger domain at either Glu172-Asp173 or Gln157-Lys158, no detailed characterization of the effect on the chromophore properties were reported. Grafting $Ca^{2+}$ binding motifs between Glu172-Asp173 of EGFP, which is located about 20 Å from the chromophore, significantly altered the chromophore properties with an increase in the absorption spectrum at 398 nm and a decrease at 490 nm (FIG. 2A). Concurrently, there was a significant increase in the fluorescence emission at 510 nm with excitation at 398 nm. These changes suggest that grafting a $Ca^{2+}$ binding motif between Glu172-Asp173 of EGFP-wt shifts the chromophore equilibrium from the anionic to the neutral state. Further, $Ca^{2+}$ binding resulted in an increase in the absorption spectra at 398 nm and a decrease at 490 nm (FIG. 3A). Such changes in spectral properties permit ratiometric measurements of $Ca^{2+}$ concentrations using the fluorescence emission ratio monitored at 510 nm for excitation at 398 and 490 nm. Clearly, $Ca^{2+}$ binding to Ca-G1 promotes the protonation of the anionic form of this construct and increases the proportion of the neutral form of the chromophore (FIG. 1B). While the grafting location of the $Ca^{2+}$ binding motif at Glu172-Asp173 is not in the immediate neighboring environment of the chromophore, it nevertheless has a significant effect on the local conformation of the chromophore without disturbing the packing and folding of the protein. It is possible that $Ca^{2+}$ binding results in a change in the local environment of the chromophore, stabilizing it in the neutral state.

Rate Constants Associated with $Ca^{2+}$ Binding and Dissociation.

$Ca^{2+}$ binding to Ca-G1 results in a rapid shift of the chemical equilibrium of the chromophore between its anionic and neutral states (Scheme 1). This conclusion is supported by visible absorption, fluorescence emission, and stopped-flow fluorescence data. Both kinetic and thermodynamic parameters, including the forward and reverse rate constants for the interconversion of the anionic and neutral states of the chromophore, as well as the apparent dissociation constant for binding of $Ca^{2+}$ to Ca-G1 were determined using stopped-flow fluorescence measurements. This approach established that the rates of $Ca^{2+}$ association and dissociation to and from the sensor must be significantly larger than both the forward and reverse first-order rate constants that define the chemical equilibrium of the chromophore ($k_1$ and $k_2$ in Scheme 1), which are between ~10 and ~20 s$^{-1}$. The rate of $Ca^{2+}$ association to proteins is generally a diffusion-limited process with an on-rate ($k_{on}$) equal or greater than $1 \times 10^6$ M$^{-1}$ s$^{-1}$. Since the apparent dissociation constant for the Ca$^{2+}$ binding process determined in this study for Ca-G1 is ~0.8 mM for Ca-G1, an off-rate ($k_{off}$) of ~800 s$^{-1}$ can be estimated from $k_{off}=k_{on} \times K_d$. Whereas the on-rate of GFP-based Ca$^{2+}$ sensors is generally not the limiting factor in Ca$^{2+}$ measurements, the slow off-rate exhibited by Ca$^{2+}$ sensors limits their usefulness in monitoring changes in Ca$^{2+}$ concentration in vivo, especially for fast Ca$^{2+}$ oscillations. To overcome this limitation, an improvement of the off-rate constant $k_{off}$ to 256 s$^{-1}$ was obtained by redesigning the binding interface between calmodulin and its targeting peptide in GFP-based Ca$^{2+}$ sensors. Optimizing the protonation rate of the chromophore in GFP-based Ca$^{2+}$ sensors will provide a means to enhance further the accuracy with which Ca$^{2+}$ signals can be measured with high temporal resolution.

Ca$^{2+}$ Responses in the ER.

To understand the role of the ER in Ca$^{2+}$ signaling, many innovative studies have been conducted. Both ratiometric dyes such as Mag-fura-2 and non-ratiometric dyes such as Mag-fluo-4 with Ca$^{2+}$ binding affinities of ~50 µM have been used to measure the intraluminal Ca$^{2+}$ concentration in the ER. Hofer and colleagues were the first to report an estimate of the Ca$^{2+}$ concentration in the ER of BHK-21 cells, 188±21 µM. Pozzan and colleagues directly monitored the free Ca$^{2+}$ concentration in both ER and SR by targeting the Ca$^{2+}$ sensitive photoprotein aequorin to these compartments in cultured skeletal muscle myotubes and estimated the Ca$^{2+}$ concentration to be approximately 200 µM. The agonist-induced Ca$^{2+}$ response in the ER of HeLa cells was successfully monitored by Miyawaki et al. using GFP-pair Ca$^{2+}$ sensors with different Ca$^{2+}$ binding affinities, and [Ca$^{2+}$]$_{ER}$ was reported to be in the range of 60 to 400 µM. Later, a new generation of GFP-pair Ca$^{2+}$ sensors, named D1, was developed using both modified CaM and its binding peptide to monitor Ca$^{2+}$ oscillations in response to ATP in the ER of HeLa cells and to explore the effect of the antiapoptotic protein Bcl-2 on ER Ca$^{2+}$ of MCF-7 breast cancer epithelial cells. We have shown here that the EGFP-based Ca$^{2+}$ sensor Ca-G1-ER is able to monitor [Ca$^{2+}$]$_{ER}$ in BHK-21 cells after stimulation of cells with agonists or Ca$^{2+}$ ionophore. The Ca$^{2+}$ concentration in the ER of BHK cells was estimated to be less than 1.0 mM which is consistent with values reported previously.

The Advantage of this New Class of Ca$^{2+}$ Sensors Compared to Other GFP-Based Ca$^{2+}$ Sensors.

The fact that GFP and its derivatives are fluorescent and can be targeted easily to different cellular compartments has stimulated many efforts to develop GFP constructs as Ca$^{2+}$ sensors in vivo. Generally, two series of GFP-based Ca$^{2+}$ sensors have been developed. One is based on fluorescence resonance energy transfer (FRET) between two GFP variants following Ca$^{2+}$ binding to CaM, or more recently to TnC, resulting in the binding to a target peptide (M13 for CaM and TnI for TnC) and a subsequent change in distance between paired GFPs. Another series of GFP-based Ca$^{2+}$ sensors has been constructed by the insertion of CaM and its targeting peptide at defined locations within a single GFP molecule. The resulting constructs exhibit a change in fluorescence signal following binding of Ca$^{2+}$. All such GFP-based Ca$^{2+}$ sensors reported so far are based on a similar mechanism, namely using natural Ca$^{2+}$ binding proteins (e.g., CaM and TnC) to confer Ca$^{2+}$ sensitivity to a GFP-based sensor. However, there are three important concerns and limitations related to the application of these Ca$^{2+}$ sensors comprised of essential Ca$^{2+}$ binding proteins and their binding partners (e.g., CaM binding peptides). First, CaM is a ubiquitous signaling protein in mammalian cells and its concentration varies from several micromolar to millimolar levels depending on cell type, and sub-locations within cells. In the past few years, CaM has been reported to be associated with ion channels, pumps and gap junctions, and dynamic changes in Ca-CaM complex levels are an integral part of the cellular Ca$^{2+}$ signaling. Since expression of micromolar level of Ca$^{2+}$ sensors is generally required for cell imaging and this concentration is comparable to endogenous levels of CaM already present in the cell, this approach has the potential to interfere with Ca$^{2+}$ signaling. It has been reported that the overexpression of CaM in transgenic mice results in severe cardiac hypertrophy. Thus, it is possible that perturbation and/or alteration of the existing Ca$^{2+}$ signaling system in cells can result by the introduction of additional CaM and M13 peptides, or troponin C/I, as part of current Ca$^{2+}$ sensors.

Second, CaM is a versatile protein involved in the regulation of many important biological processes and has been found to associate with more than 300 different proteins. This class of GFP-based Ca$^{2+}$ sensors suffers from competition by endogenous CaM or TnC and/or its numerous target proteins within living cells, reducing the dynamic range of this class of Ca$^{2+}$ sensors. Because of these issues, numerous efforts have been made to increase dynamic range and reduce the competition with endogenous proteins, including V68L and Q69K mutations in yellow fluorescent protein (YFP), the modification of both CaM and its binding peptide, the insertion of CaM targeting peptides into CaM, replacement of YFP with its circularly permuted variant (cpYFP) or Venus and the replacement of CaM with other Ca$^{2+}$ binding proteins such as TnC.

Third, the sensing capability of these sensors is dependent on conformational changes associated with the cooperative Ca$^{2+}$ binding to four Ca$^{2+}$ binding sites. While CaM binds Ca$^{2+}$ in the range of 0.1-10 µM, several mutational efforts have been made to increase this range, but such attempts often resulted in multiple signal responses with a trade-off in dynamic range and required stringent calibration. Clearly, then, the development of Ca$^{2+}$ sensors that are not based on endogenous Ca$^{2+}$ binding proteins would be highly advantageous.

All cells and their subcellular compartments have mechanisms for regulating their pH in a steady-state level. For example, the cytoplasm has a fairly uniform pH range of 7.1~7.3, equivalent to the pH in the ER. An elegant study conducted by Kim and his colleagues reported that the pH in the endoplasmic reticulum of HeLa cells is maintained at 7.07±0.02 (mean SE) at rest and during calcium release. Using noninvasive measurements, fluorescence ratio imaging and two independent calibration procedures, they clearly demonstrate that both K$^+$ and H$^+$ activities within the ER are similar to that of the cytosol using nigericin and 140 mM K. Cells stimulated either with ATP, histamine, or lysophosphatidic acid exhibited increases of cytosolic Ca$^{2+}$ concentration by releasing Ca$^{2+}$ from the ER store. In contrast, parallel measurements indicated that the pH$_{ER}$ remained stable throughout the period of Ca$^{2+}$ release. These findings strongly support the assumption that our probe can be used to measure Ca$^{2+}$ release from the ER without interference from a significant change in the pH of the ER in response to cell stimulation A problem that plagues nearly all types of Ca$^{2+}$ sensors and probes, including the ones described here, is that of pH sensitivity. This is largely due to the fact that ligand atoms for Ca$^{2+}$ binding are highly-charged. Many GFP-based Ca$^{2+}$ sensors have been utilized to monitor Ca$^{2+}$ signals in vivo, although their pK$_a$s are also near physiological pH like our developed sensor here. The pH sensitivity of GFP variants presents a challenge for the development of GFP-based biosensors. The development of Yellow Fluorescence Protein (YFP) variants is an example of efforts to improve pH-resistance. The first generation of YFP, EYFP (GFP-Ser65Gly/Ser72Ala/Thr203Tyr), includes a tyrosine residue substituted at position Thr203 (T203Y). The π-π interaction between Tyr203 and the chromophore phenol ring results in a red-shift in both the excitation and emission wavelengths, resulting in a yellow fluorescent variant of GFP. The mutations in EYFP, however, resulted in a more pH-sensitive variant (pK$_a$=6.9) than that of GFP. A second-generation of EYFP (EYFP-Val68Leu/Gln69Lys) slightly improved its acid resistance with a pK$_a$ of about 6.4. Additionally, third-generation derivatives, Citrine (EYFP-Val68Leu/Gln69Met, pKa=5.7) and Verus (EYFP-Phe46Leu/Phe64Lue/Met153Thr/Val163Ala/Ser175Gly, pKa=6.0) (85) have a high pH-resistance. Another example of a GFP variant with high pH-resistance is cyan-green fluorescent protein (CGFP). The mutation T203Y in enhanced cyan fluorescent protein results in a decrease in pK$_a$ from ~6 to <4.0. Thus, it should be possible to improve the pH-sensitivity of our Ca$^{2+}$ sensors through specific mutations in the future.

Our strategy for developing Ca$^{2+}$ sensors by grafting only the Ca$^{2+}$-binding motif into a conformationally sensitive location of EGFP represents a new approach with several advantages. First, without using natural Ca$^{2+}$ binding proteins such as CaM/TnC and their numerous target proteins such as M13, kinases, etc., our approach eliminates interference due to competition with endogenous CaM/TnC and their target receptor proteins. To our knowledge, this is the first description of a GFP-based Ca$^{2+}$ sensor that uses neither a natural Ca$^{2+}$ binding protein such as CaM or TnC nor one of its numerous target proteins. Second, our sensor permits a fuller range of Ca$^{2+}$ responses to be recorded with minimal perturbation of the cell-intrinsic Ca$^{2+}$ signaling networks. Since the quantum yield of the sensors is comparable to EGFP-wt (Table 1), the expression of the sensor at micromolar concentration is usually sufficient to permit cellular imaging. The Ca$^{2+}$ buffer effect of the sensor is expected to be negligible, since the GFP sensor concentration is relatively low (~1 μM) compared to the Ca$^{2+}$ concentration in the ER (>100 μM). Third, by varying the Ca$^{2+}$ binding motifs through the addition of flanking EF-helices or glycine linkers, this grafting approach yields a specific range of biologically useful Ca$^{2+}$ affinities. Currently available sensors range in K$_d$ from ~0.2 μM to 0.5 mM. With a K$_d$ range of 0.4~2.0 mM, our sensors have the lowest affinity reported to date and their K$_d$ is well matched for measurements of Ca$^{2+}$ concentrations in cellular compartments containing high Ca$^{2+}$ concentration. Fourth, the newly developed sensors are ratiometric and not FRET-based, which may allow them to be used with a slightly wider range of secondary fluorophores that might otherwise overlap with the CFP excitation or YFP emission spectra of most FRET probes. The dynamic range of Ca-G1-37 is 1.8, which is comparable to the reported value of the YC2.1 series of Ca$^{2+}$ sensors. Given the unique versatility of our sensor, we envision that it can be further modified in dynamic range and pH sensitivity to be targeted to other cellular compartments in the future. This approach is envisioned to provide tools to study the contribution of the ER and other cellular compartments to cellular Ca$^{2+}$ signaling in a wide variety of cell types, under different physiological conditions, and in various disease states.

Supplemental Information
CD Structural Analysis of Ca$^{2+}$ Sensor Constructs

The structure of different Ca$^{2+}$ sensor constructs was analyzed with their CD spectra by comparing them to EGFP-wt. As shown in FIG. 7, β-sheet CD spectra were observed as a main secondary structure in EGFP-wt and its variants, indicating that the insertion of a Ca$^{2+}$ binding motif in EGFP did not significantly change the folding of EGFP β-sheet structure.

pH Sensitivity of Ca$^{2+}$ Sensor Constructs

FIG. 8 shows the two main peaks seen in visible absorbance spectra of Ca-G1', representing the neutral form at 398 nm and the anionic form at 490 nm. The intensity of the peaks is changed as a function of pH. The protonation of the chromophore was increased as the pH decreased from 9.0 to 5.0 as evidenced by the increase of the absorbance at 398 nm and the decrease of the absorbance at 490 nm. The isosbestic point of the two peaks was observed at approximately 430 nm from FIG. 8. The pK$_a$ (7.45±0.05) of Ca-G1' was estimated by curve-fitting the absorbance ratio change as a function of pH, which is different from that of EGFP (~6.0). These data suggest that the optical properties of the Ca$^{2+}$ sensor are more sensitive to the physiological pH than that of EGFP.

Example 2

Introduction

Green Fluorescent protein (GFP) from *Aequorea victoria* is a 238 residue protein that consists of an 11 stranded β-barrel wrapped around a single central helix. The protein assumes this "β-can" structure and completely buries its chromophore, which is formed from the tripeptide segment-S64-Y66-G67-(Annu Rev Biochem, 67, 509-544). GFP spontaneously forms the chromophore without the use of any external co-factors and does not undergo interference from fused proteins. This advantage has made it a target for use in a variety of applications in protein trafficking and folding, gene expression, and as sensors in living cells.

Extensive efforts have been devoted to further developing fluorescent proteins as analyte sensors for measuring the changes of calcium ions, zinc, oxidation potentials, protein interaction and enzyme activities. While FRET-based analyte sensors using two different fluorescent proteins have significantly advanced our understanding in cell biology and signal pathway, there is an increasing need to develop analyte sensors with better capability in translocation which is limited by two large fluorescent proteins as well as better optical capability at the cellular environment. Currently, the quantitative measurements by FRET based sensors often suffer from cellular perturbation and photobleaching.

Several different types of sensors have been developed by directly modifying the signal fluorescent proteins such as pH sensors that can measure cellular pH change, voltage-gate channel, and oxidation sensors were developed. Extensive efforts have also devoted for to develop calcium sensor. Mywaki et al. has created calcium sensor camgroo by creating permutation fluorescent proteins and insertion of calmodulin and its binding peptides. More than 30 mutations have been created and their calcium response and optical properties have been examined. The developed sensors has been widely applied many different biological fields although there is concern about perturbation of the calcium network when introducing essential calcium trigger proteins.

To further develop calcium sensors without utilizing natural calcium binding proteins, it is important to demonstrate the feasibility of designing and engineering calcium binding sites in fluorescent proteins without losing fluorescent proteins. Our lab has designed several discontinuous calcium binding sites in GFP using the common features of calcium binding sites in proteins (Biochemistry, 44, 8267-73; J Am Chem Soc. 127, 2085-2093; J Am Chem Soc. 125, 6165-6171). Oxygen atoms from charged residues of the carboxyl sidechain of Asp and Glu, sidechain oxygen of Asn and Gln, and the mainchain carbonyl from different portions of the protein frame form a discontinuous calcium binding site. We also introduced calcium binding motifs into GFP to test the effect of ligand binding sites on the optimal properties of the fluorescent protein (J Biotechnol, 119, 368-378; Biochemistry, 46, 12275-12288).

One of the major problems in engineering ligand binding sites in a fluorescent protein is the loss of fluorescent property upon mutation. Partly due to the native environment of jelly fish, temperatures greater than 30° C. cause a decrease in the folding efficiency of wild type GFP. Cycle three mutations (denoted as C3, F99S, M153T, and V163A) were among the first set of mutations from DNA shuffling to show increased fluorescence at 37° C.

While there are extensive applications of these thermally stable fluorescent proteins, the mechanism for the folding and the key factors that control the maturation of chromophores are yet to be clearly elucidated. It is not clear whether such mutations will also be able to assist the folding and maturation of the chromophore upon addition of ligand binding sites, especially calcium binding sites. It is also very important to know the differential effects of such modifications on bacterial and mammalian cells with different folding machinery. Therefore, incorporation of "folding mutations" and a quantification of their fluorescence increase will provide us with insight into future development of fluorescent protein-based calcium sensors for real time imaging of calcium signaling.

In the present example, we investigate the in vitro and in vivo folding of EGFP, and the design of two types of calcium binding sites into EGFP. The effects of cycle 3 mutations on the fluorescent intensity at different temperatures and at both bacterial and mammalian cells were examined. We show that, for the constructed EGFP variants, two of the cycle 3 mutations (M153T/V163A) are sufficient to produce fluorescence at 37° C. in both bacteria and mammalian cells. The decrease in fluorescent intensity that is seen in bacteria with the mutation F99S is not seen in EGFP, or in any of the mutants expressed in mammalian cells. This indicates that the constructed variants undergo different folding trajectories in bacteria versus mammalian cells that affect the fluorescent intensity. To obtain the differences between the constructed variants and EGFP, bacteria expressed protein was utilized to determine the extinction coefficient and quantum yield for each construct. The engineered proteins retain their calcium reporting ability with the incorporation of the mutations. Results from our studies provide insights into the engineering EGFP for particular functions, i.e. for calcium sensors.

Methods and Materials
Variant Constructs.

The GFP variant EGFP-D2 with a discontinuous calcium binding site (S2D, S86D, L194E), cycle 3 (F99S, M153T, V163A) mutations were made through site-directed mutagenesis with PCR and turbo pfu (Strategene) following the manufacturer's suggestions with EGFP (S65T, F64L, V22L, M218I, H231L) as the initial template. EGFP-G1 contains a continuous EF-hand $Ca^{2+}$ binding motif III which was inserted by several rounds of PCR utilizing turbo pfu. The primers were designed in house and purchased through Sigma-Genosys. The linear DNA was ligated with T4 DNA ligase (Promega) following the manufacturer's instructions, and the circular DNA was transformed into DH5α E. coli competent cells for DNA amplification. The variant DNA was verified by automated sequencing at the GSU core facility. The cDNA encoding the EGFP variants with BamH I and EcoR I restriction enzyme sites between the N and C terminals were subcloned into mammalian expression vector pcDNA3.1+, which utilizes a CMV promoter (Invitrogen).

Bacterial Expression and Purification.

The proteins were expressed in the vector pet28a (EMD Biosciences) with a 6× His-tag by BL21(DE3) E. coli and in LB-kanamycin (30 μg/mL). Expression was induced at an 0.0.600 of 0.6 with 0.2 mM IPTG and expression was allowed to continue for 21 hrs before the cells were harvested by centrifugation. For these studies, the temperature was controlled at both 30° C. and 37° C. after induction. The expression of EGFP and its variants was monitored with the fluorescence intensity at 510 with a Fluo-star instrument by an excitation wavelength of 488 nm.

Protein purification was carried out using an Amersham-Pharmacia 5 mL HiTrap chelating HP column charged with nickel. The cell pellets were resuspended in 20 mM Tris, 10 mM NaCl, 0.1% Triton X-100, pH 8.8 and sonicated. The cellular debris was removed by centrifugation and the protein was loaded onto the prepared HiTrap column connected to an Amersham-Pharmacia AktaPrime FPLC. After washing to remove contaminant proteins, the protein of interest was eluted with an imidazole gradient. Contaminant imidazole was removed by dialysis, and the protein was further purified using a HiTrap Q ion-exchange column (Amersham) with a NaCl gradient at pH 8.0. Protein purity was verified by SDS-PAGE.

Mammalian Cell Culture.

HeLa cells were grown on 60 mm culture dishes in Dulbecco's Modified Eagles Medium (DMEM, Sigma Chemical Co., St. Louis, Mo.) with 44 mM $NaHCO_3$, pH 7.2, and supplemented with 10% (v/v) fetal bovine serum (FBS), 100 U/ml penicillin and 0.1 mg/ml streptomycin (Pen/Strep) at 37° C. with 5% $CO_2$ humidified incubation chamber. HeLa cells were grown to confluency before transient transfection.

Plasmid DNA used for transfection was harvested from transformed E. coli (DH5-α) using QIAGEN's miniprep protocol (Qiagen). Each of the nine GFP variants were individually and transiently transfected into HeLa cells with Liptofectamine-2000 (Invitrogen Life Technologies) and serum-free Opti-MEMI (Gibco Invitrogen Corporation) as per the manufacturer's instructions. A typical transfection consisted of 1 or 2 μg plasmid DNA with a ratio of DNA to Lipto-fectamine between 1:1 and 1:3 (μg/μl) dependent upon the protein construct. Protein expression was allowed to proceed for 48 and 72 h before inverted epifluorescence imaging. Control transfections with EGFP were performed in the same conditions as each construct.

Measurement of Fluorescent Intensity.

Three 1 ml samples were collected at time points throughout the expression, and centrifuged at 14 K rpm for 3 min. The cell pellets were resuspended in 1 ml of Tris buffer at pH 7.4, and 200 μl was analyzed using a FLUOstar OPTIMA (BMG Labtech) plate reader with excitation filters of 390 and/or 460 nm and an emission filter at 510 nm.

Fluorescence Microscopy/Imaging and its Quantifications.

An inverted epifluorescence microscope (Zeiss Axiovert 200) was utilized for fluorescence intensity screening in vivo. The microscope is equipped with a Xenon Arc Lamp, filters for Sapphire GFP with 398 nm excitation and 510 nm emission, with standard DAPI, FITC, and Texas Red filters, and transmitted light. An Axiocam 5 CCD camera is connected to the microscope at a right angle to the stage, and Zeiss Axiovision Rel 4.3 software was used for data collection and analysis. The microscope is equipped with 10×, 20×, and 40× dry objectives. For the fluorescence intensity measurements of the different protein constructs with each set of mutations, the 40× dry objective was utilized with both the Sapphire GFP and FITC filters and exposure times ranging from 50 to 2000 ms. The images with exposure allowing for fluorescence intensity within the dynamic range were utilized for data analysis. The fluorescence intensity measured in this time range was a linear function of the exposure time. AxioVision LE Rel. 4.3 software (AxioCam HRc) was used to quantify the fluorescence excited at 398 nm or 480 nm of the HeLa cells transfected with various GFP variants. Both area and mean fluorescence intensity of transfected cells (n>20 cells per image) were measured and the total mean fluorescence intensity of cells in each imaged field was obtained with the calculation of Eq. (1):

$$F = \frac{\sum_{i=1}^{n} S_i F_i}{\sum_{i=1}^{n} S_i} \quad (1)$$

in which, F is the total mean fluorescence intensity excited at 398 nm or 480 nm of cells in each image, and n is the number of fluorescent cells. $S_i$ is the area of $i^{th}$ fluorescent cell and $F_i$ is the mean fluorescent intensity excited at 398 nm or 480 nm of $i^{th}$ fluorescent cell.

The total mean fluorescent intensity excited at 398 nm or 480 nm of the HeLa cells three days after transfection with EGFP-G1-C3 was used as a reference, and the fluorescence intensity excited at different wavelengths of the HeLa cells grown for different times with other GFP variants was expressed as a percentage of EGFP-G1-C3 fluorescence according to Eq. (2):

$$F' = \frac{F}{F_0} \times 100 \quad (2)$$

in which, the F' is the relative fluorescent intensity excited at 398 nm or 480 nm of the HeLa cells, F is the total mean fluorescence intensity excited at 398 nm or 480 nm of the HeLa cells, and $F_0$ is the total mean fluorescent intensity excited at 398 nm or 480 nm of the HeLa cells incubated for three days after transfection with EGFP-G1-C3.

Measurement of Ultra-Violet (UV) and Visible Absorption Spectrum.

Spectroscopic properties of EGFP and its variants were measured by UV and visible absorption spectra with a Shimadzu UV and Visible Light Spectrophotometer from 600 to 220 nm. The concentrations of the proteins were determined by UV-vis absorbance at 280 nm using the molar extinction coefficient of 21,890 $M^{-1}$ $cm^{-1}$ calculated from the contribution from aromatic residues (1 Trp and 11 Tyr) (5500 and 1490 $M^{-1}$ $cm^{-1}$ for Trp and Tyr, respectively). The extinction coefficient (398 nm or 490 nm) of the EGFP variants were obtained with the Eq. (3):

$$\varepsilon_P = \varepsilon_{P,280\ nm} \left( \frac{A_P}{A_{P,280\ nm}} \right) \quad (3)$$

in which, $\varepsilon_p$ is the extinction coefficient at 398 nm or 490 nm of EGFP variants, $\varepsilon_{p,280\ nm}$ is the extinction coefficient at 280 nm of EGFP variants, $A_p$ is the absorption of EGFP variants at 398 nm or 490 nm, and $A_{p,280\ nm}$ is the absorption of EGFP variants at 280 nm. EGFP was used as a reference in the measurement of the extinction coefficients of the variants.

Fluorescence Excitation and Emission Spectra.

Spectroscopic properties of EGFP and its variants were also monitored with their fluorescence spectra, measured in a Fluorescence Spectrophotometer (Hitachi Co. Ltd.) with a 1 cm path length quartz cell at room temperature and at 1 μM concentration in 10 mM Tris and 1 mM DTT (pH 7.4). Slit widths of 3 nm and 5 nm were used for excitation and emission, respectively. The quantum yield of EGFP variants with different excitation wavelengths was obtained with a calculation of equation Eq. (4):

$$\varphi_p = \varphi_r \left(\frac{A_r}{A_p}\right)\left(\frac{F_p}{F_r}\right)\left(\frac{n_p^2}{n_r^2}\right) \quad (4)$$

in which, $\phi_p$ is the relative quantum yield excited at 398 nm or 490 nm of EGFP variants; $\phi_r$ is the relative quantum yield excited at 398 nm or 490 nm of the reference sample; $A_p$ is the absorption of EGFP variants at 398 nm or 490 nm; $A_r$ is the absorption of the reference sample at 398 nm or 490 nm; $F_p$ is the integrated fluorescence intensity in the range of 500 nm to 600 nm excited at 398 nm or 490 nm of EGFP variants; $F_r$ is the integrated fluorescence intensity in the range of 500 nm to 600 nm excited at 398 nm or 490 nm of the reference sample; $n_p$ is the refractive index of EGFP variants; and $n_r$ is the refractive index of the reference sample. EGFP was used as the reference sample in the measurement of quantum yield of EGFP variants.

Statistical Analysis.

Statistical analysis was performed with the software package Super ANOVA (Abacus Concepts, Berkeley, Calif.). Values were expressed as mean±SEM. Control and treatment groups were compared by performing an analysis of variance (ANOVA). Fisher's Protected Least Significance Difference Test (Fisher's PLSD) was employed for post-hoc tests of statistical significance. Significance levels compared to day 1 are indicated as follows: *p≦0.05; p≦0.01; *p≦0.001.

Results

Design of EGFP-Based Calcium Binding Proteins in the Green Fluorescent Protein.

Figure 9:
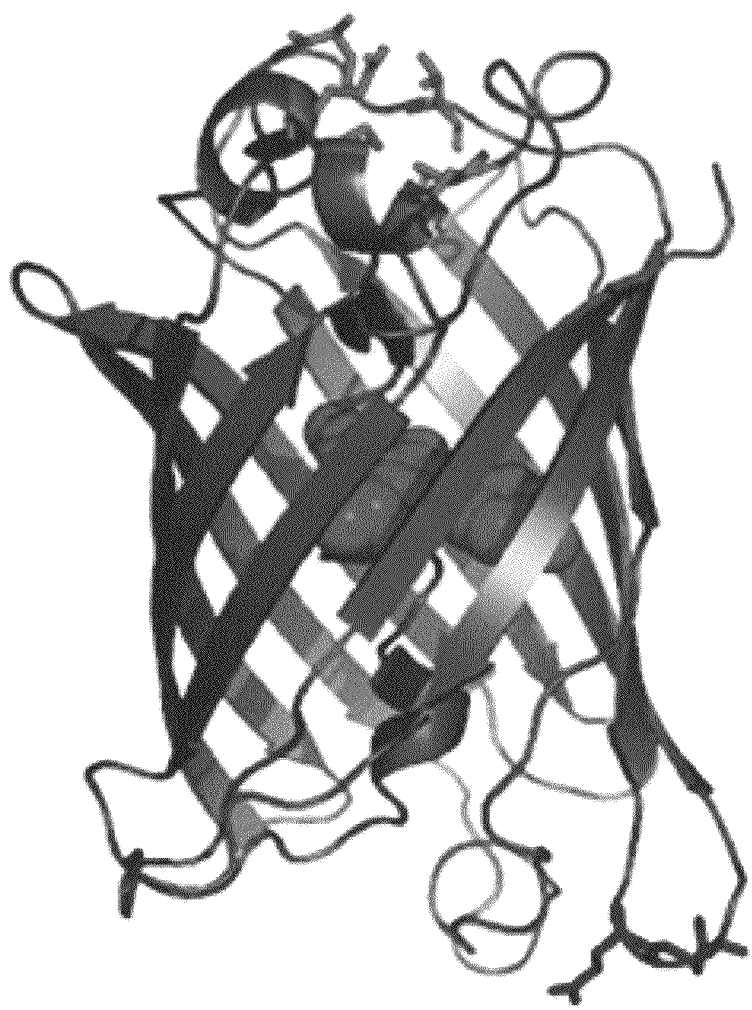
FIG. 9 illustrates model structure of calcium binding fluorescent protein with the addition of EGFP.D2 (site 1) (Red) by computational design or EGFP-G1, (172EF) by grafting the EF-hand motif III from calmodulin at position 172 (Blue). Residues involved in the formation of the chromophore are highlighted. The structure of EGFP around the chromophore based on 1 EMA.pdb.

Two different types of calcium binding sites were created in enhanced green fluorescent protein (EGFP). FIG. 9 shows the design of EGFP-D2 containing a discontinuous calcium binding site designed by our Metal Finder based on common pentagonal bipyramidal geometry and chemical properties (J Am Chem Soc. 127, 2085-2093; J Am Chem Soc. 125, 6165-6171). It is formed by oxygen from five negative charge ligand residues from sidechain carboxyl groups by mutated amino acids, S2D L194E, S86D, and the natural ligands of D82 and E5. FIG. 9 also shows the engineering of a continuous calcium binding site EGFP-G1 by grafting the EF hand calcium binding motif III of calmodulin inserted on loop 9 between residues E172-D173 of EGFP. In addition to fulfill the required criteria for calcium binding to have proper local calcium binding geometric properties and charge arrangement, we also selected these calcium binding sites based on the following additional criteria to assist chromophore formation. First, the site location and residue mutations should not abolish the chromophore synthesis or folding of the protein. Any residues that are conserved in fluorescent proteins and essential for protein structure and folding are not mutated. In addition, the location should be in a solvent-exposed region to have a good accessibility to enable calcium binding. Further, to avoid the drastic alteration of the protein folding and chromophore formation by introducing the charged calcium ligand residues, putative calcium binding pocket with less mutations required preferred. We also created additional mutants to test the effect of folding mutations on improvement of the fluorescence at both temperatures. The cycle 3 mutations were applied in sets of two or three of each calcium binding site to examine the differences in fluorescence in accordance with the applied mutations. Two mutations, M153T and V163A, were applied to EGFP-D2 and EGFP-G1 to create EGFP-D2-C2 and EGFP-G1-C2 constructs, respectively. The last mutation F99S was further incorporated to create the C3 constructs, EGFP-D2-C3 and EGFP-G1-C3. Same mutations C2 and C3 were also applied to EGFP-wt.

Bacteria Expression of the EGFP Calcium Binding Proteins.

Figure 10:
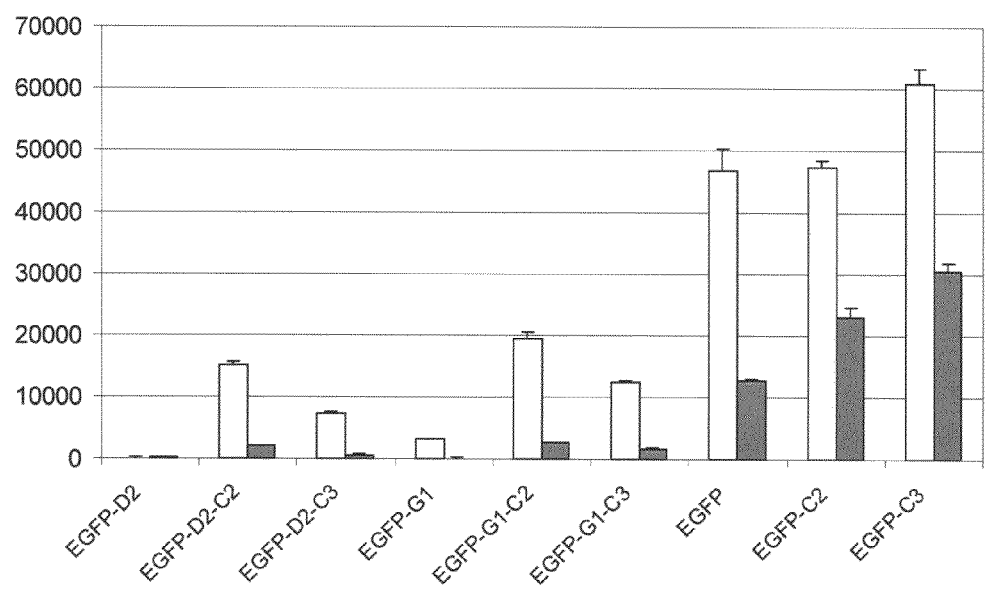
FIG. 10 illustrates the quantitative comparison of EGFP and its variant expression in *E. coli* bacteria (BL21-DE3) at 30° C. and 37° C., respectively. Fluorescent intensity at 510 nm of different cell pellets was monitored with a Fluo-star instrument for 22 hrs after 200 mM IPTG induction. $\lambda_{ex}$=488 nm.

The nine proteins, EGFP, EGFP-C2, EGFP-C3, EGFP-D2, EGFP-D2-C2, EGFP-D2-C3, EGFP-G1, EGFP-G1-C2, and EGFP-G1-C3 were first expressed in bacteria (BL 21) at both 30 and 37° C. to examine the differences in the chromophore maturation by monitoring the fluorescence intensity at 510 nm (excited at 490 nm) using fluorescent microplate (Material and methods). Average intensities of the nine proteins were taken in five time points throughout the expression. FIG. 10 only lists the average fluorescence intensities for 22 hrs after IPTG induction. The differences between the 30 and 37° C. expression fluorescence intensities were also calculated using the method described in the Material and Methods. As shown in FIG. 10, at 30° C. the addition of both types of calcium binding sites into EGFP does not alter the chromophore formation. On the other hand, the fluorescent intensities of expressed properties in bacteria were significantly decreased. The fluorescent intensities of both EGFP-D2 and EGFP-G1 is significantly low comparing that in EGFP at both 30° C. and 37° C. The C2 and C3 mutations in EGFP-D2 resulted in 37 and 18 fold increase of its fluorescence intensity at 30° C., respectively. The fluorescence intensity increase (6 and 4 fold) was also observed with C2 and C3 mutations in EGFP-G1 at 30° C. However, the similar fluorescence intensity increase was not observed with C2 and C3 mutations in EGFP at 30° C. The fluorescent intensities at 510 nm of the proteins with the addition of calcium binding sites D2 and G1 at 30° C. were greater than that at 37° C., respectively. While EGFP w.t. protein does not have any significantly difference in fluorescent intensity for both c2 and c3 variants, the c2 constructs for D2 and G1 surprisingly exhibited an increased fluorescence over the c3 variants. Though it is not as low in fluorescence as the protein variants with none of the cycle 3 mutations added, this indicates that F99S actually interferes with the folding of the protein variant when applied to the M153T/V163A construct Mammalian Cell Expression of EGFP-Based Calcium Binding Proteins.

Figure 11:
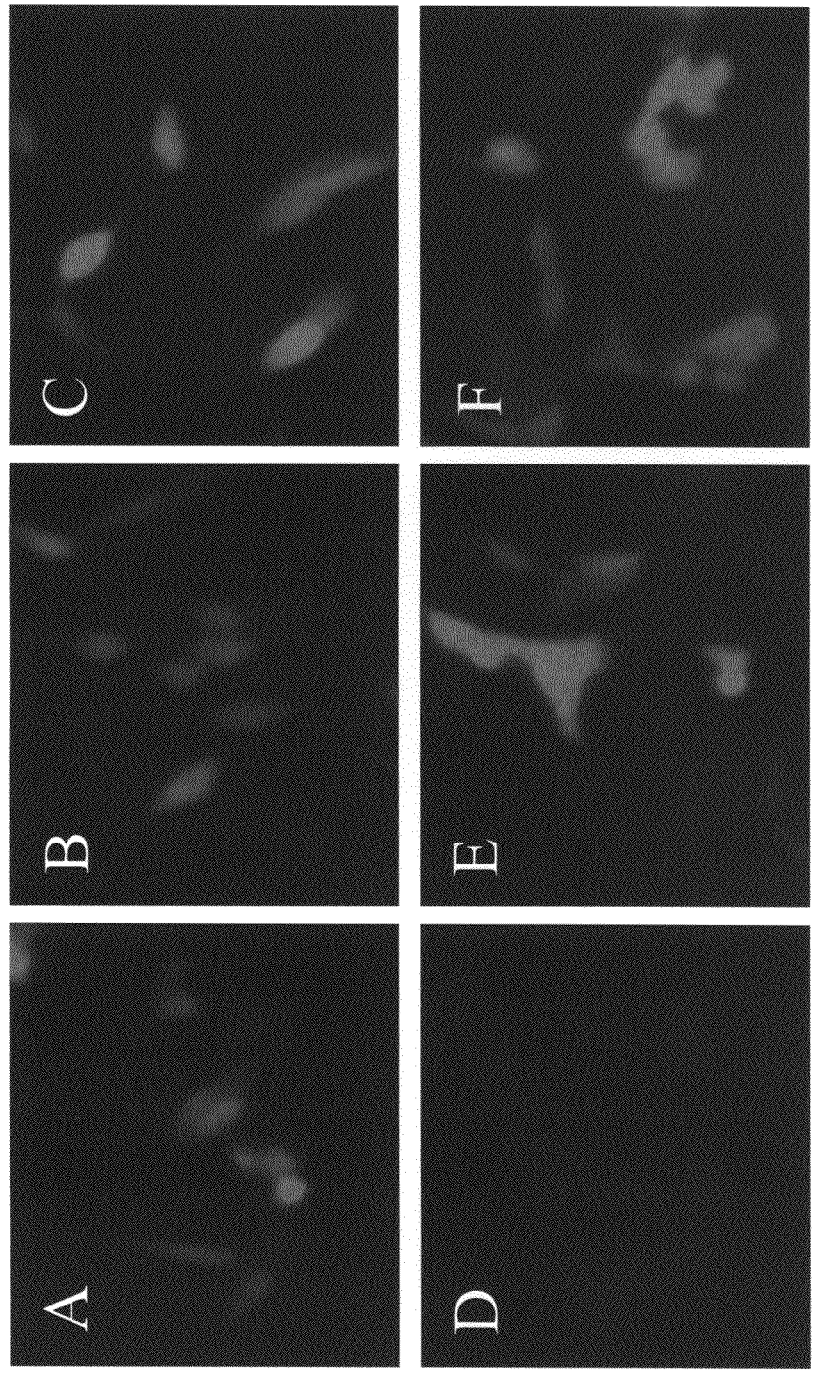
FIG. 11 illustrates a comparison of fluorescence microscope imaging of HeLa cells. The imaging was performed two days (48 hrs) after HeLa cells were transfected with EGFP-G1, EGFP-G1-C2, and EGFP-G1-C3. The exposure time was 200 ms.

The effect of C2 and C3 mutations on the expression of EGFP calcium proteins in mammalian cells was also monitored using fluorescence microscopy. FIG. 11 showed the fluorescence microscope imaging of the HeLa cells two days expression at 30° C. and 37° C. after transfection of EGFP-G1, EGFP-G1-C2, and EGFP-G1-C3. As shown in FIG. 11A-C, after two days transfection and expression at 30° C., EGFP-G1 variant and its C2 and C3 mutations were expressed and folded well in the majority of the HeLa cells as indicated by their strong fluorescence signals. However, FIG. 11D indicated that EGFP-G1 lost its fluorescence signal at 37° C. indicated that this temperature was not suitable to the maturation of EGFP-G1 in HeLa cells. In contrast, the addition of C2 and C3 mutations in EGFP-G1 resulted in a well maturation of the proteins at 37° C. in HeLa cells as shown in FIGS. 11E and 11F.

Figure 12:
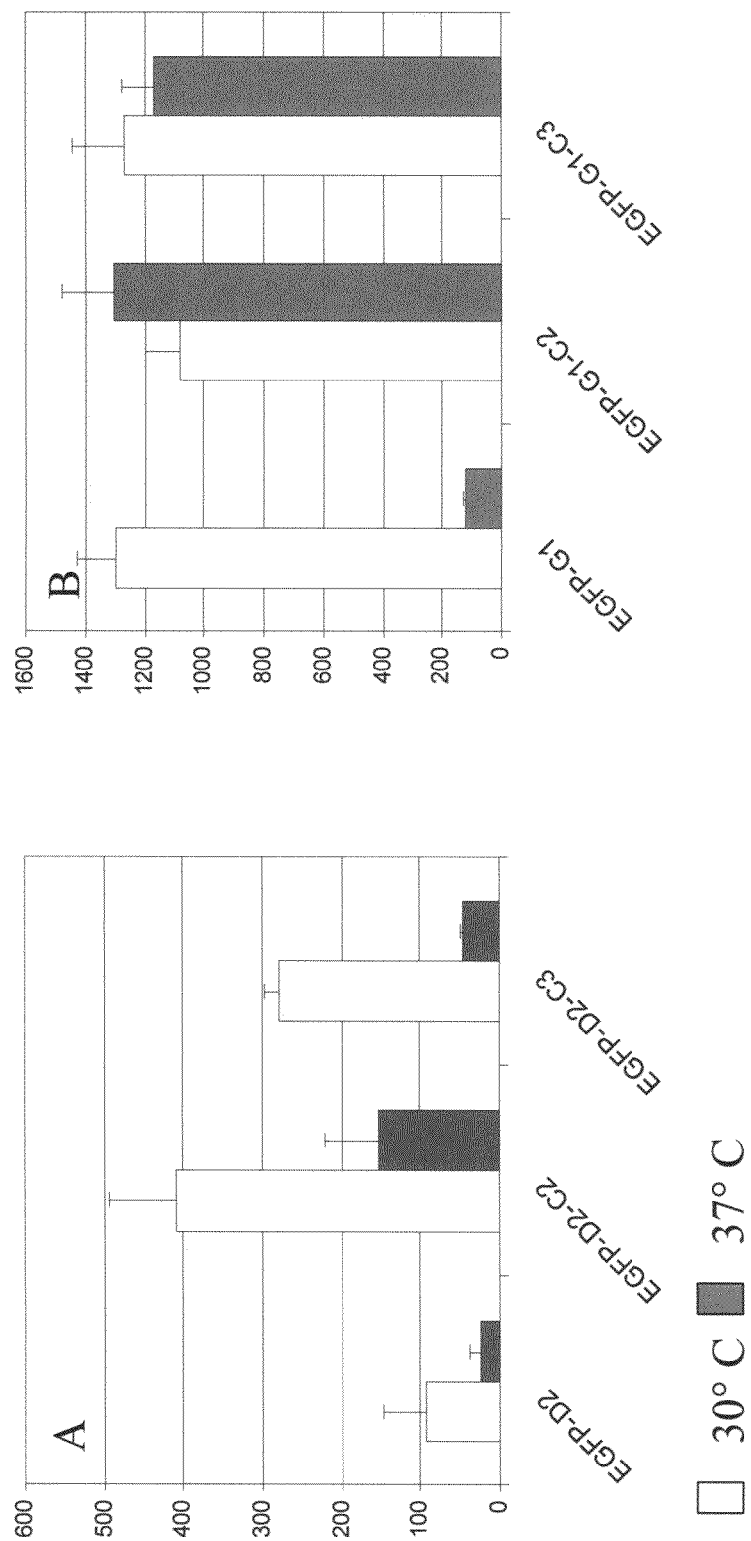
FIG. 12 illustrates a quantitative comparison of EGFP-D2 series FIG. 12A and EGFP-G1 series FIG. 12B expression in mammalian cells (HeLa) at 30° C. and 37° C., respectively. Fluorescent intensity at 510 nm of different cell pellets was obtained with fluorescence microscopy imaging for 2 days after transfection of different proteins. $\lambda_{ex}$=488 nm.

FIGS. 12A and B shows the quantitative analysis of fluorescence intensity of HeLa cells (more than 20 cells per image) transfected with both EGFP-D2 and EGFP-G1 series at both 30° C. and 37° C. A low fluorescence intensity of HeLa cells transfected with EGFP-D2 was observed in FIG. 12A at both 30° C. and 37° C. comparing that of EGFP-G1. C2 mutation in EGFP-D2 resulted in the increase of fluorescence intensity, but further increase was not observed in C3 mutation. This result in mammalian cells is corresponded with that observed in E coli. A similar result was also indicated with a C2 mutation in EGFP-G1 at 37° C. although the effect of C2 and C3 mutations of EGFP-G1 was not observed at 30° C. shown in FIG. 12B.

Spectroscopic Properties of the Calcium Binding GFPs.

To further explore this phenomenon, the proteins were then purified. Before undergoing purification the protein was extracted from the cell using sonication. Interestingly, EGFP-D2-C2 and EGFP-G1-C2 were much harder to purify due to the increase in concentration of the protein extracted. This indicates that the protein folds more efficiently and there were more soluble fractions that could easily be released during sonication. This was expected as EGFP-D2-C2 and EGFP-G1-C2 had 37 and 19 fold higher fluorescence than their counterparts with no "folding mutations".

Figure 13:
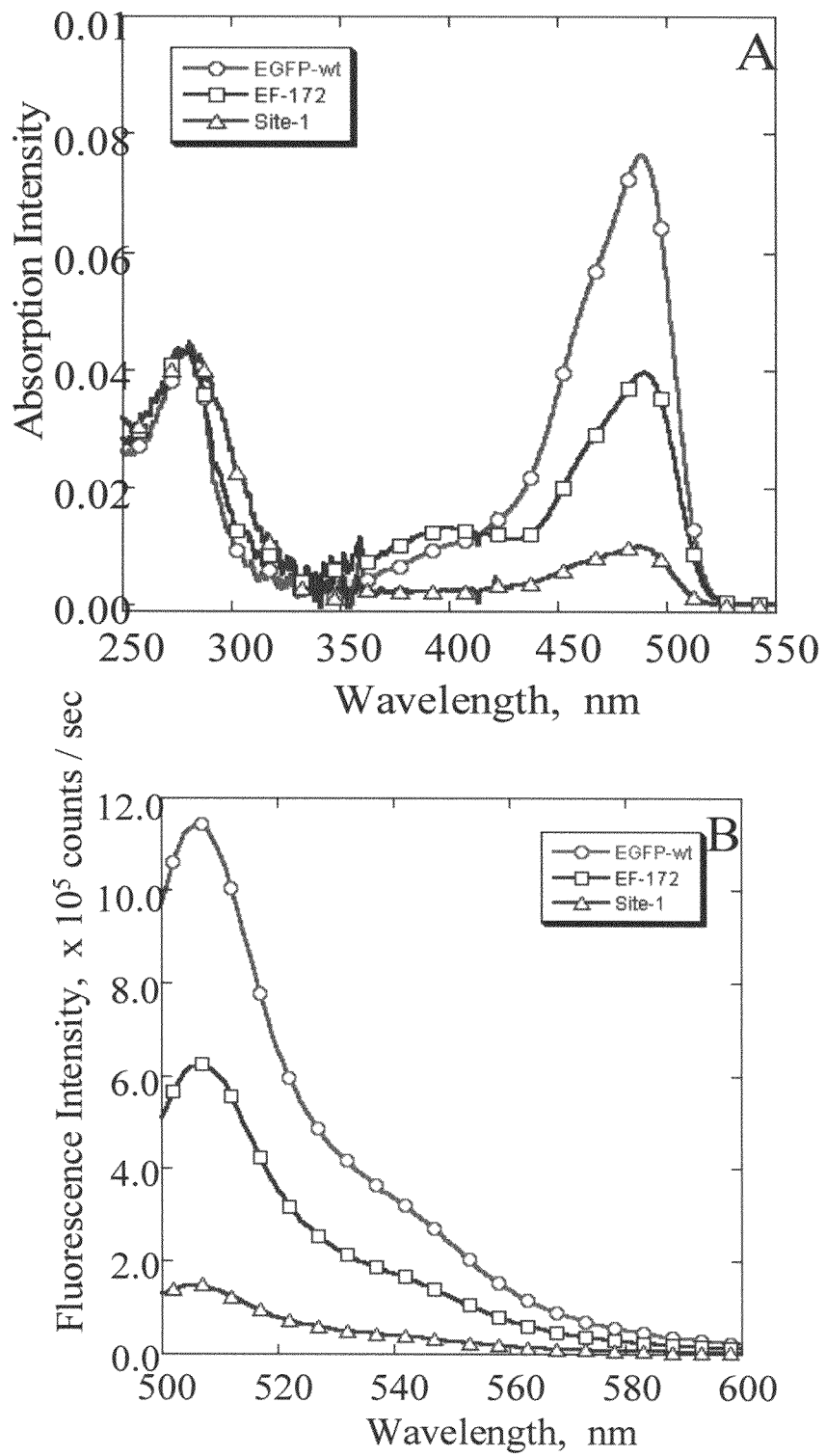
FIG. 13 illustrates the visible absorbance FIG. 13A and fluorescence FIG. 13B spectra of EGFP, EF-172, and Site 1. The measurements were performed in 10 mM Tris and 1 mM DTT (pH 7.4). The protein concentrations were 2 mM for both absorbance and fluorescence experiments. The length of the cell was 1 cm. The fluorescence experiments were performed with a slit width of 1 nm for both excitation and emission. $\lambda_{ex}$=488 nm.

Spectroscopic properties of EGFP-based $Ca^{2+}$ binding proteins developed with design and grafting approaches were then investigated using purified proteins. FIGS. 13A and 13B show the visible absorbance and fluorescence emission spectra of EGFP, EGFP-D2, and EGFP-G1 at pH 7.4. Table 1 in FIG. 14 is a summary of spectroscopic properties of EGFP, EGFP-D2, and EGFP-G1 and their C2 and C3 mutations. As shown in FIG. 13A, a major absorbance peak at 488 nm and a minor absorbance peak at 398 nm appeared in the visible spectra of EGFP, indicating that the anionic state of chromophore was the main form in EGFP. A fluorescence emission peak at 510 nm was observed in EGFP fluorescence spectrum (FIG. 13B). The similar spectroscopic properties including both extinction coefficients and quantum yield constant at 398 nm and 488 nm as summarized in Table 1 in FIG. 14 indicated that there is not effect of C2 and C3 mutations on the visible absorption spectra in EGFP-C2 and EGFP-C3. The formation of a $Ca^{2+}$-binding site by using three mutated ligands S2D, L194E and S86D and two natural ligands D82 and E5 of EGFP (EGFP-D2) resulted in a decrease of visible absorption at both 398 nm and 488 nm as observed in FIG. 13A. Comparing to EGFP, for example, the extinction coefficient at 488 nm of EGFP-D2 was decreased from 55900 $M^{-1}$ $cm^{-1}$ to 9324 $M^{-1}$ $cm^{-1}$. Concurrently, the fluorescence emission peak at 510 nm was decreased in its fluorescence spectrum (FIG. 13B) although the quantum yield of EGFP-D2 was almost same with that of EGFP. Strikingly, both C2 and C3 mutations in EGFP-D2 re-produced the major absorbance peak at 488 nm and minor absorbance peak at 398 nm similar to that of EGFP as indicated in Table 1 in FIG. 14. Taken together, while the quantum yield is significantly increased for EGFP variants with both types of calcium binding sites, the relative distribution of ionic-neutral states of the chromphore was not altered by the addition of folding mutations.

Example 3

As a secondary messenger, calcium ions regulate many biological processes in various intracellular compartments through interactions with proteins. Calcium is involved in muscle contraction (including heartbeat), vision, and neuronal signaling. Calcium binding proteins exhibit different calcium binding affinities with $K_d$ ranging from 0.1 µM to mM, which are essential for their response to various stimuli through the temporal and spatial changes of calcium and calcium homeostasis. For example, extracellular calcium-modulated proteins with multiple calcium binding sites, such as cadherins and calcium-sensing receptors, have dissociation constants in the submillimolar to millimolar range. Calsequestrin, a major calcium binding protein in the endoplasmic reticulum (ER), has a relatively weak calcium binding affinity that enables it to release or bind calcium in the ER calcium store. The endoplasmic reticulum (ER) with a resting $Ca^{2+}$ concentration varies from mM functions as the primary intracellular $Ca^{2+}$ store, which can produce both a synchronous $Ca^{2+}$ release and propagating $Ca^{2+}$ waves. $Ca^{2+}$-mobilizing agonists, such as ATP, histamine, and glutamine, and second messengers, such as $IP_3$ and cADPR, generate an increase in the cytosolic $Ca^{2+}$ concentration ($[Ca^{2+}]_c$) with a defined spatio-temporal pattern. The release of $Ca^{2+}$ from ER stores results in a rapid increase in $[Ca^{2+}]_c$ (from ~$10^{-7}$ M at the resting state to ~$10^{-6}$ M in the excited state), which, in turn, activates a number of intracellular $Ca^{2+}$ sensing (trigger) proteins, such as calmodulin (CaM), troponin C (TnC), and other ion channels and enzymes (Protein Sci, 7, 270-82). While the prevalence of calcium throughout the biological system is well-known and extensive efforts have been made, understanding the calcium regulation of biological functions, stability, folding, and dynamic properties of proteins is limited largely due to the calcium-dependent conformational changes and cooperative calcium binding in natural proteins.

The study of the key determinants of calcium binding has been an on-going endeavor for decades. There are several factors, such as the type, charge, and arrangement of the calcium ligands that have been shown to be important in calcium binding. Calcium is mainly chelated by the oxygen atoms from the sidechains of Asp, Asn, and Glu, the main-chain carbonyl, and solvent water molecules in proteins; and the pentagonal bipyramid geometry is the most popular binding geometry. Because of the electrostatic nature of calcium binding, charged Asp and Glu occur most often in calcium binding sites. The charge number in the coordination sphere also plays a role in calcium binding affinity. In addition, a more electronegative environment causes a stronger binding affinity for a given calcium site, and the electrostatic environment affects the cooperativity in multi-site systems. For these multi-site proteins, the apparent calcium affinity contains contributions from the metal-metal interactions and the cooperativity of the binding sites. Despite all of the information gleaned in the last 30 years, quantitative estimation of the key factors for calcium binding is yet to be established. Therefore, the systematic study of the key determinants for calcium binding requires a new strategy and model system.

To understand site specific calcium binding and key factors for calcium binding affinity, we have developed a design approach to engineer calcium binding sites into a non-calcium-binding domain 1 of the rat cell adhesion molecule CD2 (cluster of differentiation 2). Several calcium binding sites have been successfully engineered into this protein with a common Ig fold (Biochemistry, 44, 8267-73; J Am Chem Soc. 127, 2085-2093; J Am Chem Soc. 125, 6165-6171). However, it is not clear that our developed design approach can be widely applied to proteins with different scaffolds and how these general findings on the local factors on the calcium binding properties can be used. Monitoring the effects of calcium on the abundant cellular processes has, thus far, been a difficult endeavor due to numerous factors, such as interference from endogenous proteins and perturbation of original calcium signal pathways. While commercially available dyes with binding affinities ranging from 60 nM to hundreds of micromolar can be loaded into mammalian cells through simple incubation, they cannot be targeted to specific cell compartments in a predictable amount, causing difficulty in accurately determining the dye concentration and monitoring calcium concentration. Many of these dyes were shown to have buffering effect in cells and do not provide the necessary sensitivity for thick tissues, intact organisms, or non-mammalian cells. Protein-based calcium sensors that can be directly expressed by the cells and reliably targeted to specific subcompartments have been used in a wide variety of cell types, including mammalian and bacteria. Aequorin was first applied to monitor calcium responses at different cellular environments. Unfortunately, aequorin requires the constant addition of coelenterazine, which is consumed after each reaction. FRET-based calcium sensors were then developed using two differently colored fluorescent proteins or their variants linked with a calmdoulin binding peptide and calmodulin (Cell Calcium, 22, 209-216; Nature, 388, 882-887). To avoid using the essential trigger protein calmodulin, Troponin C (TnC) was used to sense calcium concentration change in the FRET pair of fluorescent proteins. To address the major concern regarding the competition of endogenous protein and the perturbation of the natural calcium signal systems using essential proteins such as calmodulin and troponin C and the potential pertatbation of the natural calcium signal network, Palmer et al. have carried out an elegant modification of calmodulin binding sites and calmodulin to reduce the interaction (Proc Natl Acad Sci USA, 101, 17404-17409; Chem Biol. 13, 521-530). Therefore, there is a strong need to develop calcium sensors without using natural calcium binding proteins to monitor the spatial and temporal changes of calcium in the cell, especially at high concentration organelles such as the ER.

In this study, we report our effort on the design of calcium-binding sites in GFP without using natural calcium binding motifs and as a biosensor to report calcium changes. The metal binding properties of several designed calcium binding sites and their optical properties are examined. In addition, the effects of integrating multiple charged residues on the chromophore formation or protein folding in different cellular systems (prokaryotes and eukaryotes) are investigated. We then further modified these designed calcium bind fluorescent proteins with increased brightness and thermostability with a $K_d$ for calcium of 107 µM. These designed proteins were shown to be able to express specifically in the ER of mammalian cells and to exhibit fluorescence changes in response to agonists such as ATP and CPA.

Methods

Computational Design.

The design of calcium-binding sites used the GFPc3 structure, 1b9c, due to its 30,000-fold greater fluorescence than wild type GFP with expression at 37° C. The potential calcium binding sites were computationally constructed with the desired oxygen-calcium-oxygen angle, oxygen-calcium distance, ligand type, and number of ligands. One anchor Asp and four additional potential ligands from Asp, Asn, Glu, or the backbone were utilized. The calcium-oxygen length was in the range of 2.0 to 3.0 Å. The oxygen-calcium-oxygen angles ranged ±45° from the theoretical angles of the ideal pentagonal bipyramid geometry (Biochemistry, 44, 8267-73; J Am Chem Soc. 127, 2085-2093; J Am Chem Soc. 125, 6165-6171). The selection of designed calcium binding sites was refined with the in-house-developed program Proteus.

Cloning and Purification of GFP Variants.

Site-directed mutagenesis was carried out by the classical polymerase chain reaction with pfu or turbo pfu (Invitrogen) and with EGFP DNA as the initial template. All primers were designed in-house and were purchased from Sigma-Genosys or Operon. The forward primer sequence is 5'-ACGGC-GACGCGAACCTCGCCGACC-3', and the reverse sequence is 5% CCTCGTCGTTGTGGCGGATCTTG-3'. For PCR, pfu polymerase was used, following the manufacturer's instructions with an annealing temperature of 60° C. The linear DNA was ligated with T4 DNA ligase (Promega), and the circular DNA was amplified in E. coli (either DH5a or Top10) competent cells. The mutations to engineer 177c3 included the above mutations, with the addition of F99S, M153T, and V163A, known as cycle3. The F99S primers were 5'-CGCACCATCTCCTTCAAGGACG-3' for the forward and 5'-CTCCTGGACGTAGCCTTCCC-3' for the reverse. M153T and V163A were made, together with the forward primer 5% GAACGGCATCAAGGCGAACT-TCAA-3' and the reverse primer 5'-TTCTGCTTGTCGGC-CGTGATATAGA-3'. The mutations were carried out utilizing turbo pfu (Stratagene), following the manufacturer's protocol with annealing temperatures of 61° C. for F99S and 63° C. for 153/163. The DNA was purified with a Qiagen Miniprep kit, and the circular variant DNA was verified by automated sequencing at the GSU core facility.

The vector pcDNA3.1+ (Invitrogen) was utilized during the mutagenesis and for the expression of the protein in mammalian cells in the cytosol. For expression of the protein in the ER, the pcDNA3.1+ vector was modified through PCR to contain the calreticulin signal peptide at the N-terminus of the protein and the KDEL retention sequence at the C-terminus. The N-terminal tag from calreticulin, MLLSVPLLLGLLG-LAAAD, directs the expression of the gene to commence in the ER. The C-terminal tag, KDEL, is a retention sequence that retains the expressed protein in the ER and does not allow it to be shuffled to the Golgi. The N-terminus tag was inserted in two rounds of PCR with four primers due to its length. Table 1, FIG. 19, illustrates the primers and strategy.

The proteins were expressed fused to a 6× histidine tag with a pet28a vector (EMD Biosciences) in Luria-Bertani medium containing 30 μg/mL kanamycin. Protein expression was induced at an $OD_{600}$ of 0.6 with 0.2 mM IPTG, and growth was continued for 3-4 hr before harvesting by centrifugation at 9500 g for 20 min. After breaking the cells with sonication, the proteins were dissolved with 8 M urea. The denatured protein was refolded by 10× dilution into the buffer (10 mM Tris, 1 mM DTT, 1% glycerol, pH 7.4) and was centrifuged to remove cellular debris. The refolded protein was purified using Sephadex G-75 size exclusion FPLC (10 mM Tris, pH 7.3) to >95% purity. The expression and purity of the protein were analyzed by SDS-PAGE. The protein concentration was estimated using a calculated extinction coefficient of 21,890 $M^{-1}$ $cm^{-1}$ at 280 nm. The histidine tag used for purification does not have any effect on calcium and terbium binding (unpublished data).

Terbium Fluorescence.

All buffers for the metal binding and conformational analysis studies in this work were pretreated with Chelex-100 Resin (Bio-Rad). The terbium binding of the proteins was measured with a PTI fluorimeter following the emission at 545 nm with an excitation at 280 nm. For terbium titration, the initial protein concentration was 3 μM in 20 mM PIPES, 10 mM KCl, 1 mM DTT, 1% glycerol, pH 6.8, for proteins GFP.Ca1-3 and 10 mM Tris, 1 mM DTT, 1% glycerol, pH 7.4 for GFP.Ca2". A 1.0 or 5.0 mM stock terbium containing the same concentration of protein was added directly into the protein samples. Blank samples consisted of the buffer with increasing terbium without protein. The data were baseline corrected, and the integrated area of the peak at 545 nm was fitted by assuming a 1:1 terbium:protein binding (J Am Chem Soc. 125, 6165-6171). The data were also analyzed using Specfit/32 (Talanta, 33, 943). Each binding affinity is an average of 4 to 6 titrations. To investigate the metal selectivity, GFP.Ca1 and GFP.Ca2' (3 μM) with 20 μM terbium were incubated with 0.1 and 1 mM calcium, 10 mM magnesium, or 100 μM lanthanum in 10 mM Tris, 1 mM DTT, 1% glycerol, pH 7.4; and the terbium fluorescence of each sample was measured.

Calcium Binding Dye Competition.

The protein (30 or 40 μM) and Rhodamine-5N (~20 μM, Molecular Probes) (The Journal of Biological Chemistry, 264, 19449-19457) were incubated in 10 mM Tris, 1 mM DTT, 1% glycerol, pH 7.4. A 100 mM $CaCl_2$ stock containing the same concentrations of dye. Protein was gradually added into the mixture, and the fluorescence was measured with a 1 cm pathlength cell and an excitation of 552 nm. After the titration, the dye concentration was verified by absorbance at 552 nm with an extinction coefficient of 63,000 $cm^{-1}$. The data were analyzed by globally fitting the spectra from 560 to 650 nm using Specfit/32 with the metal-ligand-ligand model (Talanta, 33, 943).

Mammalian Cell Transfection.

Untransfected HeLa cells (a generous gift from Dr. Klaus Willecke of the University of Bonn, Germany) were maintained on 100 mm tissue culture dishes in filter-sterilized Dubelcco's Modified Eagle's Medium (DMEM, Sigma Chemical Co.) with 44 mM $NaHCO_3$, pH 7.2, and were supplemented with 10% v/v Fetal Calf Serum (FCS, Hyclone), 100 U/ml penicillin and 0.1 mg/ml streptomycin (Pen/Strep, Sigma) at 37° C. with 5% $CO_2$ in a humidified incubation chamber. The designed protein DNA was subcloned into pcDNA3.1+ vector (Invitrogen) for expression in mammalian cells through EcoRI and BamHI digestion, followed by ligation with T4 DNA Ligase. The DNA, confirmed by automated sequencing, was transfected into previously prepared 90% confluent HeLa (HEK293, Vero, or CHO) cells using Lipofectamine-2000 (Invitrogen) on 60 mm cell-culture-treated dishes. The DNA (3 μg) was mixed with Lipofectamine-2000 in a 1:3 ratio in Opti-MEMI serum-free medium (Invitrogen) and was allowed to equilibrate at room temperature for 20 min in the dark before being added to the cells in Opti-MEMI medium. The transfection was allowed to proceed for 4 hrs at 37° C. and 5% $CO_2$. The transfection medium was removed and was replaced with DMEM, 10% FCS, 1% Penicillin-Streptomycin Solution; and the cells were grown at 30° C. at 5% $CO_2$ for 72 hrs. Mock-transfected HeLa cells were treated in the same way without DNA addition for a background control.

Microscopy Imaging.

HeLa cells transfected with GFP.Ca1 were imaged 72 hrs following transfection. Coverslips with cells were transferred to a microincubation chamber (model MSC-TD, Harvard Apparatus, Holliston, Mass.). Briefly, imaging of GFP.Ca1 fluorescence was performed on a Nikon TE300 (Nikon Inc., Melville, N.Y.) inverted microscope equipped with a Nikon filter block optimized for GFP optics ($\lambda_{ex480}$, $\lambda_{em\,510}$; Chroma Technology Corp, Rockingham, Vt.), a Metaltek filter wheel (Metaltek Instruments, Raleigh, N.C.) to regulate excitation light exposure times, a 75 watt xenon short arc lamp, a Hamamatsu CCD digital camera (Hamamatsu Corporation, Bridgewater, N.J.), and supported on a vibration isolation table (Technical Manufacturing, Peabody, Mass.). MetaFluor software (Universal Imaging Corp., v 3.5, Downington, Pa.) was utilized for image acquisition. Acquisition time was 50 ms with a gain of 1-3, depending upon the transfection efficiency.

The fluorescence intensity of the transiently transfected GFP.Ca1 or GFP.Ca1c3 was monitored for several minutes to obtain a baseline value before the addition of ionomycin to the bath buffer to a final concentration of 2 µM. The designed protein's fluorescence was imaged until the fluorescence intensity was stable (typically 2 min), and the intracellular calcium concentration was then manipulated by the subsequent addition of concentrated $CaCl_2$ to obtain the targeted extracellular calcium concentration. Multiple additions of $CaCl_2$ were typically spaced 1 min apart. Extracellular calcium concentrations were returned to basal levels by bath perfusion of $HBSS^{++}$ buffer. EGFP without a calcium binding site was utilized as a control.

To test the calcium response of the sensor expressed in the ER, 50-100 µM ATP and 100 µM histamine were added to the bathing medium to induce calcium release from the ER. Higher concentrations of ionomycin (2.5-5 µM) were utilized to permeabilize the ER membrane and to allow for calcium uptake with addition of calcium to the bathing medium (10-100 mM). Thapsigargin (1 µM) and calmidozolium (2 µM) were added to the bathing medium to empty slowly the ER of calcium.

Results
Design of Calcium-Binding GFP.

The design of calcium binding proteins in green fluorescent protein was carried out using the established design program and the given parameters based on the pentagonal bipyramidal geometry (Biochemistry, 44, 8267-73; J Am Chem Soc. 127, 2085-2093; J Am Chem Soc. 125, 6165-6171). More than 3000 potential calcium binding sites were computationally constructed. Several criteria were applied to rank and to choose sites. First, any sites that contained mutations in the central helix (i.e. amino acids 56 to 71) were removed. Second, sites that replaced buried hydrophobic residues with charged residues were removed to avoid folding disruptions. Third, sites involving solvent-inaccessible residues, such as Phe8, were eliminated since solvent accessibility is observed for many calcium binding sites. The solvent accessibility was evaluated with the program GetArea. Fourth, the mutations in the loop regions with higher flexibility were considered "safe" without disrupting the protein folding, while sites involving the mutations on the β-strands were considered more aggressive. Fifth, since fewer mutations are less likely to perturb the native protein conformation, predicted sites with more existing residues as ligands are preferred. Sixth, the distance from the chromophore was also evaluated for the potential development of calcium sensors. The over packing of protein was examined, and the clash with close residues was avoided. In addition, the sites with three to four negatively charged ligand residues were preferred based on the statistical results for calcium binding proteins. Finally, to have a potential calcium-induced fluorescence change, chromophore sensitive locations were analyzed based on the dynamic and conformational properties of the fluorescent proteins (*J Mot Behav.* 39, 341-351).

Figure 15:
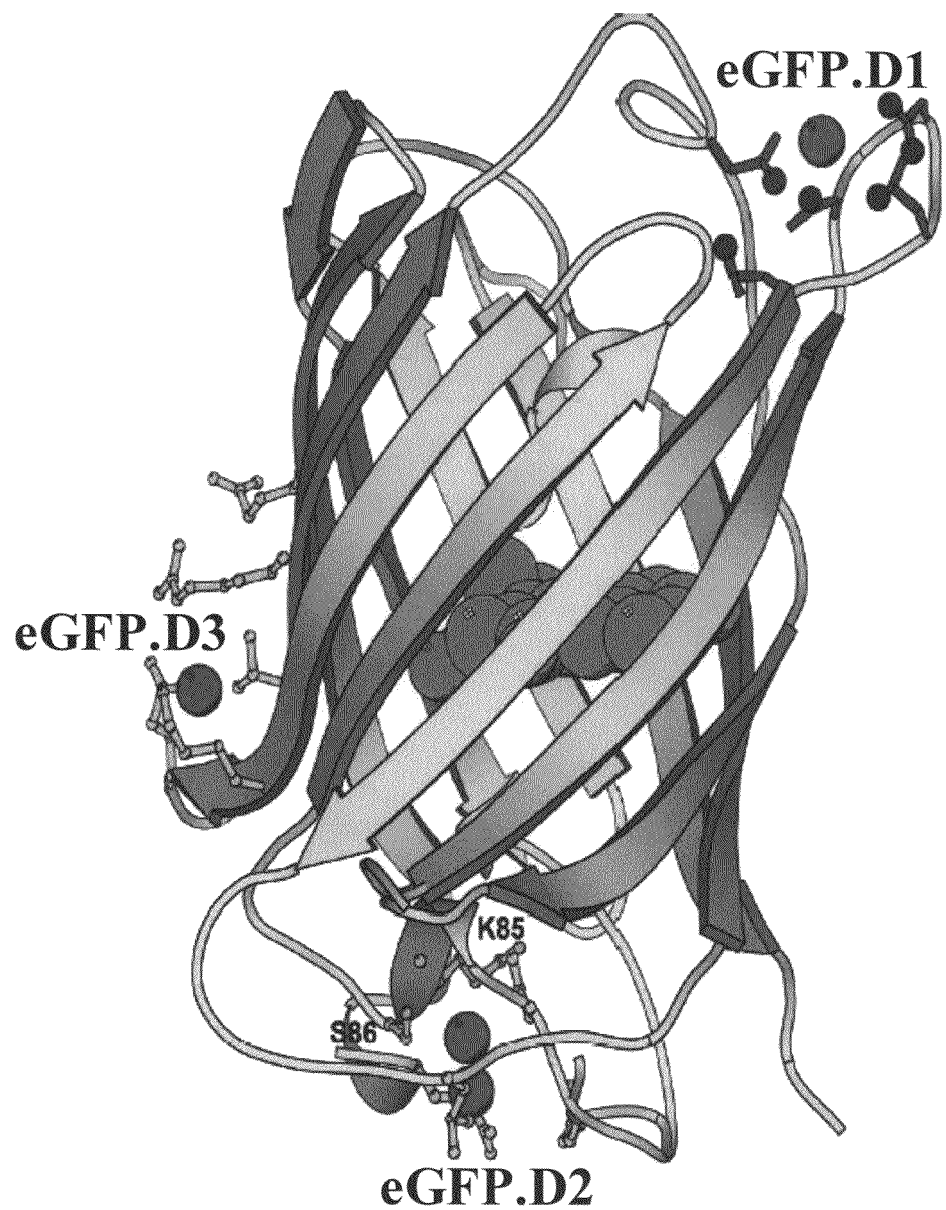
FIG. 15 illustrates the designed calcium-binding proteins based on GFP (pdb 1b9c). The proposed binding geometry of GFP.D1 is shown in ball-and-stick with the calcium highlighted in red. D2 is shown as a circle. The locations of GFP.D3 with the wild type residues are also shown in the same figure although they were incorporated separately.

FIG. 15 shows five calcium binding sites (termed GFP.D1, GFP.D2, GFP.D2', GFP.D2", and GFP.D3) located in three different positions in GFP chosen based on the criteria (Table 1 in FIG. 19). GFP.D1 is located at the end of the barrel in the loop regions. It is expected to have less effect on the EGFP folding and structure due to the flexibility of the loop region. GFP.D2, GFP.D2', and GFP.D2" are located in the loop region on the opposite end of the barrel from GFP.D1. They contain four identical ligand residues and differ by one residue. GFP.D2 has ligands L194E, S86D, S2D, D82, and E5. L194 was mutated to be N in both GFP.D2' and GFP.D2". GFP.D2' contains K85D mutation whereas GFP.D2 and GFP.D2" contains S86D. This alters the sidechain packing and electrostatic interactions in the local environment due to the different size and charge natures of Lys, Glu, Asn, and Ser. GFP.D3 is located in the middle of the barrel, 14 Å to the chromophore. All ligand residues, including two natural ones and three mutations, are located on the β-strands.

Chromophore and Conformational Properties of Designed Proteins.

Figure 16:
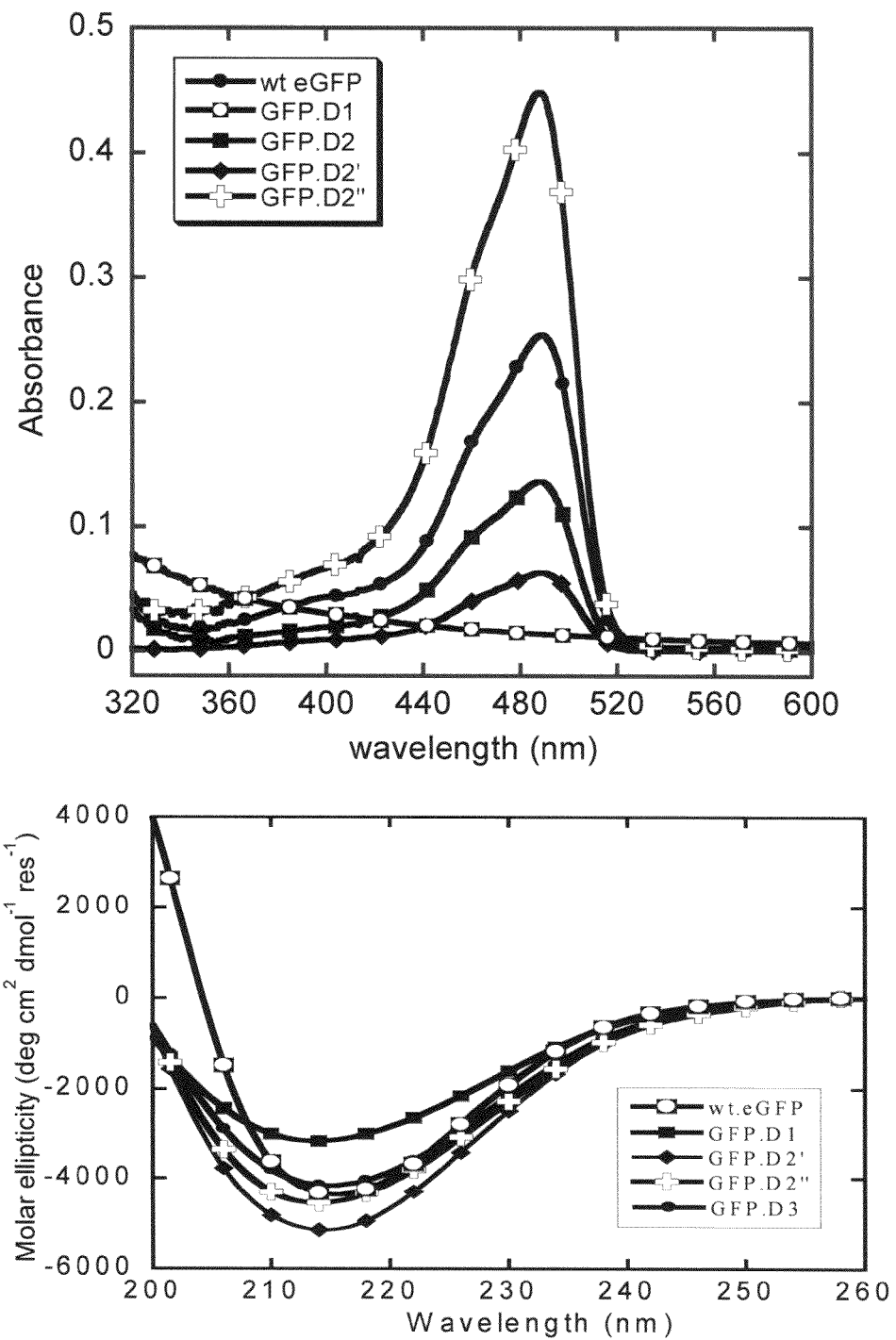
FIG. 16a illustrates the absorbance spectra of EGFP and GFP.D1, GFP.D2, GFP.D2' and GFP.D2"expressed in *E. coli*, which indicate that the chromophore of GFP.D1 did not form.
FIG. 16b Far UV CD spectra of GFP.D1, GFP.D2', GFP.D2", and GFP.D3 in 10 mM Tris, 1 mM DTT, 1% glycerol, pH 7.4 indicate the formation of β-sheet secondary structures with a negative maximum at 216 nm.

These four calcium binding sites were engineered into EGFP, and they exhibit different optical properties. First, among all of the bacterial-expressed proteins in *E. coli*, GFP.D2 is the only one that retains green fluorescence color. As shown in FIG. 16, the bacterial-expressed and purified GFP.D2 and its series and w.t EGFP exhibit absorption maxima at 490 nm. The excitation at 490 nm results in an emission maximum at 510 nm. In contrast, the rest of the bacterial-expressed proteins GFP.D1 and GFP.D3 (data not shown) are colorless, indicating no chromophore formation in the bacterial-expression system. FIG. 16b shows that the far UV CD spectra of these designed proteins have a negative maximum at 216 nm similar to EGFP, indicating that a dominant β-sheet structure was not altered after introducing calcium binding ligand residues although the chromophore formation was perturbed.

Figure 17:
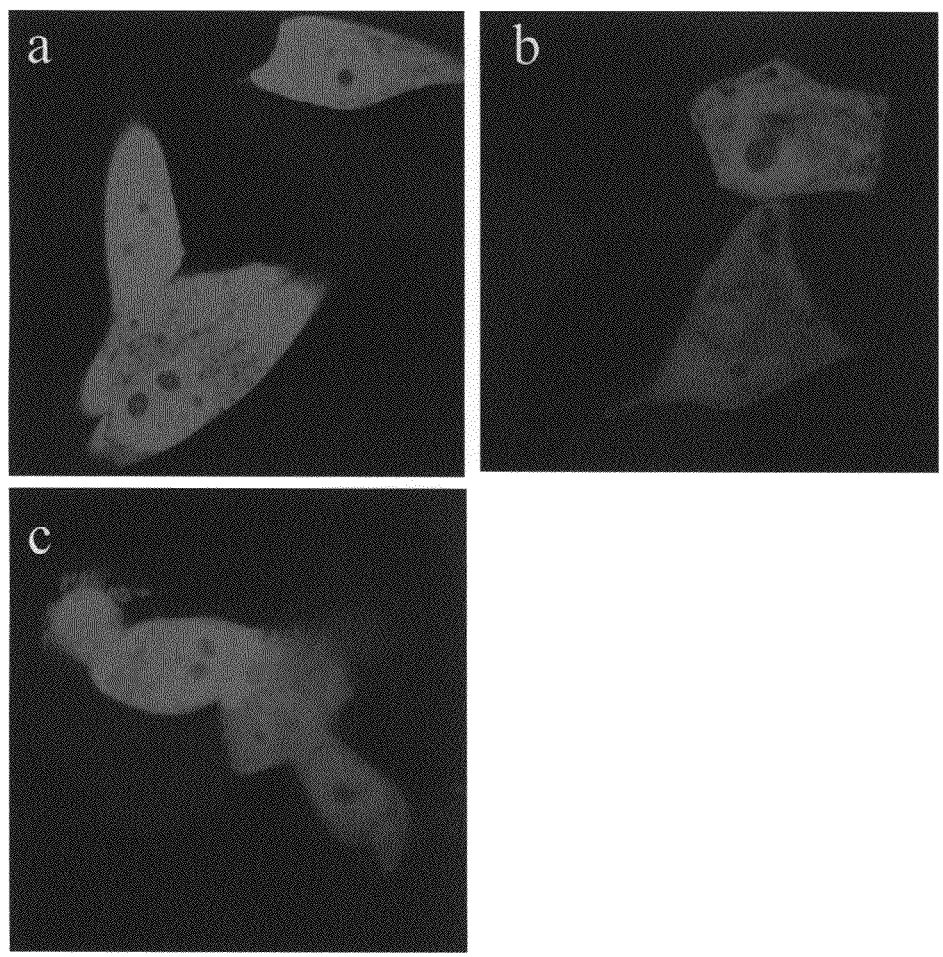
FIG. 17 illustrates the inverted epifluorescence image of HeLa cells expressing wt.eGFP (FIG. 17a), GFP.D1 (FIG. 17b) and GFP.D2 (FIG. 17c).

Since GFP is originally from jellyfish and it was reported that a eukaryotic expression system is able to facilitate chromophore formation since eukaryote cells contain much more machinery to aid in protein folding (J Mol Biol, 353, 397-409). FIG. 17 shows that both GFP.D1 and GFP.D2 exhibit fluorescence when expressed in Hela cell. In contrast, GFP.D3 remains colorless when expressed in the mammalian cells similar to its expression in bacterial system (data not shown). These results suggest that introducing several charged residues for calcium binding does not affect the folding and structure of the protein but does affect the synthesis and formation of the chromophore, which has less tolerance for environmental modifications.

Metal Binding Affinities and Selectivity of Designed GFP Variants.

Figure 18:
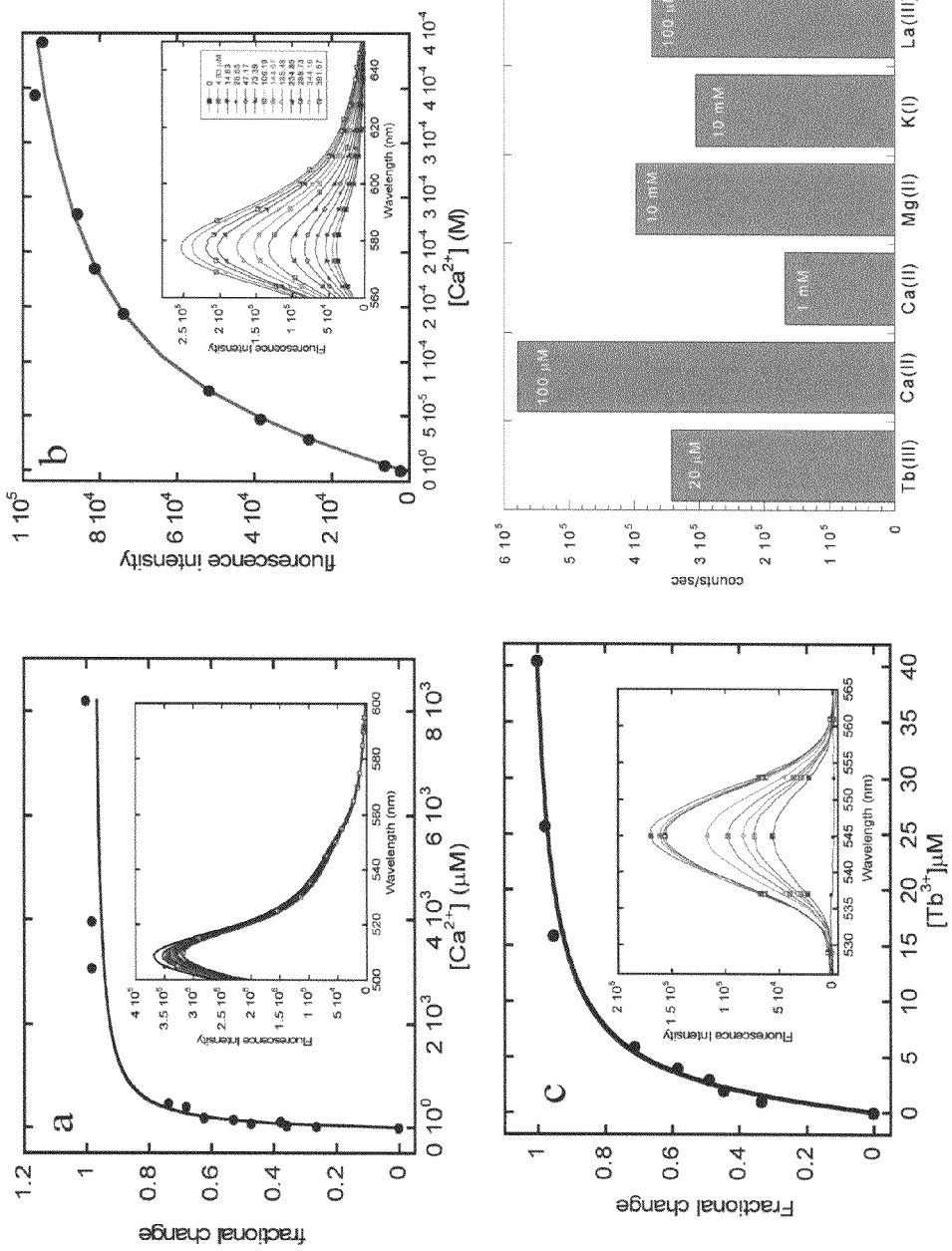
FIG. 18a illustrates the calcium induced chromophore emission change for GFP.D2 expressed in *E. coli* with excitation at 482 nm in 10 mM Tris, 1 mM DTT, 1% glycerol, pH 7.4. The fit of the data with the 1:1 binding equation (Eq 2.3) produces a $K_d$ of 107 μM.
FIG. 18b illustrates the rhodamine-5N competition with GFP.D2 for calcium binding fluorescence emission with excitation at 552 nm. The experiment was performed in 10 mM Tris, 1 mM DTT, 20% glycerol, pH 7.4. The inset shows the spectra of the Rhodamine-5N with the concentration change of $Ca^{2+}$.
FIG. 18c illustrates the fluorescence spectra of 3 μM GFP.D1 in 20 mM PIPES, 10 mM KCl, 1 mM DTT, 1% glycerol, pH 6.8 with increasing terbium concentration (bottom to top). The inset shows that the spectra increases at 545 nm, in which the line is generated assuming a 1:1 binding.
FIG. 18d illustrates the metal competition of GFP.D1.

Metal binding capability for calcium and its analog lanthanide ions of designed GFP variants were examined using four different methods using bacterial expressed and purified proteins. For GFP.D2 with a correct formed chromophore, metal binding affinity was directly determined by monitoring fluorescence signal change as a function of metal concentration. As shown in FIG. 18a, the addition of calcium from 0 to 10 mM results in a gradually decrease of fluorescent signal at 510 nm when excited at 398 nm. The fractional change at 510 nm can be well fitted with the equation forming 1:1 calcium:protein complex. The dissociate constants for calcium is 107±13. On the other hand, wt. EGFP does not have any significantly fluorescence signal change upon addition of the metal ions (data not shown).

We then used Rhodamine-5N (Molecular Probes), a commercially available calcium binding dye to obtain calcium and lanthanide affinity by a dye competition assay. As shown in FIG. 18b, Rodmine-5N shows a large fluorescence signal increase when calcium is bound in GFP.D1. In the dye competition assay, the solutions with constant dye and protein concentration were titrated with calcium until saturation was observed (FIG. 18b insertion). The binding affinities for the designed proteins were obtained by globally fitting the spectra with the metal-and-two-ligand model. As shown in Table 1 in FIG. 19, the calcium binding affinities of GFP.D2 obtained by directly measurement of fluorescence signal change are in a good agreement with that obtained by dye the competition method. Calcium binding dye competition was then used to obtain calcium binding affinities for these bacteria expressed proteins GFP.D1, GFP.D2, GFP.D2' and GFP.D2" and GFP.D3. Their calcium-binding affinities are 60±5, 57±2, 96±7 and 38±5 μM, respectively.

To further characterize the metal binding of the designed proteins, terbium sensitized fluorescence resonance energy transfer was used. Terbium, a calcium analog with similar ionic size and binding geometry, is intrinsically fluorescent at 545 nm and able to accept energy transferred from aromatic residues. EGFP contains 1 Trp and 10 Tyr, and the Trp is within 30 Å of GFP.D1 and GFP.D2 and 17 Å of GFP.D3 and GFP.D4 (Table 1 in FIG. 19). As shown in FIG. 18c, the addition of terbium into the protein results in a large increase in terbium-FRET signal at 545 nm with excitation at 280 nm. The enhancement as a function of terbium concentration with the assumption of a 1:1 metal:protein complex provided the binding affinities (Table 1 in FIG. 19). Of the three proteins tested at pH 7.4, GFP.D1 has the strongest terbium affinity (1.9±0.4 μM). GFP.D2 has a slightly weaker affinity of 4.9±0.2 μM while GFP.Ca2' exhibits a 15 fold weaker affinity of 32±13 μM. At pH 6.8, GFP.D2" exhibits a binding affinity for terbium of 2.9±0.3 μM. The addition of calcium and lanthanum into the terbium-protein complex significantly reduced the fluorescence enhancement of terbium due to competition. As shown in FIG. 18d, addition of 1 mM calcium resulted in a large decrease in terbium fluorescence for GFP.D1, suggesting that calcium binds to the protein and competes for terbium binding. Addition of 100 μM lanthanum resulted in a fluorescence decrease to half, suggesting an estimated 5-fold lower metal binding affinity (~10 μM). On the other hand, addition of higher concentrations of magnesium (10 mM) resulted in a relatively smaller decrease, indicating a relatively weaker binding affinity. Similarly, GFP.D2' exhibits a half maximal decrease in fluorescence with 1 mM calcium or 100 μl lanthanum, which is also more effective than magnesium. Taken together, calcium and lanthanides bind to the protein in the same pocket and have a >20 fold selectivity over magnesium. As shown in Table 1, FIG. 19, the designed calcium binding sites have calcium binding affinities with $K_d$ in the range of 38-96 μM. The metal selectivity is also sufficient for the proteins to bind calcium without interference from magnesium in the extracellular environment or in the ER where calcium concentration is much higher than in the cytosol.

Example 4

Introduction

Toxic metals (e.g.—$Gd^{3+}$, $La^{3+}$, $Tb^{3+}$, $Pb^{2+}$, $Sm^{3+}$, $Sr^{2+}$, $Hg^{2+}$ and $Cd^{2+}$) are not beneficial, but may interact adversely, with biological systems. While the toxicological effects of metal poisoning have been extensively studied, the mechanisms of toxicity relative to interaction with proteins are not fully-understood. Lead ($Pb^{2+}$) is a persistent, anthropogenic toxic metal responsible for a variety of health problems related to neurological disorders, anemia, kidney damage, hypertension and male fertility decrease (Reprod Toxicol, 2005. 20(2): p. 221-8; Am J Ind Med, 2000. 38(3): p. 310-5; Neurotoxicol Teratol, 2005. 27(2): p. 245-57; Annu Rev Nutr, 1997. 17: p. 37-50; Int J Toxicol, 2001. 20(3): p. 113-20; Int J Dev Neurosci, 2000. 18(8): p. 791-5; Ann N Y Acad Sci, 1987. 514: p. 191-203). Lanthanides are known to block calcium channels in human and animal cells, and $Pb^{2+}$, $Cd^{2+}$, and $Hg^{2+}$ will specifically target voltage-gated calcium channels (J Bioenerg Biomembr, 2003. 35(6): p. 507-32). The deleterious impact of metals on human health may be extensive in both scope and duration, as seen with the groundwater arsenic problem in Bangladesh where it is estimated that 41 million people are at risk for exposure (Environmental health perspectives, 2000. 108(5): p. 393; Elements, 2006. 2(2): p. 71-75.) There is, therefore, a strong need to develop inexpensive, benign materials for the detection and neutralization of toxic metals in natural systems, and for biological remediation.

In the present example, we investigate the application of engineered variants of EGFP as analyte sensors with high affinity and selectivity for $Pb^{2+}$ and $Gd^{3+}$ ions. The autofluorescence of GFP and its variants make it a versatile tag for metal-binding studies where the close proximity of a metal cation to a chromophore in the protein results in a detectable quenching of the fluorescent peaks Biochem Biophys Res Commun, 2000. 268(2): p. 462-5.)

Materials and Methods

Development of EGFP-Based $Pb^{2+}$ and $Ln^{3+}$ Sensors

The EGFP protein variants designed for metal-binding and protease studies were developed via sub-cloning through polymerase chain reaction (PCR). Proteins were prepared for subsequent purification on a $Ni^{2+}$ chelating sepharose column by addition of a 6×His-tag. These variants provide the scaffold for mutagenesis studies aimed towards designing proteins with high metal selectivity, and for development of a protease sensor. EMD Omnipur tris (hydroxymethyl)aminoethane (EMD Chemicals, Inc., Gibbstown, N.J.), or TRIS, was utilized extensively as a buffering agent to maintain pH for the expressed proteins. Luria-Bertani media were prepared in a 2.8 L Erlenmeyer flask by combining 10 g Bacto-Tryptone (Becton, Dickinson and Co., Sparks, Md.) with 5 g Bactone-yeast extract (EMD Chemicals, Inc., Gibbstown, N.J.), 10 g NaCl, and then filling the flask to 1 L with $ddH_2O$. The pH was adjusted to 7.0 with 5 M NaOH (J. T. Baker, Phillipsburg, N.J.).

Transformation

The pET28a vector used for coding EGFP variants was transformed into *Escherichia coli* cell strain DE3, and grown on Agarose plates. During preparation, 50 μL of the appropriate cell strain were added to an autoclaved microcuvette, followed by 0.5 μL of DNA. Samples were incubated on ice for 30 min. Subsequent to incubation, the sample was subjected to heat shock for 90 s at 42° C. to allow DNA into the cell. The sample was placed on ice for 2 minutes. After cooling the sample, 50 μL of LB Medium were added, and the sample was placed in an incubator for 30 minutes at 37° C. Culture plates were labeled and dated. Steel coils were heated in an open flame and immersed in EtOH several times for sterilization. The cell culture was then added in drops onto the agarose plate, and spread across the surface with the sterilized coil. The plate was then covered and placed in an incubator overnight at 37° C.

Inoculation 20 mL of LB medium, pH 7.0, were transferred by pipette into a 50 mL disposable centrifuge tube, followed by 12 μL of 50 mg/mL kanamycin, for a final concentration of 0.03 mg/mL kanamycin. A cell colony was scraped from the agarose plate using an inoculation loop, and transferred to the LB media in the centrifuge tube. The sealed tube was then placed in a large beaker and packed with paper towels to prevent movement of the tube. The beaker was then placed in an incubator-shaker overnight at 37° C.

Expression

In 1 L of autoclaved LB medium, 600 μL of 50 mg/mL kanamycin was added for a final concentration of 0.03 mg/mL. Optical density of the cell cultures was monitored using a Shimadzu UV-1601 PharmaSpec UV-Vis spectrophotometer with UV Probe software (Shimadzu North America, Columbia, Md.).

Samples for the spectrophotometer were prepared in 1.0 mL plastic, disposable cuvettes. Two reference cuvettes were prepared for the baseline using 1.0 mL of the LB medium/kanamycin. Using the Bunsen burner, the neck of the 2.8 L Erlenmeyer flask was rotated in the flame to prevent bacterial growth. Next, the cell culture in the 50 mL disposable centrifuge tube was poured into the 2.8 L flask. The flask was covered with Aluminum foil, and secured in the incubator-shaker set at 200 rpm, 37° C. The optical density of the sample was checked in the UV-Vis spectrophotometer until the absorbance reached 0.6±0.1, at 600 nm. This range was previously determined for optimal induction. At the appropriate absorbance, 200 μL of Isopropyl-beta-D-thiogalactopyranoside (IPTG) were added to induce expression of the protein, for a final IPTG concentration of 0.2 mM, and the temperature reduced to 20-25° C., for optimal expression. Following induction, 1.0 mL samples were removed every hour for three hours, followed by a final sample on the following day, to evaluate protein expression using SDS-PAGE gels. Cell pellets were harvested the following day by centrifugation, and stored in a freezer at 4° C. until they could be purified.

Purification

To the collected cell pellet, ~20 mL of extraction buffer (20 mM TRIS, 100 mM NaCl, 0.1% Triton x-100) was added, and the sample vortexed to dissolve. The dissolved cell pellet was poured into a 50 mL plastic beaker, and the beaker placed on ice. The sample was then sonicated six times to break the cell membranes, for 30 s periods, with ~5 min intervals between sonications. Following sonication, the cell pellet solution was centrifuged for 20 min at 53, 442×g to separate the protein into the supernatant. The extracted supernatant was filtered with 0.45 μm pore size filter (Whatman, Florham Park, N.J.) into a 50 mL plastic centrifuge tube. Concentrated solutions were diluted with the appropriate binding buffer prior to injection into the FPLC system.

Purification of EGFP variants was completed using an Aktaprime FPLC (Amersham Biosciences, Piscataway, N.J.) equipped with a UV detector and a 280 nm optical filter. Preparation of the FPLC required rinsing of both pumps A and B with 10 mL ddH$_2$O, twice each.

Two different columns were utilized. For most purifications, a Hitrap 5 mL HP Chelating sepharose column was used. The binding Buffer A was comprised of 1 M K$_2$HPO$_4$, 1 M KH$_2$PO$_4$, 250 mM NaCl, pH 7.4. The elution Buffer B was comprised of Buffer A and 0.5 M imidazole.

The column was first rinsed with EDTA (Acros Organics, Geel, Belgium) solution (100 mM EDTA, 1 M NaCl, pH 8.0) to remove any metals, followed by ddH$_2$O. Following the EDTA rinsing step, the column was washed with 0.1 M NiSO$_4$, to bind Ni$^{2+}$ onto the column, and rinsed again with ddH$_2$O to remove any unbound NiSO$_4$.

For additional purification, a Hitrap Q Ion Exchange column (GE Healthcare, Piscataway, N.J.) was used. For the Q column, the binding Buffer A was comprised of 20 mM TRIS, pH 8.0. The elution Buffer B was comprised of 20 mM TRIS, 1 M NaCl, and pH 8.0.

Protein injections onto the column were limited to 5-8 mL. Once all of the protein was loaded onto the column, an elution method was run to elute the bound protein in 8 mL fractions. The collected fractions were further purified by dialysis in 2.0 L of 10 mM TRIS, 1 mM Dithiothreitol (DTT), (Inalco, Milano, Italy), pH 7.4. Protein fractions were sealed in dialysis bags (Spectrum, Rancho Dominguez, Calif.) with a molecular weigh cutoff value of 3,500 Da, and stirred on a stir plate for 72 hours. The dialysis solution was changed every 24 hours to remove imidazole and other impurities. Following dialysis, samples were extracted from the collected fractions and the purity evaluated using SDS-PAGE gels.

Spectroscopic Analysis

Protein concentration was determined using UV-Vis Spectrometry, based on the Beer-Lambert Law $$A = \epsilon bc \qquad \text{Eq. (1)}$$

where b=path length (1 cm), A is the measured absorbance, and $\epsilon$ is the previously determined molar absorptivity found experimentally to be 21890 M$^{-1}$ cm$^{-1}$. The absorbance scan encompassed the range of 600-220 nm, and the absorbance for determining concentration was measured at 280 nm.

Fluorometric spectral analyses of EGFP variants were conducted using two different PTI (Photon Technology International, Birmingham, N.J.)

Spectrofluorometers equipped with a 75 W xenon arc lamp and a model 814 Photomultiplier Tube (PMT) detector. During analyses, the excitation slit widths were set at 1 nm, to reduce potential photobleaching of the proteins, and the emission slit widths were set at 2 nm. Excitation wavelengths of 398 nm and 490 nm were used. Data from the fluorometers were collected at 1 nm intervals, and stored on PC's running Felix32 software (Photon Technology International, Lawrenceville, N.J.). Additional verification of excitation spectra was obtained using a Shimadzu spectrofluorometer (Shimadzu North America, Columbia, Md.).

The selectivity of the EGFP-based sensors for Pb$^{2+}$ and Gd$^{3+}$ was examined by monitoring the change of the fluorescence ratio $F_{(398\ nm)}/F_{(490\ nm)}$ with 1.0 mM Ca$^{2+}$ in the presence of metal ions.

The Ratiometric change from the metal-free protein to the metal-protein complex was calculated by integrating the peak areas for each of the emissions scans (398 nm and 488 nm) from 500-600 nm as a sum of the intensities recorded at each 1 nm interval, and then evaluating the ratio of (F398/F488), as seen in Eq. 2.

$$\text{Ratiometric change} = (F398/F488) = \left( \frac{\sum_{500}^{600} \text{Counts}398}{\sum_{500}^{600} \text{Counts}488} \right) \qquad \text{(Eq. 2)}$$

This change is calculated as a ratio to eliminate potential errors associated with absolute intensity values that might arise due to instrumental variations.

The fluorescent ratiometric change (F398/F490) was evaluated for 1.0 μM the EGFP variants to evaluate selectivity between Ca$^{2+}$ and Pb$^{2+}$ or Gd$^{3+}$ in 10 mM TRIS-Cl, pH 7.4. First, 1 mM Ca$^{24}$ was added to the protein, followed by aliquots of the competing metal.

The affinity of a competing ion is assumed to be directly proportional to the change in the ratio (F398/F490), as calculated using Equation 11. To calculate K$_{eq}$ for the competitive titration, the value for the fraction of the competing ion (F) must be first normalized across the range of concentrations evaluated. This F Normalized value (F$_{Norm}$) was calculated with Eq. 3.

$$F_{Norm} = (F_{Ca\ initial} - F_{M+})/(F_{Ca\ initial} - F_{M+final}) \qquad \text{(Eq. 3)}$$

In Equation 3, $F_{ca\ initial}$ represents the initial ratio (F398/F490) following addition of $Ca^{2+}$, $F_{M+}$ is the ratio at each point for addition of competing metal ion, and $F_{M+final}$ is the ratio at the final concentration of metal. Once $F_{Norm}$, was calculated, K for the competitive titration was calculated in Kaleidagraph with the following curve-fitting equation:

$$F_{Norm}=((([P]_t+[M]_t+K)-((([P]_t+[M]_t+K)^2-4[P]_t[M]_t)^{1/2})/2[P]_t)+(C*[M]_t) \quad \text{(Eq. 4)}$$

where the final term, $(C^*[M]_t)$, accounts for non-specific binding. $K_d$ for $Pb^{2+}$ or $Gd^{3+}$ was then calculated using Equation 4, with K calculated from Equation 3, and $K_d$ for $Ca^{2+}$ which was previously determined in our laboratory for the EGFP-C2 variant to be 440 µM.

$$K_{dM+}=K/(1+([Ca^{2+}]/K_{dCa})) \quad \text{(Eq. 4)}$$

Absorbance data for the proteins were obtained using a Shimadzu UV-1700 PharmaSpec spectrophotometer with UVProbe software. The absorbance scan encompassed the range of 600-220 nm. Data from all spectra were saved in text files for subsequent processing in spreadsheet software, either Microsoft Excel (Microsoft, Redmond, Wash.) or Kaleidagraph (Synergy Software, Reading, Pa.).

Results

Figure 21:
FIG. 21 illustrates competitive titration of $Pb^{2+}$ with $Ca^{2+}$-loaded EGFP variants C2 and C-4.
Figure 22:
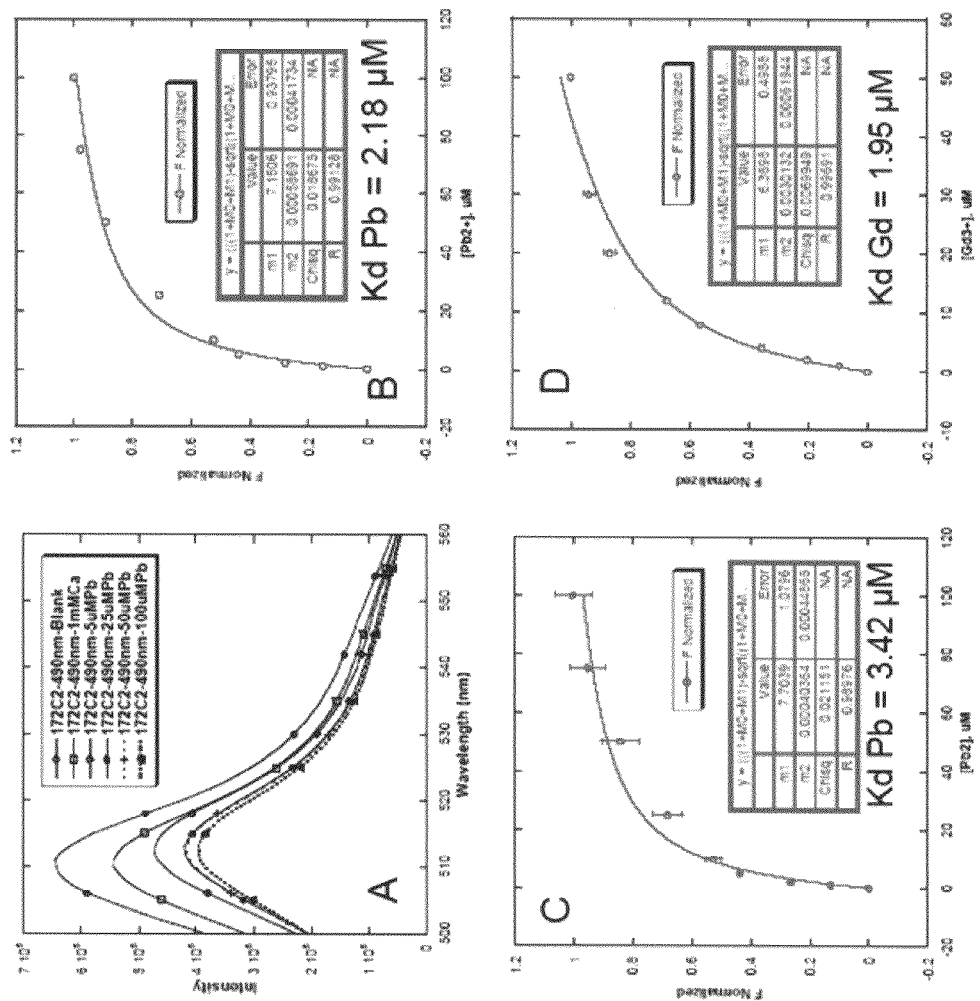
FIG. 22A illustrates titration of excess $Pb^{2+}$ with $Ca^{2+}$-loaded EGFP variant C2. Signal intensity decreases as Pb displaces Ca.
FIG. 22B illustrates the curve-fitting of C2-Pb complex to quantify Kd. The Kd for C2-$Pb^{2+}$ was 2 μM, and $Ca^{2+}$ was 440 μM.
FIG. 22C illustrates curvefitting of EGFP (SEQ ID NOs. 18 and 19)/$Pb^{2+}$ complex to quantify Kd. The Kd was 3.5 μM.

It was determined from competitive titrations that $Gd^{3+}$ and $Pb^{2+}$ will displace $Ca^{2+}$ in the binding sites of our engineered EGFP variants. FIG. 21 shows the normalized ratiometric changes associated with displacement of $Ca^{2+}$ by $Pb^{2+}$. FIG. 22 shows changes in fluorescence intensity resulting from displacement of $Ca^{2+}$ by $Pb^{2+}$, and a 2-3 nm red shift in the spectra near 10 µM $Pb^{2+}$. This red shift is believed to be the result of conformational changes relative to the chromophore, unrelated to displacement of $Ca^{2+}$ which has already occurred. These data were then used to calculate binding affinities for both $Gd^{3+}$ and $Pb^{2+}$. For the EGFP-C2 variant analyzed in this work, the binding affinities for $Pb^{2+}$ and $Gd^{3+}$ were both found to be ~200 times higher than $Ca^{2+}$ (FIG. 22B, FIG. 22D). For the other EGFP variant (SEQ ID Nos.18 and 19), the binding affinity for $Pb^{2+}$ was found to be over 100 times higher than $Ca^{2+}$. (FIG. 22C) These higher affinities, coupled with the conformational changes associated with the binding of these metals, suggests an important relationship to toxicity. It also provides for a natural sensor capable of high-affinity binding for $Pb^{2+}$ and $Gd^{3+}$.

We claim the following:

1. An analyte sensor comprising:
   a) a molecular recognition motif that binds an analyte; and
   b) an optically-active fluorescent host protein in which the molecular recognition motif is operatively linked to or integrated therein, and
   wherein the interaction of the analyte to the molecular recognition motif produces a detectable change, wherein the optically-active fluorescent host protein is an enhanced green fluorescent protein (EGFP), wherein EGFP includes a mutation selected from: M153T/V163A or F99S/M153T/V163A.

2. The analyte sensor of claim 1, wherein the analyte sensor is stable at temperatures of about 30 to 37° C.

3. The analyte sensor of claim 1, wherein the analyte sensor is stable at temperatures of about 37° C.

4. The analyte sensor of claim 1, wherein the molecular recognition motif includes an analyte binding site.

5. The analyte sensor of claim 1, wherein the molecular recognition motif includes an analyte binding site and a structural motif, wherein the structural motif is selected from a primary structure motif, a secondary structure motif, a tertiary structure motif, quaternary structure motif, a fragment or domain.

6. The analyte sensor of claim 5, wherein the structural motif is selected from EF-hand motifs and alpha lactalbumin calcium binding motifs.

7. The analyte sensor of claim 5, wherein the structural motif is selected from: a loop, a loop-helix, a helix-loop, a helix-loop-helix motif, a beta-loop-helix, and a beta-loop-beta.

8. The analyte sensor of claim 7, wherein the helix-loop-helix motif is an EF-hand motif.

9. The analyte sensor of claim 1, wherein the molecular recognition motif is located in a region sensitive to the chromophore environment and has solvent accessibility.

10. The analyte sensor of claim 9, wherein the sensitive region is disposed in the loop between amino acids selected from 170, 172, or 157, and combinations thereof, of enhanced green fluorescent protein (EGFP).

11. The analyte sensor of claim 1, wherein detectable change corresponds to conformational change that produces an alteration of the chromophore microenvironment under the inducement of the analyte.

* * * * *

UNITED STATES PATENT AND TRADEMARK OFFICE
CERTIFICATE OF CORRECTION

PATENT NO. : 8,420,327 B2  Page 1 of 1
APPLICATION NO. : 12/448101
DATED : April 16, 2013
INVENTOR(S) : Ellis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 772 days.

Signed and Sealed this
First Day of September, 2015

Michelle K. Lee
*Director of the United States Patent and Trademark Office*

SEQUENCE LISTING

```
<160> NUMBER OF SEQ ID NOS: 102

<210> SEQ ID NO 1
<211> LENGTH: 251
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 1

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Lys Asp
                165                 170                 175

Gly Asn Gly Tyr Ile Ser Ala Ala Glu Asp Gly Ser Val Gln Leu Ala
            180                 185                 190

Asp His Tyr Gln Gln Asn Thr Pro Ile Gly Asp Gly Pro Val Leu Leu
```

-continued

Pro Asp Asn His Tyr Leu Ser Thr Gln Ser Ala Leu Ser Lys Asp Pro
    210                 215                 220

Asn Glu Lys Arg Asp His Ile Val Leu Glu Phe Val Thr Ala Ala
225                 230                 235                 240

Gly Ile Thr Leu Gly Met Asp Glu Leu Tyr Lys
                245                 250

<210> SEQ ID NO 2
<211> LENGTH: 262
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 2

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Asp Gly Ser Val Gln Leu Ala Asp His Tyr Gln Gln
        195                 200                 205

Asn Thr Pro Ile Gly Asp Gly Pro Val Leu Leu Pro Asp Asn His Tyr
    210                 215                 220

Leu Ser Thr Gln Ser Ala Leu Ser Lys Asp Pro Asn Glu Lys Arg Asp
225                 230                 235                 240

His Ile Val Leu Leu Glu Phe Val Thr Ala Ala Gly Ile Thr Leu Gly
                245                 250                 255

Met Asp Glu Leu Tyr Lys
            260

<210> SEQ ID NO 3
<211> LENGTH: 259
<212> TYPE: PRT
<213> ORGANISM: artificial sequence
<220> FEATURE:
<223> OTHER INFORMATION: Description of Artificial Sequence: Synthetic

EGFP

<400> SEQUENCE: 3

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Lys Asp
                165                 170                 175

Gly Asn Gly Tyr Ile Ser Ala Ala Glu Leu Arg His Val Met Thr Asn
            180                 185                 190

Leu Asp Gly Ser Val Gln Leu Ala Asp His Tyr Gln Gln Asn Thr Pro
        195                 200                 205

Ile Gly Asp Gly Pro Val Leu Leu Pro Asp Asn His Tyr Leu Ser Thr
210                 215                 220

Gln Ser Ala Leu Ser Lys Asp Pro Asn Glu Lys Arg Asp His Ile Val
225                 230                 235                 240

Leu Leu Glu Phe Val Thr Ala Ala Gly Ile Thr Leu Gly Met Asp Glu
                245                 250                 255

Leu Tyr Lys

<210> SEQ ID NO 4
<211> LENGTH: 270
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 4

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

-continued

Gln His Asp Phe Phe Lys Ser Ala Met Pro Glu Gly Tyr Val Gln Glu
                85                  90                  95

Arg Thr Ile Phe Lys Asp Asp Gly Asn Tyr Lys Thr Arg Ala Glu
        100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 5
<211> LENGTH: 298
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 5

Met Leu Leu Ser Val Pro Leu Leu Leu Gly Leu Leu Gly Leu Ala Ala
1               5                   10                  15

Ala Asp Gly Ser Gly Pro Ser Arg Met Val Ser Lys Gly Glu Glu Leu
            20                  25                  30

Phe Thr Gly Val Val Pro Ile Leu Val Glu Leu Asp Gly Asp Leu Asn
        35                  40                  45

Gly His Lys Phe Ser Val Ser Gly Glu Gly Glu Gly Asp Ala Thr Tyr
    50                  55                  60

Gly Lys Leu Thr Leu Lys Phe Ile Cys Thr Thr Gly Lys Leu Pro Val
65                  70                  75                  80

Pro Trp Pro Thr Leu Val Thr Thr Leu Thr Tyr Gly Val Gln Cys Phe
                85                  90                  95

Ser Arg Tyr Pro Asp His Met Lys Gln His Asp Phe Phe Lys Ser Ala
            100                 105                 110

Met Pro Glu Gly Tyr Val Gln Glu Arg Thr Ile Phe Phe Lys Asp Asp
        115                 120                 125

Gly Asn Tyr Lys Thr Arg Ala Glu Val Lys Phe Glu Gly Asp Thr Leu
    130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Ser His Asn Val Tyr
                165                 170                 175

```
Ile Met Ala Asp Lys Gln Lys Asn Gly Ile Lys Val Asn Phe Lys Ile
            180                 185                 190

Arg His Asn Ile Glu Glu Glu Ile Arg Glu Ala Phe Arg Val Phe
            195                 200                 205

Asp Lys Asp Gly Asn Gly Tyr Ile Ser Ala Ala Glu Leu Arg His Val
            210                 215                 220

Met Thr Asn Leu Asp Gly Ser Val Gln Leu Ala Asp His Tyr Gln Gln
225                 230                 235                 240

Asn Thr Pro Ile Gly Asp Gly Pro Val Leu Leu Pro Asp Asn His Tyr
                245                 250                 255

Leu Ser Thr Gln Ser Ala Leu Ser Lys Asp Pro Asn Glu Lys Arg Asp
                260                 265                 270

His Ile Val Leu Leu Glu Phe Val Thr Ala Ala Gly Ile Thr Leu Gly
                275                 280                 285

Met Asp Glu Leu Tyr Lys Lys Asp Glu Leu
            290                 295

<210> SEQ ID NO 6
<211> LENGTH: 310
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 6

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Gly Ser Gly
            20                  25                  30

Pro Ser Arg Met Val Ser Lys Gly Met Val Ser Lys Gly Glu Glu Leu
        35                  40                  45

Phe Thr Gly Val Val Pro Ile Leu Val Glu Leu Asp Gly Asp Leu Asn
    50                  55                  60

Gly His Lys Phe Ser Val Ser Gly Glu Gly Glu Gly Asp Ala Thr Tyr
65                  70                  75                  80

Gly Lys Leu Thr Leu Lys Phe Ile Cys Thr Thr Gly Lys Leu Pro Val
                85                  90                  95

Pro Trp Pro Thr Leu Val Thr Thr Leu Thr Tyr Gly Val Gln Cys Phe
            100                 105                 110

Ser Arg Tyr Pro Asp His Met Lys Gln His Asp Phe Phe Lys Ser Ala
            115                 120                 125

Met Pro Glu Gly Tyr Val Gln Glu Arg Thr Ile Phe Phe Lys Asp Asp
        130                 135                 140

Gly Asn Tyr Lys Thr Arg Ala Glu Val Lys Phe Glu Gly Asp Thr Leu
145                 150                 155                 160

Val Asn Arg Ile Glu Leu Lys Gly Ile Asp Phe Lys Glu Asp Gly Asn
                165                 170                 175

Ile Leu Gly His Lys Leu Glu Tyr Asn Tyr Asn Ser His Asn Val Tyr
            180                 185                 190

Ile Met Ala Asp Lys Gln Lys Asn Gly Ile Lys Val Asn Phe Lys Ile
            195                 200                 205

Arg His Asn Ile Glu Glu Glu Ile Arg Glu Ala Phe Arg Val Phe
            210                 215                 220

Asp Lys Asp Gly Asn Gly Tyr Ile Ser Ala Ala Glu Leu Arg His Val
225                 230                 235                 240
```

-continued

```
Met Thr Asn Leu Asp Gly Ser Val Gln Leu Ala Asp His Tyr Gln Gln
            245                 250                 255

Asn Thr Pro Ile Gly Asp Gly Pro Val Leu Leu Pro Asp Asn His Tyr
        260                 265                 270

Leu Ser Thr Gln Ser Ala Leu Ser Lys Asp Pro Asn Glu Lys Arg Asp
    275                 280                 285

His Ile Val Leu Leu Glu Phe Val Thr Ala Ala Gly Ile Thr Leu Gly
    290                 295                 300

Met Asp Glu Leu Tyr Lys
305             310

<210> SEQ ID NO 7
<211> LENGTH: 271
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 7

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Ser Glu Glu
                165                 170                 175

Glu Lys Arg Glu Ala Glu Arg Val Phe Asp Lys Asp Gly Asn Gly Tyr
            180                 185                 190

Ile Ser Ala Ala Glu Leu Arg His Ala Ala Thr Asn Leu Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 8
<211> LENGTH: 270
```

```
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 8

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Glu Glu
                165                 170                 175

Ile Arg Glu Ala Phe Arg Val Phe Asn Lys Asp Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 9
<211> LENGTH: 270
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 9

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
```

```
            50                  55                  60
Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
                130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                    165                 170                 175

Ile Arg Glu Ala Phe Arg Val Phe Asn Lys Asn Gly Asn Gly Tyr Ile
                180                 185                 190

Ser Ala Ala Glu Leu Arg His Val Met Thr Asn Leu Asp Gly Ser Val
                195                 200                 205

Gln Leu Ala Asp His Tyr Gln Gln Asn Thr Pro Ile Gly Asp Gly Pro
                210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                    245                 250                 255

Thr Ala Ala Gly Ile Thr Leu Gly Met Asp Glu Leu Tyr Lys
                260                 265                 270

<210> SEQ ID NO 10
<211> LENGTH: 270
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 10

Met Val Ser Lys Gly Glu Glu Leu Phe Thr Gly Val Val Pro Ile Leu
 1               5                  10                  15

Val Glu Leu Asp Gly Asp Leu Asn Gly His Lys Phe Ser Val Ser Gly
                 20                  25                  30

Glu Gly Glu Gly Asp Ala Thr Tyr Gly Lys Leu Thr Leu Lys Phe Ile
                 35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
                130                 135                 140

Asn Tyr Asn Ser His Asn Val Tyr Ile Met Ala Asp Lys Gln Lys Asn
```

```
                145                 150                 155                 160
Gly Ile Lys Val Asn Phe Lys Ile Arg His Asn Ile Glu Glu Glu
                    165                 170                 175

Ile Arg Glu Ala Phe Arg Val Phe Asp Lys Asp Gly Asn Gly Tyr Ile
                    180                 185                 190

Ser Ala Ala Glu Leu Arg His Val Met Thr Asn Leu Asp Gly Ser Val
                195                 200                 205

Gln Leu Ala Asp His Tyr Gln Gln Asn Thr Pro Ile Gly Asp Gly Pro
            210                 215                 220

Val Asn Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                    245                 250                 255

Thr Ala Ala Gly Ile Thr Leu Gly Met Asp Glu Leu Tyr Lys
                260                 265                 270

<210> SEQ ID NO 11
<211> LENGTH: 251
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 11

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                    85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Lys Asp
                    165                 170                 175

Gly Asp Gly Thr Ile Thr Thr Lys Glu Asp Gly Ser Val Gln Leu Ala
                180                 185                 190

Asp His Tyr Gln Gln Asn Thr Pro Ile Gly Asp Gly Pro Val Leu Leu
            195                 200                 205

Pro Asp Asn His Tyr Leu Ser Thr Gln Ser Ala Leu Ser Lys Asp Pro
        210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
```

```
<210> SEQ ID NO 12
<211> LENGTH: 271
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 12

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Ser Arg Asn
                165                 170                 175

Ile Cys Asp Ile Ser Cys Asp Lys Phe Leu Asp Asp Asp Ile Thr Asp
            180                 185                 190

Asp Ile Met Cys Ala Lys Lys Ile Leu Asp Ile Lys Gly Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 13
<211> LENGTH: 271
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 13

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30
```

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
            85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Ser Arg Asn
                    165                 170                 175

Ile Cys Asp Ile Ser Ala Asp Lys Phe Leu Asp Asp Ile Thr Asp
                180                 185                 190

Asp Ile Met Cys Ala Lys Lys Ile Leu Asp Ile Lys Gly Asp Gly Ser
                195                 200                 205

Val Gln Leu Ala Asp His Tyr Gln Gln Asn Thr Pro Ile Gly Asp Gly
            210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 14
<211> LENGTH: 271
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 14

Met Val Ser Lys Gly Glu Glu Leu Phe Thr Gly Val Val Pro Ile Leu
 1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
            85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

```
Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Ser Arg Asn
                165                 170                 175

Ile Cys Asp Ile Ser Cys Asp Lys Phe Leu Asp Asp Ile Thr Asp
                180                 185                 190

Asp Ile Met Ala Ala Lys Lys Ile Leu Asp Ile Lys Gly Asp Gly Ser
            195                 200                 205

Val Gln Leu Ala Asp His Tyr Gln Gln Asn Thr Pro Ile Gly Asp Gly
        210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 15
<211> LENGTH: 271
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 15

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Ser Arg Asn
                165                 170                 175

Ile Cys Asp Ile Ser Ala Asp Lys Phe Leu Asp Asp Ile Thr Asp
                180                 185                 190

Asp Ile Met Ala Ala Lys Lys Ile Leu Asp Ile Lys Gly Asp Gly Ser
            195                 200                 205

Val Gln Leu Ala Asp His Tyr Gln Gln Asn Thr Pro Ile Gly Asp Gly
        210                 215                 220
```

```
Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
            245                 250                 255

Val Thr Ala Ala Gly Ile Thr Leu Gly Met Asp Glu Leu Tyr Lys
            260                 265                 270

<210> SEQ ID NO 16
<211> LENGTH: 251
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 16

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Lys Asp
                165                 170                 175

Gly Asn Gly Tyr Ile Ser Ala Ala Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Ala Leu Ser Lys Asp Pro
210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
                245                 250

<210> SEQ ID NO 17
<211> LENGTH: 262
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 17
```

```
Met Val Ser Lys Gly Glu Glu Leu Phe Thr Gly Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
            85                  90                  95

Arg Thr Ile Phe Phe Lys Asp Asp Gly Asn Tyr Lys Thr Arg Ala Glu
        100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
            165                 170                 175

Ile Arg Glu Ala Phe Arg Val Phe Asp Lys Asp Gly Asn Gly Tyr Ile
        180                 185                 190

Ser Ala Ala Glu Asp Gly Ser Val Gln Leu Ala Asp His Tyr Gln Gln
        195                 200                 205

Asn Thr Pro Ile Gly Asp Gly Pro Val Leu Leu Pro Asp Asn His Tyr
210                 215                 220

Leu Ser Thr Gln Ser Ala Leu Ser Lys Asp Pro Asn Glu Lys Arg Asp
225                 230                 235                 240

His Ile Val Leu Leu Glu Phe Val Thr Ala Ala Gly Ile Thr Leu Gly
            245                 250                 255

Met Asp Glu Leu Tyr Lys
            260

<210> SEQ ID NO 18
<211> LENGTH: 259
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 18

Met Val Ser Lys Gly Glu Glu Leu Phe Thr Gly Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
            85                  90                  95
```

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Lys Asp
                165                 170                 175

Gly Asn Gly Tyr Ile Ser Ala Ala Glu Leu Arg His Val Met Thr Asn
            180                 185                 190

Leu Asp Gly Ser Val Gln Leu Ala Asp His Tyr Gln Gln Asn Thr Pro
            195                 200                 205

Ile Gly Asp Gly Pro Val Leu Leu Pro Asp Asn His Tyr Leu Ser Thr
            210                 215                 220

Gln Ser Ala Leu Ser Lys Asp Pro Asn Glu Lys Arg Asp His Ile Val
225                 230                 235                 240

Leu Leu Glu Phe Val Thr Ala Ala Gly Ile Thr Leu Gly Met Asp Glu
            245                 250                 255

Leu Tyr Lys

<210> SEQ ID NO 19
<211> LENGTH: 270
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 19

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Arg His Val Met Thr Asn Leu Asp Gly Ser Val
```

```
                195                 200                 205
Gln Leu Ala Asp His Tyr Gln Gln Asn Thr Pro Ile Gly Asp Gly Pro
    210                 215                 220

Val Leu Pro Asp Asn His Tyr Leu Ser Thr Gln Ser Ala Leu Ser
225                 230                 235                 240

Lys Asp Pro Asn Glu Lys Arg Asp His Ile Val Leu Glu Phe Val
                245                 250                 255

Thr Ala Ala Gly Ile Thr Leu Gly Met Asp Glu Leu Tyr Lys
            260                 265                 270

<210> SEQ ID NO 20
<211> LENGTH: 298
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 20

Met Leu Leu Ser Val Pro Leu Leu Gly Leu Leu Gly Leu Ala Ala
1               5                   10                  15

Ala Asp Gly Ser Gly Pro Ser Arg Met Val Ser Lys Gly Glu Glu Leu
                20                  25                  30

Phe Thr Gly Val Val Pro Ile Leu Val Glu Leu Asp Gly Asp Leu Asn
            35                  40                  45

Gly His Lys Phe Ser Val Ser Gly Glu Gly Glu Gly Asp Ala Thr Tyr
        50                  55                  60

Gly Lys Leu Thr Leu Lys Phe Ile Cys Thr Thr Gly Lys Leu Pro Val
65                  70                  75                  80

Pro Trp Pro Thr Leu Val Thr Thr Leu Thr Tyr Gly Val Gln Cys Phe
                85                  90                  95

Ser Arg Tyr Pro Asp His Met Lys Gln His Asp Phe Phe Lys Ser Ala
                100                 105                 110

Met Pro Glu Gly Tyr Val Gln Glu Arg Thr Ile Phe Phe Lys Asp Asp
            115                 120                 125

Gly Asn Tyr Lys Thr Arg Ala Glu Val Lys Phe Glu Gly Asp Thr Leu
        130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Ser His Asn Val Tyr
                165                 170                 175

Ile Thr Ala Asp Lys Gln Lys Asn Gly Ile Lys Ala Asn Phe Lys Ile
            180                 185                 190

Arg His Asn Ile Glu Glu Glu Ile Arg Glu Ala Phe Arg Val Phe
        195                 200                 205

Asp Lys Asp Gly Asn Gly Tyr Ile Ser Ala Ala Glu Leu Arg His Val
    210                 215                 220

Met Thr Asn Leu Asp Gly Ser Val Gln Leu Ala Asp His Tyr Gln Gln
225                 230                 235                 240

Asn Thr Pro Ile Gly Asp Gly Pro Val Leu Leu Pro Asp Asn His Tyr
                245                 250                 255

Leu Ser Thr Gln Ser Ala Leu Ser Lys Asp Pro Asn Glu Lys Arg Asp
            260                 265                 270

His Ile Val Leu Leu Glu Phe Val Thr Ala Ala Gly Ile Thr Leu Gly
        275                 280                 285

Met Asp Glu Leu Tyr Lys Lys Asp Glu Leu
```

```
                290                 295

<210> SEQ ID NO 21
<211> LENGTH: 310
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 21

Met Ser Val Leu Thr Pro Leu Leu Arg Gly Leu Thr Gly Ser Ala
1               5                   10                  15

Arg Arg Leu Pro Val Pro Arg Ala Lys Ile His Ser Leu Gly Ser Gly
            20                  25                  30

Pro Ser Arg Met Val Ser Lys Gly Met Val Ser Lys Gly Glu Glu Leu
            35                  40                  45

Phe Thr Gly Val Val Pro Ile Leu Val Glu Leu Asp Gly Asp Leu Asn
50                  55                  60

Gly His Lys Phe Ser Val Ser Gly Glu Gly Glu Gly Asp Ala Thr Tyr
65                  70                  75                  80

Gly Lys Leu Thr Leu Lys Phe Ile Cys Thr Thr Gly Lys Leu Pro Val
                85                  90                  95

Pro Trp Pro Thr Leu Val Thr Thr Leu Thr Tyr Gly Val Gln Cys Phe
            100                 105                 110

Ser Arg Tyr Pro Asp His Met Lys Gln His Asp Phe Phe Lys Ser Ala
            115                 120                 125

Met Pro Glu Gly Tyr Val Gln Glu Arg Thr Ile Phe Phe Lys Asp Asp
            130                 135                 140

Gly Asn Tyr Lys Thr Arg Ala Glu Val Lys Phe Glu Gly Asp Thr Leu
145                 150                 155                 160

Val Asn Arg Ile Glu Leu Lys Gly Ile Asp Phe Lys Glu Asp Gly Asn
                165                 170                 175

Ile Leu Gly His Lys Leu Glu Tyr Asn Tyr Asn Ser His Asn Val Tyr
            180                 185                 190

Ile Thr Ala Asp Lys Gln Lys Asn Gly Ile Lys Ala Asn Phe Lys Ile
            195                 200                 205

Arg His Asn Ile Glu Glu Glu Ile Arg Glu Ala Phe Arg Val Phe
            210                 215                 220

Asp Lys Asp Gly Asn Gly Tyr Ile Ser Ala Ala Glu Leu Arg His Val
225                 230                 235                 240

Met Thr Asn Leu Asp Gly Ser Val Gln Leu Ala Asp His Tyr Gln Gln
                245                 250                 255

Asn Thr Pro Ile Gly Asp Gly Pro Val Leu Leu Pro Asp Asn His Tyr
            260                 265                 270

Leu Ser Thr Gln Ser Ala Leu Ser Lys Asp Pro Asn Glu Lys Arg Asp
            275                 280                 285

His Ile Val Leu Leu Glu Phe Val Thr Ala Ala Gly Ile Thr Leu Gly
            290                 295                 300

Met Asp Glu Leu Tyr Lys
305                 310

<210> SEQ ID NO 22
<211> LENGTH: 271
<212> TYPE: PRT
<213> ORGANISM: artificial sequence
<220> FEATURE:
<223> OTHER INFORMATION: Description of Artificial Sequence: Synthetic
```

EGFP

<400> SEQUENCE: 22

Met Val Ser Lys Gly Glu Glu Leu Phe Thr Gly Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Glu Glu
                165                 170                 175

Glu Lys Arg Glu Ala Glu Arg Val Phe Asp Lys Asp Gly Asn Gly Tyr
            180                 185                 190

Ile Ser Ala Ala Glu Leu Arg His Ala Ala Thr Asn Leu Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 23
<211> LENGTH: 270
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 23

Met Val Ser Lys Gly Glu Glu Leu Phe Thr Gly Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

```
Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asn Lys Asp Gly Asn Gly Tyr Ile
                180                 185                 190

Ser Ala Ala Glu Leu Arg His Val Met Thr Asn Leu Asp Gly Ser Val
                195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
                260                 265                 270

<210> SEQ ID NO 24
<211> LENGTH: 270
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 24

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175
```

```
Ile Arg Glu Ala Phe Arg Val Phe Asn Lys Asn Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 25
<211> LENGTH: 270
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 25

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Asn Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270
```

<210> SEQ ID NO 26
<211> LENGTH: 251
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 26

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Lys Asp
                165                 170                 175

Gly Asp Gly Thr Ile Thr Thr Lys Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Ala Leu Ser Lys Asp Pro
    210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
                245                 250

<210> SEQ ID NO 27
<211> LENGTH: 271
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 27

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
                50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                    85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Arg Asn
                165                 170                 175

Ile Cys Asp Ile Ser Cys Asp Lys Phe Leu Asp Asp Asp Ile Thr Asp
                180                 185                 190

Asp Ile Met Cys Ala Lys Lys Ile Leu Asp Ile Lys Gly Asp Gly Ser
                195                 200                 205

Val Gln Leu Ala Asp His Tyr Gln Gln Asn Thr Pro Ile Gly Asp Gly
            210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
                260                 265                 270

<210> SEQ ID NO 28
<211> LENGTH: 271
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 28

Met Val Ser Lys Gly Glu Glu Leu Phe Thr Gly Val Val Pro Ile Leu
 1               5                  10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
     50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                    85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
            130                 135                 140

```
Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Arg Asn
                165                 170                 175

Ile Cys Asp Ile Ser Ala Asp Lys Phe Leu Asp Asp Ile Thr Asp
                180                 185                 190

Asp Ile Met Cys Ala Lys Lys Ile Leu Asp Ile Lys Gly Asp Gly Ser
            195                 200                 205

Val Gln Leu Ala Asp His Tyr Gln Gln Asn Thr Pro Ile Gly Asp Gly
            210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 29
<211> LENGTH: 271
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 29

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Arg Asn
                165                 170                 175

Ile Cys Asp Ile Ser Cys Asp Lys Phe Leu Asp Asp Ile Thr Asp
                180                 185                 190

Asp Ile Met Ala Ala Lys Lys Ile Leu Asp Ile Lys Gly Asp Gly Ser
            195                 200                 205

Val Gln Leu Ala Asp His Tyr Gln Gln Asn Thr Pro Ile Gly Asp Gly
            210                 215                 220

Pro Val Leu Leu Pro Asp Asn His Tyr Leu Ser Thr Gln Ser Ala Leu
225                 230                 235                 240
```

```
Ser Lys Asp Pro Asn Glu Lys Arg Asp His Ile Val Leu Leu Glu Phe
            245                 250                 255

Val Thr Ala Ala Gly Ile Thr Leu Gly Met Asp Glu Leu Tyr Lys
        260                 265                 270

<210> SEQ ID NO 30
<211> LENGTH: 271
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 30

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Arg Asn
                165                 170                 175

Ile Cys Asp Ile Ser Ala Asp Lys Phe Leu Asp Asp Ile Thr Asp
            180                 185                 190

Asp Ile Met Ala Ala Lys Lys Ile Leu Asp Ile Lys Gly Asp Gly Ser
        195                 200                 205

Val Gln Leu Ala Asp His Tyr Gln Gln Asn Thr Pro Ile Gly Asp Gly
        210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
            245                 250                 255

Val Thr Ala Ala Gly Ile Thr Leu Gly Met Asp Glu Leu Tyr Lys
        260                 265                 270

<210> SEQ ID NO 31
<211> LENGTH: 251
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 31

Met Val Ser Lys Gly Glu Glu Leu Phe Thr Gly Val Val Pro Ile Leu
```

```
                1               5                    10                  15
              Val Glu Leu Asp Gly Asp Leu Asn Gly His Lys Phe Ser Val Ser Gly
                           20                  25                  30

Glu Gly Glu Gly Asp Ala Thr Tyr Gly Lys Leu Thr Leu Lys Phe Ile
                           35                  40                  45

Cys Thr Thr Gly Lys Leu Pro Val Pro Trp Pro Thr Leu Val Thr Thr
                           50                  55                  60

Leu Thr Tyr Gly Val Gln Cys Phe Ser Arg Tyr Pro Asp His Met Lys
               65                  70                  75                  80

Gln His Asp Phe Phe Lys Ser Ala Met Pro Glu Gly Tyr Val Gln Glu
                               85                  90                  95

Arg Thr Ile Ser Phe Lys Asp Asp Gly Asn Tyr Lys Thr Arg Ala Glu
                              100                 105                 110

Val Lys Phe Glu Gly Asp Thr Leu Val Asn Arg Ile Glu Leu Lys Gly
                              115                 120                 125

Ile Asp Phe Lys Glu Asp Gly Asn Ile Leu Gly His Lys Leu Glu Tyr
                              130                 135                 140

Asn Tyr Asn Ser His Asn Val Tyr Ile Thr Ala Asp Lys Gln Lys Asn
              145                 150                 155                 160

Gly Ile Lys Ala Asn Phe Lys Ile Arg His Asn Ile Glu Asp Lys Asp
                              165                 170                 175

Gly Asn Gly Tyr Ile Ser Ala Ala Glu Asp Gly Ser Val Gln Leu Ala
                              180                 185                 190

Asp His Tyr Gln Gln Asn Thr Pro Ile Gly Asp Gly Pro Val Leu Leu
                              195                 200                 205

Pro Asp Asn His Tyr Leu Ser Thr Gln Ser Ala Leu Ser Lys Asp Pro
                              210                 215                 220

Asn Glu Lys Arg Asp His Ile Val Leu Leu Glu Phe Val Thr Ala Ala
              225                 230                 235                 240

Gly Ile Thr Leu Gly Met Asp Glu Leu Tyr Lys
                              245                 250

<210> SEQ ID NO 32
<211> LENGTH: 262
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 32

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
             20                  25                  30

Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
             50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                 85                  90                  95

Arg Thr Ile Ser Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
```

```
                    115                 120                 125
Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
                180                 185                 190

Ser Ala Ala Glu Asp Gly Ser Val Gln Leu Ala Asp His Tyr Gln Gln
                195                 200                 205

Asn Thr Pro Ile Gly Asp Gly Pro Val Leu Leu Pro Asp Asn His Tyr
            210                 215                 220

Leu Ser Thr Gln Ser Ala Leu Ser Lys Asp Pro Asn Glu Lys Arg Asp
225                 230                 235                 240

His Ile Val Leu Leu Glu Phe Val Thr Ala Ala Gly Ile Thr Leu Gly
                    245                 250                 255

Met Asp Glu Leu Tyr Lys
                260

<210> SEQ ID NO 33
<211> LENGTH: 259
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 33

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Lys Asp
                165                 170                 175

Gly Asn Gly Tyr Ile Ser Ala Ala Glu Leu Arg His Val Met Thr Asn
                180                 185                 190

Leu Asp Gly Ser Val Gln Leu Ala Asp His Tyr Gln Gln Asn Thr Pro
        195                 200                 205

Ile Gly Asp Gly Pro Val Leu Leu Pro Asp Asn His Tyr Leu Ser Thr
```

-continued

```
                    210                 215                 220
Gln Ser Ala Leu Ser Lys Asp Pro Asn Glu Lys Arg Asp His Ile Val
225                 230                 235                 240

Leu Leu Glu Phe Val Thr Ala Ala Gly Ile Thr Leu Gly Met Asp Glu
                245                 250                 255

Leu Tyr Lys

<210> SEQ ID NO 34
<211> LENGTH: 270
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 34

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 35
<211> LENGTH: 298
<212> TYPE: PRT
<213> ORGANISM: artificial sequence
<220> FEATURE:
<223> OTHER INFORMATION: Description of Artificial Sequence: Synthetic
      EGFP
```

```
<400> SEQUENCE: 35

Met Leu Leu Ser Val Pro Leu Leu Leu Gly Leu Gly Leu Ala Ala
1               5                   10                  15

Ala Asp Gly Ser Gly Pro Ser Arg Met Val Ser Lys Gly Glu Glu Leu
            20                  25                  30

Phe Thr Gly Val Val Pro Ile Leu Val Glu Leu Asp Gly Asp Leu Asn
        35                  40                  45

Gly His Lys Phe Ser Val Ser Gly Glu Gly Glu Gly Asp Ala Thr Tyr
    50                  55                  60

Gly Lys Leu Thr Leu Lys Phe Ile Cys Thr Thr Gly Lys Leu Pro Val
65                  70                  75                  80

Pro Trp Pro Thr Leu Val Thr Thr Leu Thr Tyr Gly Val Gln Cys Phe
                85                  90                  95

Ser Arg Tyr Pro Asp His Met Lys Gln His Asp Phe Phe Lys Ser Ala
            100                 105                 110

Met Pro Glu Gly Tyr Val Gln Glu Arg Thr Ile Ser Phe Lys Asp Asp
        115                 120                 125

Gly Asn Tyr Lys Thr Arg Ala Glu Val Lys Phe Glu Gly Asp Thr Leu
    130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Ser His Asn Val Tyr
                165                 170                 175

Ile Thr Ala Asp Lys Gln Lys Asn Gly Ile Lys Ala Asn Phe Lys Ile
            180                 185                 190

Arg His Asn Ile Glu Glu Glu Ile Arg Glu Ala Phe Arg Val Phe
        195                 200                 205

Asp Lys Asp Gly Asn Gly Tyr Ile Ser Ala Ala Glu Leu Arg His Val
    210                 215                 220

Met Thr Asn Leu Asp Gly Ser Val Gln Leu Ala Asp His Tyr Gln Gln
225                 230                 235                 240

Asn Thr Pro Ile Gly Asp Gly Pro Val Leu Leu Pro Asp Asn His Tyr
                245                 250                 255

Leu Ser Thr Gln Ser Ala Leu Ser Lys Asp Pro Asn Glu Lys Arg Asp
            260                 265                 270

His Ile Val Leu Leu Glu Phe Val Thr Ala Ala Gly Ile Thr Leu Gly
        275                 280                 285

Met Asp Glu Leu Tyr Lys Lys Asp Glu Leu
    290                 295

<210> SEQ ID NO 36
<211> LENGTH: 310
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 36

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Gly Ser Gly
            20                  25                  30

Pro Ser Arg Met Val Ser Lys Gly Met Val Ser Lys Gly Glu Glu Leu
        35                  40                  45
```

```
Phe Thr Gly Val Val Pro Ile Leu Val Glu Leu Asp Gly Asp Leu Asn
 50                  55                  60

Gly His Lys Phe Ser Val Ser Gly Glu Gly Glu Gly Asp Ala Thr Tyr
 65                  70                  75                  80

Gly Lys Leu Thr Leu Lys Phe Ile Cys Thr Thr Gly Lys Leu Pro Val
                 85                  90                  95

Pro Trp Pro Thr Leu Val Thr Thr Leu Thr Tyr Gly Val Gln Cys Phe
            100                 105                 110

Ser Arg Tyr Pro Asp His Met Lys Gln His Asp Phe Phe Lys Ser Ala
        115                 120                 125

Met Pro Glu Gly Tyr Val Gln Glu Arg Thr Ile Ser Phe Lys Asp Asp
130                 135                 140

Gly Asn Tyr Lys Thr Arg Ala Glu Val Lys Phe Glu Gly Asp Thr Leu
145                 150                 155                 160

Val Asn Arg Ile Glu Leu Lys Gly Ile Asp Phe Lys Glu Asp Gly Asn
                165                 170                 175

Ile Leu Gly His Lys Leu Glu Tyr Asn Tyr Asn Ser His Asn Val Tyr
            180                 185                 190

Ile Thr Ala Asp Lys Gln Lys Asn Gly Ile Lys Ala Asn Phe Lys Ile
        195                 200                 205

Arg His Asn Ile Glu Glu Glu Ile Arg Glu Ala Phe Arg Val Phe
210                 215                 220

Asp Lys Asp Gly Asn Gly Tyr Ile Ser Ala Ala Glu Leu Arg His Val
225                 230                 235                 240

Met Thr Asn Leu Asp Gly Ser Val Gln Leu Ala Asp His Tyr Gln Gln
                245                 250                 255

Asn Thr Pro Ile Gly Asp Gly Pro Val Leu Leu Pro Asp Asn His Tyr
            260                 265                 270

Leu Ser Thr Gln Ser Ala Leu Ser Lys Asp Pro Asn Glu Lys Arg Asp
        275                 280                 285

His Ile Val Leu Leu Glu Phe Val Thr Ala Ala Gly Ile Thr Leu Gly
290                 295                 300

Met Asp Glu Leu Tyr Lys
305                 310

<210> SEQ ID NO 37
<211> LENGTH: 271
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 37

Met Val Ser Lys Gly Glu Glu Leu Phe Thr Gly Val Val Pro Ile Leu
1               5                  10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95
```

```
Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Glu Glu
                165                 170                 175

Glu Lys Arg Glu Ala Glu Arg Val Phe Asp Lys Asp Gly Asn Gly Tyr
            180                 185                 190

Ile Ser Ala Ala Glu Leu Arg His Ala Ala Thr Asn Leu Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 38
<211> LENGTH: 270
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 38

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu Glu
                165                 170                 175

Ile Arg Glu Ala Phe Arg Val Phe Asn Lys Asp Gly Asn Gly Tyr Ile
            180                 185                 190
```

```
Ser Ala Ala Glu Leu Arg His Val Met Thr Asn Leu Asp Gly Ser Val
            195                 200                 205

Gln Leu Ala Asp His Tyr Gln Gln Asn Thr Pro Ile Gly Asp Gly Pro
        210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 39
<211> LENGTH: 270
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 39

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asn Lys Asn Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 40
<211> LENGTH: 270
```

```
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 40

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Asn Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
                260                 265                 270

<210> SEQ ID NO 41
<211> LENGTH: 251
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 41

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
```

```
                    50                  55                  60
Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                     85                  90                  95

Arg Thr Ile Ser Phe Lys Asp Asp Gly Asn Tyr Lys Thr Arg Ala Glu
                    100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
                130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Lys Asp
                    165                 170                 175

Gly Asp Gly Thr Ile Thr Thr Lys Glu Asp Gly Ser Val Gln Leu Ala
                180                 185                 190

Asp His Tyr Gln Gln Asn Thr Pro Ile Gly Asp Gly Pro Val Leu Leu
                195                 200                 205

Pro Asp Asn His Tyr Leu Ser Thr Gln Ser Ala Leu Ser Lys Asp Pro
210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
                245                 250

<210> SEQ ID NO 42
<211> LENGTH: 271
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 42

Met Val Ser Lys Gly Glu Glu Leu Phe Thr Gly Val Val Pro Ile Leu
  1               5                  10                  15

Val Glu Leu Asp Gly Asp Leu Asn Gly His Lys Phe Ser Val Ser Gly
                 20                  25                  30

Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                     85                  90                  95

Arg Thr Ile Ser Phe Lys Asp Asp Gly Asn Tyr Lys Thr Arg Ala Glu
                    100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
                130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Arg Asn
```

```
                         165                 170                 175
Ile Cys Asp Ile Ser Cys Asp Lys Phe Leu Asp Asp Ile Thr Asp
            180                 185                 190

Asp Ile Met Cys Ala Lys Lys Ile Leu Asp Ile Lys Gly Asp Gly Ser
            195                 200                 205

Val Gln Leu Ala Asp His Tyr Gln Gln Asn Thr Pro Ile Gly Asp Gly
            210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 43
<211> LENGTH: 271
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 43

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Arg Asn
                165                 170                 175

Ile Cys Asp Ile Ser Ala Asp Lys Phe Leu Asp Asp Ile Thr Asp
            180                 185                 190

Asp Ile Met Cys Ala Lys Lys Ile Leu Asp Ile Lys Gly Asp Gly Ser
            195                 200                 205

Val Gln Leu Ala Asp His Tyr Gln Gln Asn Thr Pro Ile Gly Asp Gly
            210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
```

<210> SEQ ID NO 44
<211> LENGTH: 271
<212> TYPE: PRT
<213> ORGANISM: artificial sequence
<220> FEATURE:
<223> OTHER INFORMATION: Description of Artificial Sequence: Synthetic EGFP

<400> SEQUENCE: 44

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Arg Asn
                165                 170                 175

Ile Cys Asp Ile Ser Cys Asp Lys Phe Leu Asp Asp Asp Ile Thr Asp
            180                 185                 190

Asp Ile Met Ala Ala Lys Lys Ile Leu Asp Ile Lys Gly Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 45
<211> LENGTH: 271
<212> TYPE: PRT
<213> ORGANISM: artificial sequence
<220> FEATURE:
<223> OTHER INFORMATION: Description of Artificial Sequence: Synthetic EGFP

<400> SEQUENCE: 45

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Arg Asn
                165                 170                 175

Ile Cys Asp Ile Ser Ala Asp Lys Phe Leu Asp Asp Ile Thr Asp
            180                 185                 190

Asp Ile Met Ala Ala Lys Lys Ile Leu Asp Ile Lys Gly Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 46
<211> LENGTH: 251
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 46

Met Val Ser Lys Gly Glu Glu Leu Phe Thr Gly Val Val Pro Ile Leu
  1               5                  10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

```
Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Asp Lys
145                 150                 155                 160

Asp Gly Asn Gly Tyr Ile Ser Ala Ala Glu Lys Asn Gly Ile Lys Val
                165                 170                 175

Asn Phe Lys Ile Arg His Asn Ile Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Ala Leu Ser Lys Asp Pro
    210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
                245                 250

<210> SEQ ID NO 47
<211> LENGTH: 270
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 47

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Glu Glu
145                 150                 155                 160

Glu Ile Arg Glu Ala Phe Arg Val Phe Asp Lys Asp Gly Asn Gly Tyr
                165                 170                 175

Ile Ser Ala Ala Glu Leu Arg His Val Met Thr Asn Leu Lys Asn Gly
            180                 185                 190

Ile Lys Val Asn Phe Lys Ile Arg His Asn Ile Glu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240
```

```
Lys Asp Pro Asn Glu Lys Arg Asp His Ile Val Leu Leu Glu Phe Val
            245                 250                 255

Thr Ala Ala Gly Ile Thr Leu Gly Met Asp Glu Leu Tyr Lys
            260                 265                 270

<210> SEQ ID NO 48
<211> LENGTH: 251
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 48

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Asp Lys
145                 150                 155                 160

Asp Gly Asn Gly Tyr Ile Ser Ala Ala Glu Lys Asn Gly Ile Lys Ala
                165                 170                 175

Asn Phe Lys Ile Arg His Asn Ile Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Ala Leu Ser Lys Asp Pro
    210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
                245                 250

<210> SEQ ID NO 49
<211> LENGTH: 270
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 49

Met Val Ser Lys Gly Glu Glu Leu Phe Thr Gly Val Val Pro Ile Leu
1               5                   10                  15
```

```
Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Glu Glu
145                 150                 155                 160

Glu Ile Arg Glu Ala Phe Arg Val Phe Asp Lys Asp Gly Asn Gly Tyr
            165                 170                 175

Ile Ser Ala Ala Glu Leu Arg His Val Met Thr Asn Leu Lys Asn Gly
        180                 185                 190

Ile Lys Ala Asn Phe Lys Ile Arg His Asn Ile Glu Asp Gly Ser Val
    195                 200                 205

Gln Leu Ala Asp His Tyr Gln Gln Asn Thr Pro Ile Gly Asp Gly Pro
210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
            245                 250                 255

Thr Ala Ala Gly Ile Thr Leu Gly Met Asp Glu Leu Tyr Lys
            260                 265                 270

<210> SEQ ID NO 50
<211> LENGTH: 251
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 50

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110
```

```
Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Asp Lys
145                 150                 155                 160

Asp Gly Asn Gly Tyr Ile Ser Ala Ala Glu Lys Asn Gly Ile Lys Ala
                165                 170                 175

Asn Phe Lys Ile Arg His Asn Ile Glu Asp Gly Ser Val Gln Leu Ala
                180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Ala Leu Ser Lys Asp Pro
210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
                245                 250
```

<210> SEQ ID NO 51
<211> LENGTH: 270
<212> TYPE: PRT
<213> ORGANISM: artificial sequence
<220> FEATURE:
<223> OTHER INFORMATION: Description of Artificial Sequence: Synthetic EGFP

<400> SEQUENCE: 51

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Glu Glu
145                 150                 155                 160

Glu Ile Arg Glu Ala Phe Arg Val Phe Asp Lys Asp Gly Asn Gly Tyr
                165                 170                 175

Ile Ser Ala Ala Glu Leu Arg His Val Met Thr Asn Leu Lys Asn Gly
                180                 185                 190

Ile Lys Ala Asn Phe Lys Ile Arg His Asn Ile Glu Asp Gly Ser Val
        195                 200                 205

Gln Leu Ala Asp His Tyr Gln Gln Asn Thr Pro Ile Gly Asp Gly Pro
210                 215                 220
```

```
Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270
```

<210> SEQ ID NO 52
<211> LENGTH: 270
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 52

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Glu Glu Ile Arg
                165                 170                 175

Glu Ala Phe Arg Val Phe Asp Lys Asp Gly Asn Gly Tyr Ile Ser Ala
            180                 185                 190

Ala Glu Leu Arg His Val Met Thr Asn Leu Ile Glu Asp Gly Ser Val
        195                 200                 205

Gln Leu Ala Asp His Tyr Gln Gln Asn Thr Pro Ile Gly Asp Gly Pro
210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270
```

<210> SEQ ID NO 53
<211> LENGTH: 273
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 53

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Thr Glu Glu Gln Ile
                165                 170                 175

Ala Glu Phe Lys Glu Ala Phe Ser Leu Phe Asp Lys Asp Gly Asp Gly
            180                 185                 190

Thr Ile Thr Thr Lys Glu Leu Gly Thr Val Met Arg Ser Ile Glu Asp
        195                 200                 205

Gly Ser Val Gln Leu Ala Asp His Tyr Gln Gln Asn Thr Pro Ile Gly
210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
            260                 265                 270

Lys

<210> SEQ ID NO 54
<211> LENGTH: 270
<212> TYPE: PRT
<213> ORGANISM: artificial sequence
<220> FEATURE:
<223> OTHER INFORMATION: Description of Artificial Sequence: Synthetic EGFP

<400> SEQUENCE: 54

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

```
Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Glu Glu Glu Ile Arg
                165                 170                 175

Glu Ala Phe Arg Val Phe Asp Lys Asp Gly Asn Gly Tyr Ile Ser Ala
            180                 185                 190

Ala Glu Leu Arg His Val Met Thr Asn Leu Ile Glu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 55
<211> LENGTH: 273
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 55

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Thr Glu Glu Gln Ile
                165                 170                 175
```

```
Ala Glu Phe Lys Glu Ala Phe Ser Leu Phe Asp Lys Asp Gly Asp Gly
            180                 185                 190

Thr Ile Thr Thr Lys Glu Leu Gly Thr Val Met Arg Ser Ile Glu Asp
        195                 200                 205

Gly Ser Val Gln Leu Ala Asp His Tyr Gln Gln Asn Thr Pro Ile Gly
    210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
            260                 265                 270

Lys

<210> SEQ ID NO 56
<211> LENGTH: 270
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 56

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Glu Glu Ile Arg
                165                 170                 175

Glu Ala Phe Arg Val Phe Asp Lys Asp Gly Asn Gly Tyr Ile Ser Ala
            180                 185                 190

Ala Glu Leu Arg His Val Met Thr Asn Leu Ile Glu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255
```

```
Thr Ala Ala Gly Ile Thr Leu Gly Met Asp Glu Leu Tyr Lys
            260                 265                 270

<210> SEQ ID NO 57
<211> LENGTH: 273
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 57

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Thr Glu Glu Gln Ile
                165                 170                 175

Ala Glu Phe Lys Glu Ala Phe Ser Leu Phe Asp Lys Asp Gly Asp Gly
            180                 185                 190

Thr Ile Thr Thr Lys Glu Leu Gly Thr Val Met Arg Ser Ile Glu Asp
        195                 200                 205

Gly Ser Val Gln Leu Ala Asp His Tyr Gln Gln Asn Thr Pro Ile Gly
210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
            260                 265                 270

Lys

<210> SEQ ID NO 58
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 58

Met Val Ser Lys Gly Glu Glu Leu Phe Thr Gly Val Val Pro Ile Leu
1               5                   10                  15
```

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Asp Phe Glu Gly Asp Thr Leu Asn Asn Asp Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
 210                 215                 220

Val Thr Ala Ala Gly Ile Thr Leu Gly Met Asp Glu Leu Tyr Lys
225                 230                 235

<210> SEQ ID NO 59
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 59

Met Val Ser Lys Gly Glu Glu Leu Phe Thr Gly Val Val Pro Ile Asn
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Asn Asn Asp Ile Glu Leu Lys Gly
            115                 120                 125

Ile Asp Phe Lys Glu Asp Gly Asn Ile Leu Gly His Lys Leu Glu Tyr
        130                 135                 140

```
Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 60
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 60

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Asp Glu Asp Gly Asp
                165                 170                 175

Val Asn Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 61
<211> LENGTH: 239
<212> TYPE: PRT
<213> ORGANISM: artificial sequence
```

```
<220> FEATURE:
<223> OTHER INFORMATION: Description of Artificial Sequence: Synthetic
      EGFP

<400> SEQUENCE: 61

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Asp
65                  70                  75                  80

Gln His Asp Phe Phe Asp Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Asn Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
210                 215                 220

Val Thr Ala Ala Gly Ile Thr Leu Gly Met Asp Glu Leu Tyr Lys
225                 230                 235

<210> SEQ ID NO 62
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 62

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Asp
65                  70                  75                  80

Gln His Asp Phe Phe Lys Asp Ala Met Pro Glu Gly Tyr Val Gln Glu
                85                  90                  95
```

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Asn Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 63
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 63

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Asn Lys
65                  70                  75                  80

Gln Asp Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn Asp Tyr Leu Ser Thr Gln Ser Ala Leu
        195                 200                 205

Ser Lys Asp Pro Asn Glu Lys Arg Asp His Ile Val Leu Leu Glu Phe
    210                 215                 220
```

-continued

Val Thr Ala Ala Gly Asp Thr Leu Gly Met Asp Glu Leu Tyr Lys
225                 230                 235

<210> SEQ ID NO 64
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 64

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Asp Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Glu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 65
<211> LENGTH: 267
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 65

Met Leu Leu Ser Val Pro Leu Leu Leu Gly Leu Leu Gly Leu Ala Ala
1               5                   10                  15

Ala Asp Gly Ser Gly Pro Ser Arg Met Val Ser Lys Gly Glu Glu Leu
            20                  25                  30

Phe Thr Gly Val Val Pro Ile Leu Val Glu Leu Asp Gly Asp Leu Asn
        35                  40                  45

Gly His Lys Phe Ser Val Ser Gly Glu Gly Glu Gly Asp Ala Thr Tyr

```
                50                  55                  60
Gly Lys Leu Thr Leu Lys Phe Ile Cys Thr Thr Gly Lys Leu Pro Val
 65                  70                  75                  80

Pro Trp Pro Thr Leu Val Thr Thr Leu Thr Tyr Gly Val Gln Cys Phe
                 85                  90                  95

Ser Arg Tyr Pro Asp His Met Lys Gln His Asp Phe Phe Lys Asp Ala
                100                 105                 110

Met Pro Glu Gly Tyr Val Gln Glu Arg Thr Ile Phe Phe Lys Asp Asp
            115                 120                 125

Gly Asn Tyr Lys Thr Arg Ala Glu Val Lys Phe Glu Gly Asp Thr Leu
        130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Ser His Asn Val Tyr
                165                 170                 175

Ile Met Ala Asp Lys Gln Lys Asn Gly Ile Lys Val Asn Phe Lys Ile
            180                 185                 190

Arg His Asn Ile Glu Asp Gly Ser Val Gln Leu Ala Asp His Tyr Gln
        195                 200                 205

Gln Asn Thr Pro Ile Gly Asp Gly Pro Val Glu Leu Pro Asp Asn His
    210                 215                 220

Tyr Leu Ser Thr Gln Ser Ala Leu Ser Lys Asp Pro Asn Glu Lys Arg
225                 230                 235                 240

Asp His Ile Val Leu Leu Glu Phe Val Thr Ala Ala Gly Ile Thr Leu
                245                 250                 255

Gly Met Asp Glu Leu Tyr Lys Lys Asp Glu Leu
            260                 265

<210> SEQ ID NO 66
<211> LENGTH: 274
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 66

Met Ser Val Leu Thr Pro Leu Leu Leu Arg Gly Leu Thr Gly Ser Ala
 1               5                  10                  15

Arg Arg Leu Pro Val Pro Arg Ala Lys Ile His Ser Leu Gly Ser Gly
                20                  25                  30

Pro Ser Arg Met Val Ser Lys Gly Glu Glu Leu Phe Thr Gly Val Val
             35                  40                  45

Pro Ile Leu Val Glu Leu Asp Gly Asp Leu Asn Gly His Lys Phe Ser
         50                  55                  60

Val Ser Gly Glu Gly Glu Gly Asp Ala Thr Tyr Gly Lys Leu Thr Leu
 65                  70                  75                  80

Lys Phe Ile Cys Thr Thr Gly Lys Leu Pro Val Pro Trp Pro Thr Leu
                 85                  90                  95

Val Thr Thr Leu Thr Tyr Gly Val Gln Cys Phe Ser Arg Tyr Pro Asp
                100                 105                 110

His Met Lys Gln His Asp Phe Phe Lys Asp Ala Met Pro Glu Gly Tyr
            115                 120                 125

Val Gln Glu Arg Thr Ile Phe Phe Lys Asp Asp Gly Asn Tyr Lys Thr
        130                 135                 140

Arg Ala Glu Val Lys Phe Glu Gly Asp Thr Leu Val Asn Arg Ile Glu
```

```
                 145                 150                 155                 160
Leu Lys Gly Ile Asp Phe Lys Glu Asp Gly Asn Ile Leu Gly His Lys
                165                 170                 175

Leu Glu Tyr Asn Tyr Asn Ser His Asn Val Tyr Ile Met Ala Asp Lys
            180                 185                 190

Gln Lys Asn Gly Ile Lys Val Asn Phe Lys Ile Arg His Asn Ile Glu
        195                 200                 205

Asp Gly Ser Val Gln Leu Ala Asp His Tyr Gln Gln Asn Thr Pro Ile
    210                 215                 220

Gly Asp Gly Pro Val Glu Leu Pro Asp Asn His Tyr Leu Ser Thr Gln
225                 230                 235                 240

Ser Ala Leu Ser Lys Asp Pro Asn Glu Lys Arg Asp His Ile Val Leu
                245                 250                 255

Leu Glu Phe Val Thr Ala Ala Gly Ile Thr Leu Gly Met Asp Glu Leu
            260                 265                 270

Tyr Lys

<210> SEQ ID NO 67
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 67

Met Val Ser Lys Gly Glu Glu Leu Phe Thr Gly Val Val Pro Ile Asp
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Ser Asn Glu Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235
```

-continued

<210> SEQ ID NO 68
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 68

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Asp Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Glu Met Asp Asp Lys Gln Lys Asn
145                 150                 155                 160

Gly Asp Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Glu Leu Pro Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 69
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 69

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Asp Leu Val Thr Thr
        50                  55                  60

```
Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Glu Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ser Leu Gly His Lys Asn Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Glu Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 70
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 70

Met Val Ser Lys Gly Glu Glu Asp Phe Thr Gly Val Asn Pro Ile Leu
  1               5                  10                  15

Val Glu Leu Asp Gly Asp Leu Asn Gly His Lys Phe Ser Val Ser Gly
                 20                  25                  30

Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
         50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Ser Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Asp Glu Gly Asp Thr Asp Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190
```

-continued

Pro Val Leu Leu Pro Asp Asn His Tyr Leu Ser Thr Gln Ser Ala Leu
            195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 71
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 71

Met Val Ser Lys Gly Glu Glu Asp Phe Thr Gly Val Asn Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Thr Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Asp Glu Gly Asp Thr Glu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 72
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 72

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly

```
            20                  25                  30
Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
            50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Asp Phe Glu Gly Asp Thr Leu Asn Asn Asp Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Ile Val Leu Leu Glu Phe
            210                 215                 220

Val Thr Ala Ala Gly Ile Thr Leu Gly Met Asp Glu Leu Tyr Lys
225                 230                 235

<210> SEQ ID NO 73
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 73

Met Val Ser Lys Gly Glu Glu Leu Phe Thr Gly Val Val Pro Ile Asn
 1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
            50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Asn Asn Asp Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
```

-continued

```
                    145                 150                 155                 160
Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 74
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 74

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Asp Glu Asp Gly Asp
                165                 170                 175

Val Asn Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 75
<211> LENGTH: 239
<212> TYPE: PRT
<213> ORGANISM: artificial sequence
<220> FEATURE:
<223> OTHER INFORMATION: Description of Artificial Sequence: Synthetic
```

EGFP

<400> SEQUENCE: 75

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Asp
65                  70                  75                  80

Gln His Asp Phe Phe Asp Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Asn Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
210                 215                 220

Val Thr Ala Ala Gly Ile Thr Leu Gly Met Asp Glu Leu Tyr Lys
225                 230                 235

<210> SEQ ID NO 76
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 76

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Asp
65                  70                  75                  80

Gln His Asp Phe Phe Lys Asp Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
    115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Asn Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 77
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 77

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Asn Lys
65                  70                  75                  80

Gln Asp Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn Asp Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Asp Thr Leu Gly Met Asp Glu Leu Tyr Lys
225                 230                 235

<210> SEQ ID NO 78
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 78

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Asp Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Glu Leu Pro Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 79
<211> LENGTH: 267
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 79

Met Leu Leu Ser Val Pro Leu Leu Leu Gly Leu Leu Gly Leu Ala Ala
1               5                   10                  15

Ala Asp Gly Ser Gly Pro Ser Arg Met Val Ser Lys Gly Glu Glu Leu
            20                  25                  30

Phe Thr Gly Val Val Pro Ile Leu Val Glu Leu Asp Gly Asp Leu Asn
        35                  40                  45

Gly His Lys Phe Ser Val Ser Gly Glu Gly Glu Gly Asp Ala Thr Tyr
    50                  55                  60

```
Gly Lys Leu Thr Leu Lys Phe Ile Cys Thr Thr Gly Lys Leu Pro Val
 65                  70                  75                  80

Pro Trp Pro Thr Leu Val Thr Thr Leu Thr Tyr Gly Val Gln Cys Phe
                 85                  90                  95

Ser Arg Tyr Pro Asp His Met Lys Gln His Asp Phe Phe Lys Asp Ala
            100                 105                 110

Met Pro Glu Gly Tyr Val Gln Glu Arg Thr Ile Phe Phe Lys Asp Asp
        115                 120                 125

Gly Asn Tyr Lys Thr Arg Ala Glu Val Lys Phe Glu Gly Asp Thr Leu
    130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Ser His Asn Val Tyr
                165                 170                 175

Ile Thr Ala Asp Lys Gln Lys Asn Gly Ile Lys Ala Asn Phe Lys Ile
            180                 185                 190

Arg His Asn Ile Glu Asp Gly Ser Val Gln Leu Ala Asp His Tyr Gln
        195                 200                 205

Gln Asn Thr Pro Ile Gly Asp Gly Pro Val Glu Leu Pro Asp Asn His
    210                 215                 220

Tyr Leu Ser Thr Gln Ser Ala Leu Ser Lys Asp Pro Asn Glu Lys Arg
225                 230                 235                 240

Asp His Ile Val Leu Leu Glu Phe Val Thr Ala Ala Gly Ile Thr Leu
                245                 250                 255

Gly Met Asp Glu Leu Tyr Lys Lys Asp Glu Leu
            260                 265

<210> SEQ ID NO 80
<211> LENGTH: 274
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 80

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Gly Ser Gly
                20                  25                  30

Pro Ser Arg Met Val Ser Lys Gly Glu Glu Leu Phe Thr Gly Val Val
            35                  40                  45

Pro Ile Leu Val Glu Leu Asp Gly Asp Leu Asn Gly His Lys Phe Ser
        50                  55                  60

Val Ser Gly Glu Gly Glu Gly Asp Ala Thr Tyr Gly Lys Leu Thr Leu
 65                  70                  75                  80

Lys Phe Ile Cys Thr Thr Gly Lys Leu Pro Val Pro Trp Pro Thr Leu
                 85                  90                  95

Val Thr Thr Leu Thr Tyr Gly Val Gln Cys Phe Ser Arg Tyr Pro Asp
            100                 105                 110

His Met Lys Gln His Asp Phe Phe Lys Asp Ala Met Pro Glu Gly Tyr
        115                 120                 125

Val Gln Glu Arg Thr Ile Phe Phe Lys Asp Asp Gly Asn Tyr Lys Thr
    130                 135                 140

Arg Ala Glu Val Lys Phe Glu Gly Asp Thr Leu Val Asn Arg Ile Glu
145                 150                 155                 160
```

```
Leu Lys Gly Ile Asp Phe Lys Glu Asp Gly Asn Ile Leu Gly His Lys
            165                 170                 175
Leu Glu Tyr Asn Tyr Asn Ser His Asn Val Tyr Ile Thr Ala Asp Lys
        180                 185                 190
Gln Lys Asn Gly Ile Lys Ala Asn Phe Lys Ile Arg His Asn Ile Glu
        195                 200                 205
Asp Gly Ser Val Gln Leu Ala Asp His Tyr Gln Gln Asn Thr Pro Ile
        210                 215                 220
Gly Asp Gly Pro Val Glu Leu Pro Asp Asn His Tyr Leu Ser Thr Gln
225                 230                 235                 240
Ser Ala Leu Ser Lys Asp Pro Asn Glu Lys Arg Asp His Ile Val Leu
                245                 250                 255
Leu Glu Phe Val Thr Ala Ala Gly Ile Thr Leu Gly Met Asp Glu Leu
            260                 265                 270
Tyr Lys

<210> SEQ ID NO 81
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 81

Met Val Ser Lys Gly Glu Glu Leu Phe Thr Gly Val Val Pro Ile Asp
1               5                   10                  15
Val Glu Leu Asp Gly Asp Val Asn Gly His Lys Phe Ser Val Ser Gly
            20                  25                  30
Glu Gly Glu Gly Asp Ala Thr Tyr Gly Lys Leu Thr Leu Lys Phe Ile
        35                  40                  45
Cys Thr Thr Gly Lys Leu Pro Val Pro Trp Pro Thr Leu Val Thr Thr
    50                  55                  60
Leu Thr Tyr Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Ser Asn Glu Ile Glu Leu Lys Gly
        115                 120                 125
Ile Asp Phe Lys Glu Asp Gly Asn Ile Leu Gly His Lys Leu Glu Tyr
    130                 135                 140
Asn Tyr Asn Ser His Asn Val Tyr Ile Thr Ala Asp Lys Gln Lys Asn
145                 150                 155                 160
Gly Ile Lys Ala Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Ala Leu
        195                 200                 205
Ser Lys Asp Pro Asn Glu Lys Arg Asp His Ile Val Leu Leu Glu Phe
    210                 215                 220
Val Thr Ala Ala Gly Ile Thr Leu Gly Met Asp Glu Leu Tyr Lys
225                 230                 235
```

```
<210> SEQ ID NO 82
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 82

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Asp Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Glu Thr Asp Asp Lys Gln Lys Asn
145                 150                 155                 160

Gly Asp Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Glu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 83
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 83

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Asp Leu Val Thr Thr
    50                  55                  60

Leu Thr Tyr Gly Val Gln Cys Phe Ser Arg Tyr Pro Asp His Met Lys
65                  70                  75                  80
```

```
Gln His Asp Phe Phe Lys Ser Ala Met Pro Glu Gly Tyr Val Gln Glu
                85                  90                  95

Arg Thr Ile Phe Glu Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ser Leu Gly His Lys Asn Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Glu Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 84
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 84

Met Val Ser Lys Gly Glu Glu Asp Phe Thr Gly Val Asn Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Ser Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Asp Glu Gly Asp Thr Asp Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205
```

```
Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 85
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 85

```
Met Val Ser Lys Gly Glu Glu Asp Phe Thr Gly Val Asn Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Thr Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Asp Glu Gly Asp Thr Glu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 86
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 86

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30
```

```
Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Ser Phe Lys Asp Asp Gly Asn Tyr Lys Thr Arg Ala Glu
            100                 105                 110

Val Asp Phe Glu Gly Asp Thr Leu Asn Asn Asp Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 87
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 87

Met Val Ser Lys Gly Glu Glu Leu Phe Thr Gly Val Val Pro Ile Asn
 1               5                  10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Asn Asn Asp Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160
```

```
Gly Ile Lys Ala Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
        210                 215                 220

Val Thr Ala Ala Gly Ile Thr Leu Gly Met Asp Glu Leu Tyr Lys
225                 230                 235

<210> SEQ ID NO 88
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 88

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Asp Glu Asp Gly Asp
            165                 170                 175

Val Asn Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
        210                 215                 220

Val Thr Ala Ala Gly Ile Thr Leu Gly Met Asp Glu Leu Tyr Lys
225                 230                 235

<210> SEQ ID NO 89
<211> LENGTH: 239
<212> TYPE: PRT
<213> ORGANISM: artificial sequence
<220> FEATURE:
<223> OTHER INFORMATION: Description of Artificial Sequence: Synthetic
      EGFP
```

-continued

<400> SEQUENCE: 89

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Asp
65                  70                  75                  80

Gln His Asp Phe Phe Asp Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Asn Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 90
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 90

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Asp
65                  70                  75                  80

Gln His Asp Phe Phe Lys Asp Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly

```
                   115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Asn Leu Pro Asp Asn His Tyr Leu Ser Thr Gln Ser Ala Leu
                195                 200                 205

Ser Lys Asp Pro Asn Glu Lys Arg Asp His Ile Val Leu Leu Glu Phe
                210                 215                 220

Val Thr Ala Ala Gly Ile Thr Leu Gly Met Asp Glu Leu Tyr Lys
225                 230                 235

<210> SEQ ID NO 91
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 91

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Asn Lys
65                  70                  75                  80

Gln Asp Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn Asp Tyr Leu Ser Thr Gln Ser Ala Leu
                195                 200                 205

Ser Lys Asp Pro Asn Glu Lys Arg Asp His Ile Val Leu Leu Glu Phe
                210                 215                 220

Val Thr Ala Ala Gly Asp Thr Leu Gly Met Asp Glu Leu Tyr Lys
225                 230                 235
```

```
<210> SEQ ID NO 92
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 92

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Asp Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Glu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 93
<211> LENGTH: 267
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 93

Met Leu Leu Ser Val Pro Leu Leu Leu Gly Leu Leu Gly Leu Ala Ala
1               5                   10                  15

Ala Asp Gly Ser Gly Pro Ser Arg Met Val Ser Lys Gly Glu Glu Leu
            20                  25                  30

Phe Thr Gly Val Val Pro Ile Leu Val Glu Leu Asp Gly Asp Leu Asn
        35                  40                  45

Gly His Lys Phe Ser Val Ser Gly Glu Gly Glu Gly Asp Ala Thr Tyr
    50                  55                  60

Gly Lys Leu Thr Leu Lys Phe Ile Cys Thr Thr Gly Lys Leu Pro Val
65                  70                  75                  80
```

```
Pro Trp Pro Thr Leu Val Thr Thr Leu Thr Tyr Gly Val Gln Cys Phe
                85                  90                  95

Ser Arg Tyr Pro Asp His Met Lys Gln His Asp Phe Phe Lys Asp Ala
            100                 105                 110

Met Pro Glu Gly Tyr Val Gln Glu Arg Thr Ile Ser Phe Lys Asp Asp
        115                 120                 125

Gly Asn Tyr Lys Thr Arg Ala Glu Val Lys Phe Glu Gly Asp Thr Leu
    130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Ser His Asn Val Tyr
                165                 170                 175

Ile Thr Ala Asp Lys Gln Lys Asn Gly Ile Lys Ala Asn Phe Lys Ile
            180                 185                 190

Arg His Asn Ile Glu Asp Gly Ser Val Gln Leu Ala Asp His Tyr Gln
        195                 200                 205

Gln Asn Thr Pro Ile Gly Asp Gly Pro Val Glu Leu Pro Asp Asn His
    210                 215                 220

Tyr Leu Ser Thr Gln Ser Ala Leu Ser Lys Asp Pro Asn Glu Lys Arg
225                 230                 235                 240

Asp His Ile Val Leu Leu Glu Phe Val Thr Ala Ala Gly Ile Thr Leu
                245                 250                 255

Gly Met Asp Glu Leu Tyr Lys Lys Asp Glu Leu
            260                 265

<210> SEQ ID NO 94
<211> LENGTH: 274
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 94

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Gly Ser Gly
            20                  25                  30

Pro Ser Arg Met Val Ser Lys Gly Glu Glu Leu Phe Thr Gly Val Val
        35                  40                  45

Pro Ile Leu Val Glu Leu Asp Gly Asp Leu Asn Gly His Lys Phe Ser
    50                  55                  60

Val Ser Gly Glu Gly Glu Gly Asp Ala Thr Tyr Gly Lys Leu Thr Leu
65                  70                  75                  80

Lys Phe Ile Cys Thr Thr Gly Lys Leu Pro Val Pro Trp Pro Thr Leu
                85                  90                  95

Val Thr Thr Leu Thr Tyr Gly Val Gln Cys Phe Ser Arg Tyr Pro Asp
            100                 105                 110

His Met Lys Gln His Asp Phe Phe Lys Asp Ala Met Pro Glu Gly Tyr
        115                 120                 125

Val Gln Glu Arg Thr Ile Ser Phe Lys Asp Asp Gly Asn Tyr Lys Thr
    130                 135                 140

Arg Ala Glu Val Lys Phe Glu Gly Asp Thr Leu Val Asn Arg Ile Glu
145                 150                 155                 160

Leu Lys Gly Ile Asp Phe Lys Glu Asp Gly Asn Ile Leu Gly His Lys
                165                 170                 175
```

```
Leu Glu Tyr Asn Tyr Asn Ser His Asn Val Tyr Ile Thr Ala Asp Lys
                180                 185                 190

Gln Lys Asn Gly Ile Lys Ala Asn Phe Lys Ile Arg His Asn Ile Glu
        195                 200                 205

Asp Gly Ser Val Gln Leu Ala Asp His Tyr Gln Gln Asn Thr Pro Ile
    210                 215                 220

Gly Asp Gly Pro Val Glu Leu Pro Asp Asn His Tyr Leu Ser Thr Gln
225                 230                 235                 240

Ser Ala Leu Ser Lys Asp Pro Asn Glu Lys Arg Asp His Ile Val Leu
                245                 250                 255

Leu Glu Phe Val Thr Ala Ala Gly Ile Thr Leu Gly Met Asp Glu Leu
            260                 265                 270

Tyr Lys

<210> SEQ ID NO 95
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 95

Met Val Ser Lys Gly Glu Glu Leu Phe Thr Gly Val Val Pro Ile Asp
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Ser Asn Glu Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 96
<211> LENGTH: 239
```

```
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 96

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Asp Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Glu Thr Asp Asp Lys Gln Lys Asn
145                 150                 155                 160

Gly Asp Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Glu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 97
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 97

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Asp Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
```

```
                    85                  90                  95
Arg Thr Ile Ser Glu Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ser Leu Gly His Lys Asn Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Glu Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
                195                 200                 205

Ser Lys Asp Pro Asn Glu Lys Arg Asp His Ile Val Leu Leu Glu Phe
                210                 215                 220

Val Thr Ala Ala Gly Ile Thr Leu Gly Met Asp Glu Leu Tyr Lys
225                 230                 235

<210> SEQ ID NO 98
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 98

Met Val Ser Lys Gly Glu Glu Asp Phe Thr Gly Val Asn Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Ser Pro Glu Gly Tyr Val Gln Glu
                85                  90                  95

Arg Thr Ile Ser Phe Lys Asp Asp Gly Asn Tyr Lys Thr Arg Ala Glu
                100                 105                 110

Val Lys Asp Glu Gly Asp Thr Asp Val Asn Arg Ile Glu Leu Lys Gly
                115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
                195                 200                 205

Ser Lys Asp Pro Asn Glu Lys Arg Asp His Ile Val Leu Leu Glu Phe
```

```
                210                 215                 220
Val Thr Ala Ala Gly Ile Thr Leu Gly Met Asp Glu Leu Tyr Lys
225                 230                 235

<210> SEQ ID NO 99
<211> LENGTH: 239
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 99

Met Val Ser Lys Gly Glu Glu Asp Phe Thr Gly Val Asn Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Thr Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Asp Glu Gly Asp Thr Glu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 100
<211> LENGTH: 24
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 100

Met Leu Leu Ser Val Pro Leu Leu Leu Gly Leu Leu Gly Leu Ala Ala
1               5                   10                  15

Ala Asp Gly Ser Gly Pro Ser Arg
                20

<210> SEQ ID NO 101
```

```
<211> LENGTH: 4
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 101

Lys Asp Glu Leu
1

<210> SEQ ID NO 102
<211> LENGTH: 35
<212> TYPE: PRT
<213> ORGANISM: artificial sequence
<220> FEATURE:
<223> OTHER INFORMATION: Description of Artificial Sequence: Synthetic
      EGFP

<400> SEQUENCE: 102

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Gly Ser Gly
            20                  25                  30

Pro Ser Arg
        35
```